US008920775B2

(12) United States Patent
Petersen et al.

(10) Patent No.: US 8,920,775 B2
(45) Date of Patent: Dec. 30, 2014

(54) LOADING TECHNIQUE FOR PREPARING RADIONUCLIDE CONTAINING NANOPARTICLES

(75) Inventors: Anncatrine Luisa Petersen, Nivå (DK); Palle Hedengran Rasmussen, Taastrup (DK); Jonas Rosager Henriksen, Allerød (DK); Andreas Kjær, Frederiksberg (DK); Thomas Lars Andresen, Vanløse (DK)

(73) Assignees: Technical University of Denmark (DK); Rigshospitalet (DK)

( * ) Notice: Subject to any disclaimer, the term of this patent is extended or adjusted under 35 U.S.C. 154(b) by 158 days.

(21) Appl. No.: 13/383,310

(22) PCT Filed: Jul. 16, 2010

(86) PCT No.: PCT/DK2010/050192
§ 371 (c)(1),
(2), (4) Date: May 9, 2012

(87) PCT Pub. No.: WO2011/006510
PCT Pub. Date: Jan. 20, 2011

(65) Prior Publication Data
US 2012/0213698 A1    Aug. 23, 2012

Related U.S. Application Data

(60) Provisional application No. 61/300,782, filed on Feb. 2, 2010.

(30) Foreign Application Priority Data

Jul. 17, 2009 (DK) ................................ 2009 00879
Feb. 2, 2010 (EP) .................................... 10152394

(51) Int. Cl.
*A61K 51/12* (2006.01)
*A61K 9/127* (2006.01)
*C07B 59/00* (2006.01)

(52) U.S. Cl.
CPC ................. *C07B 59/00* (2013.01); *A61K 9/127* (2013.01); *A61K 51/1234* (2013.01)
USPC ..................................................... 424/1.29

(58) Field of Classification Search
USPC .......... 424/1.21, 1.29, 1.37, 9.321, 9.51, 450, 424/489
See application file for complete search history.

(56) References Cited

U.S. PATENT DOCUMENTS

| 5,182,398 A | 1/1993 | Kasuga et al. |
| 5,213,804 A | 5/1993 | Martin et al. |
| 5,525,232 A | 6/1996 | Veiro et al. |
| 5,688,488 A | 11/1997 | Low et al. |
| 5,837,282 A * | 11/1998 | Fenske et al. ................. 424/450 |
| 5,945,502 A | 8/1999 | Hsieh et al. |
| 2009/0081121 A1 * | 3/2009 | Ting et al. ..................... 424/1.21 |

FOREIGN PATENT DOCUMENTS

| EP | 0386146 | 9/1990 |
| WO | WO 01/60417 | 8/2001 |
| WO | WO 2004/082626 | 9/2004 |
| WO | WO 2004/082627 | 9/2004 |
| WO | WO 2006/021008 | 2/2006 |
| WO | WO 2006/043083 | 4/2006 |
| WO | WO 2006/095234 | 9/2006 |
| WO | WO 2009/140215 | 11/2009 |

OTHER PUBLICATIONS

Arianna Friggeri et al. Entrapment and release of quinolinederivatives using a hydrogel of a lowe molecular weight gelator, Journal of Controlled Release 97, 241-248, 2004.*
Friggeri, A, et al. "Entrapment and Release of Quinoline Derivatives Using a Hydrogel of a Low Molecular Weight Gelator," *Journal of Controlled Release*, 97 (2004) pp. 241-238.
Allen et al, Drug Delivery Systems: Entering the Mainstream, Science, 303, 1818-1822, 2004.
Anderson et al, In Vitro and In Vivo Evaluation of Copper-64-Octreotide Conjugates, The Journal of Nuclear Medicine, vol. 36, 2315-2325, 1995.
Choi & Hwang. Mechanism of ionophoric transport of indium-111 cations through a lipid bilayer membrane. J Nucl Med (1987) 28:91-96.
Crescitelli. Effects of oxine, carbostyril and quinoline on frog nerve. Am J Physiol (1950) 163:197-200.
Dehdashti et al, Initial results with pet imaging using Cu-64-labeled teta-octreotide in patients with carcinoid tumor, The Journal of Nuclear Medicine, vol. 38, 103P, 1997.
Emfietzoglou et al, An Analytic Dosimetry Study for the Use of Radionuclide-Liposome Conjugates in Internal Radiotherapy, The Journal of Nuclear Medicine, vol. 42, 3, 499-504, 2001.
Ferrara et al, Lipid-Shelled Vehicles: Engineering for Ultrasound Molecular Imaging and Drug Delivery, Acc. of Chemical Research, vol. 42, 881-892, 2009.

(Continued)

*Primary Examiner* — Michael G Hartley
*Assistant Examiner* — Jagadishwar Samala
(74) *Attorney, Agent, or Firm* — Sunstein Kann Murphy & Timbers LLP

(57) ABSTRACT

The present invention relates to a novel composition and method for loading delivery systems such as liposome compositions with radionuclides useful in targeted diagnostic and/or therapy of target site, such as cancerous tissue and, in general, pathological conditions associated with leaky blood vessels. The composition and methods of the invention find particular use in diagnosing and imaging cancerous tissue and, in general, pathological conditions associated with leaky blood vessels in a subject. The present invention provides a new diagnostic tool for the utilization of positron emission tomography (PET) imaging technique. One specific aspect of the invention is directed to a method of producing nanoparticles with desired targeting properties for diagnostic and/or radio-therapeutic applications.

14 Claims, 27 Drawing Sheets

(56) References Cited

OTHER PUBLICATIONS

Figure 1:
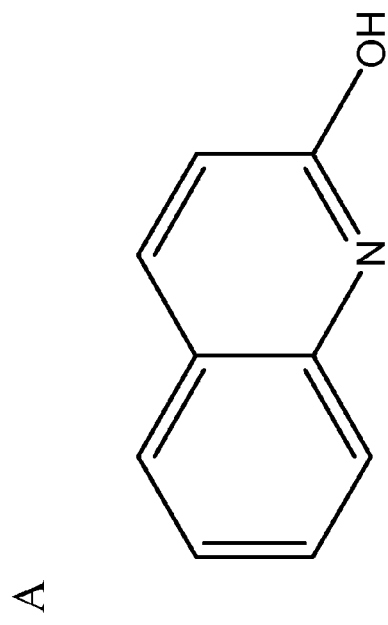
Figure 1:
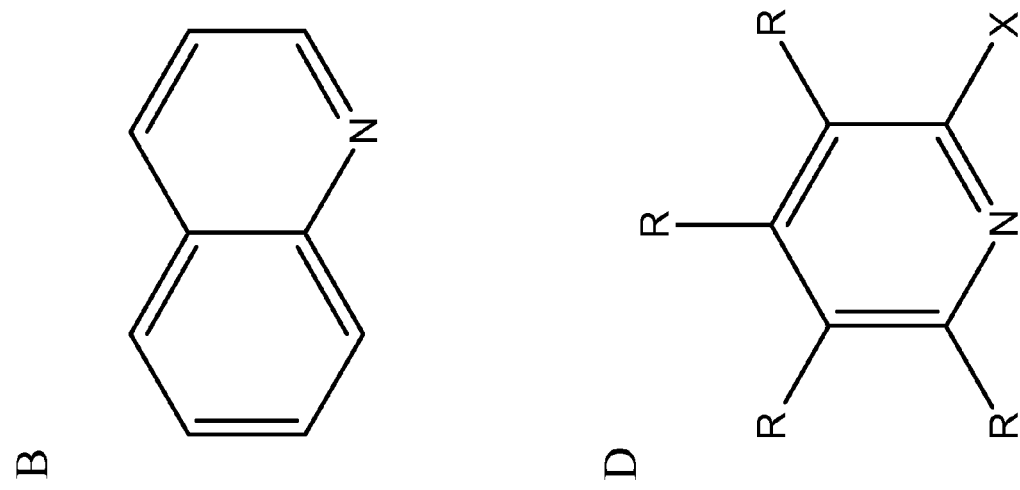
Figure 1:
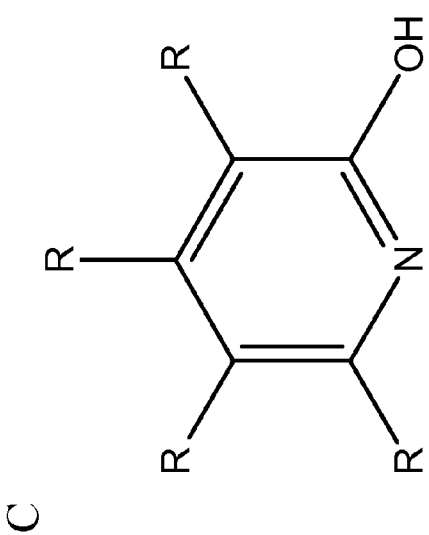
Figure 1:
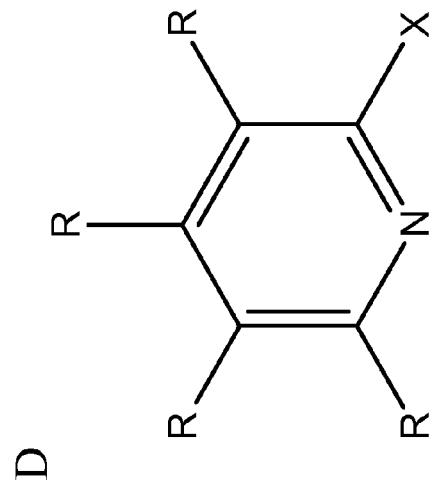

Gabizon et al, An Improved Method for in Vivo Tracing and Imaging of Liposomes Using a Gallium 67-Deferoxamine Complex, Journal of Liposome Research, 1, 123-135, 1988.

Gabizon et al, Effect of Liposome Composition and Other Factors on the Targeting of Liposomes to Experimental Tumors:Biodistribution and Imaging Studies, Cancer Research, 50, 6371-6378, 1990.

Goto et al, Liposomes prepared from synthetic amphiphiles. I. Their Technetium labeling and stability, Chem. Pharm. Bull., 37, 1351-1354, 1989.

Henriksen et al, Sterically stabilized liposomes as a carrier for a-emitting radium and actinium radionuclides, Nucl. Med. Bio., 31, 441-449, 2004.

Hwang et al, Encapsulation, with high efficiency, of radioactive metal ions in liposomes, Biochim Biophys Acta., 716, 101-109, 1982.

Kostarelos et al, Liposomes as Carriers of Radionuclides: From Imaging to Therapy, Journal of Liposome Research, 9, 429-460, 1999.

Kostarelos et al. Liposome-mediated delivery of radionuclides to tumor models for cancer radiotherapy: a quantitative analysis. Journal of Liposome Research (1999) 9(3):407-424.

Lasic, Dan D., Novel applications of liposomes, Trends Biotechnol., 25 16, 307-321, 1998.

Mittal et al. 8-Hydroxyquinoline based neutral tripodal ionophore as a copper (II) selective electrode and the effect of remote substituents on electrode properties. Analytica Chimica Acta (2007) 585:161-170.

Morgan et al, Localisation of Experimental Staphylococcal Abscesses by 99MTC-Technetium-Labelled Liposomes, J Med Microbiol. vol. 14, 213-217, 1981.

Phillips et al, A simple method for producing a technetium-99m-labeled liposome which is stable In Vivo, Nucl. Med. Biol., vol. 19, No. 5, pp. 539-547, 1992, Int. J Rad. Appl. Instrum B.

Phillips, William T., Delivery of gamma-imaging agents by liposomes, Advanced Drug Delivery Reviews 37, 13-32, 1999.

Seo et al, A Novel Method to Label Preformed Liposomes with 64Cu for Positron Emission Tomography (PET) Imaging, Bioconjucate Chemistry, 19, 2577-2584, 2008.

Seo, Youngho, Quantification of SPECT and PET for Drug Development, Curr. Radiopharm., 1, 17-21, 2008.

Wang et al. International radiotherapy and dosimetric study for 111In/177Lu-pegylated liposomes conjugates in tumor-bearing mice. Nuclear Instruments and Methods in Physics Research, 2006, pp. 533-537.

Zhai et al. Tumor cellular proteasome inhibition and growth suppression by 8-hydroxyquinoline and clioquinol requires their capabilities to bind copper and transport copper into cells. J Biol. Inorg Chem (2010 15:259-269.

\* cited by examiner

A

B

C

D

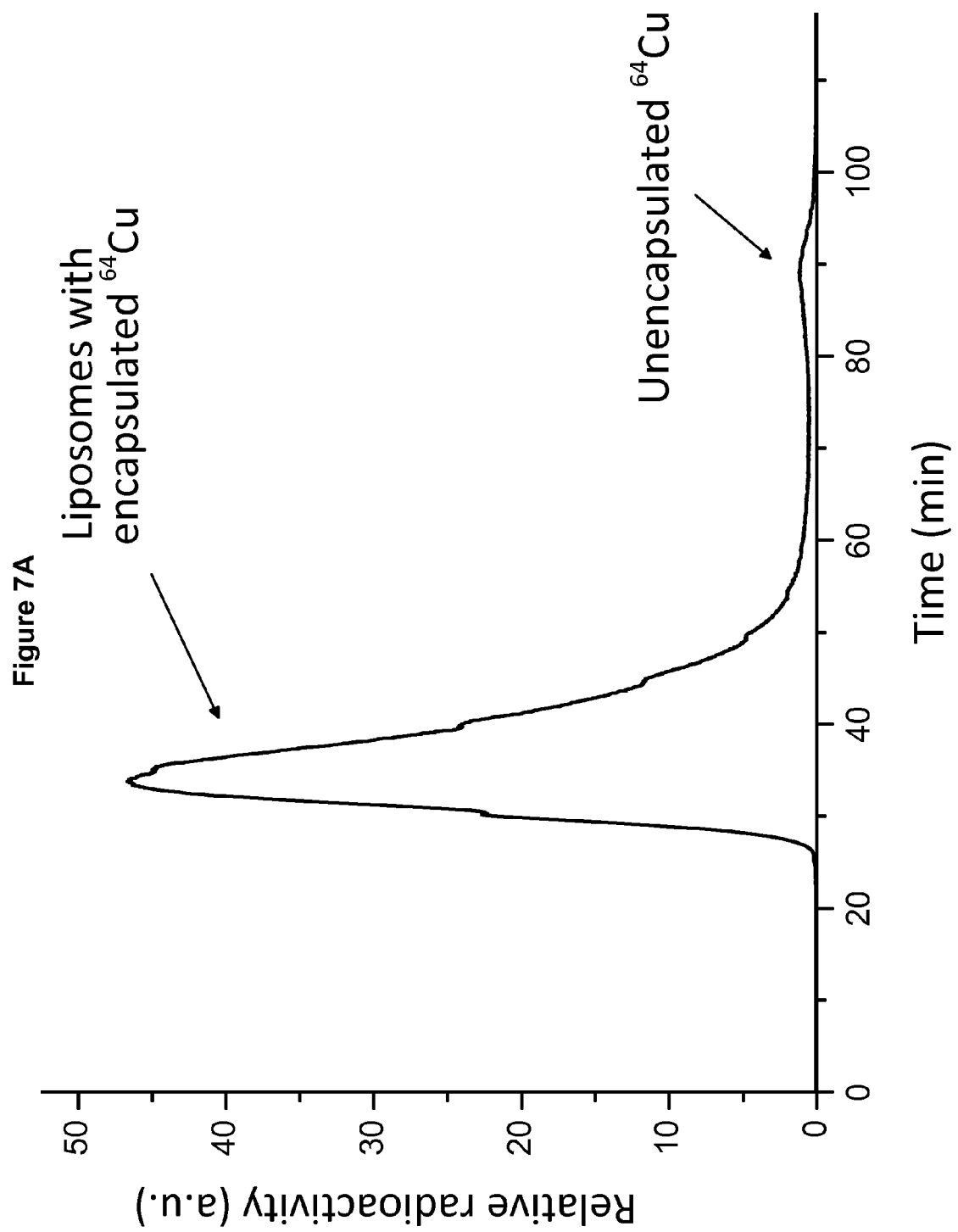

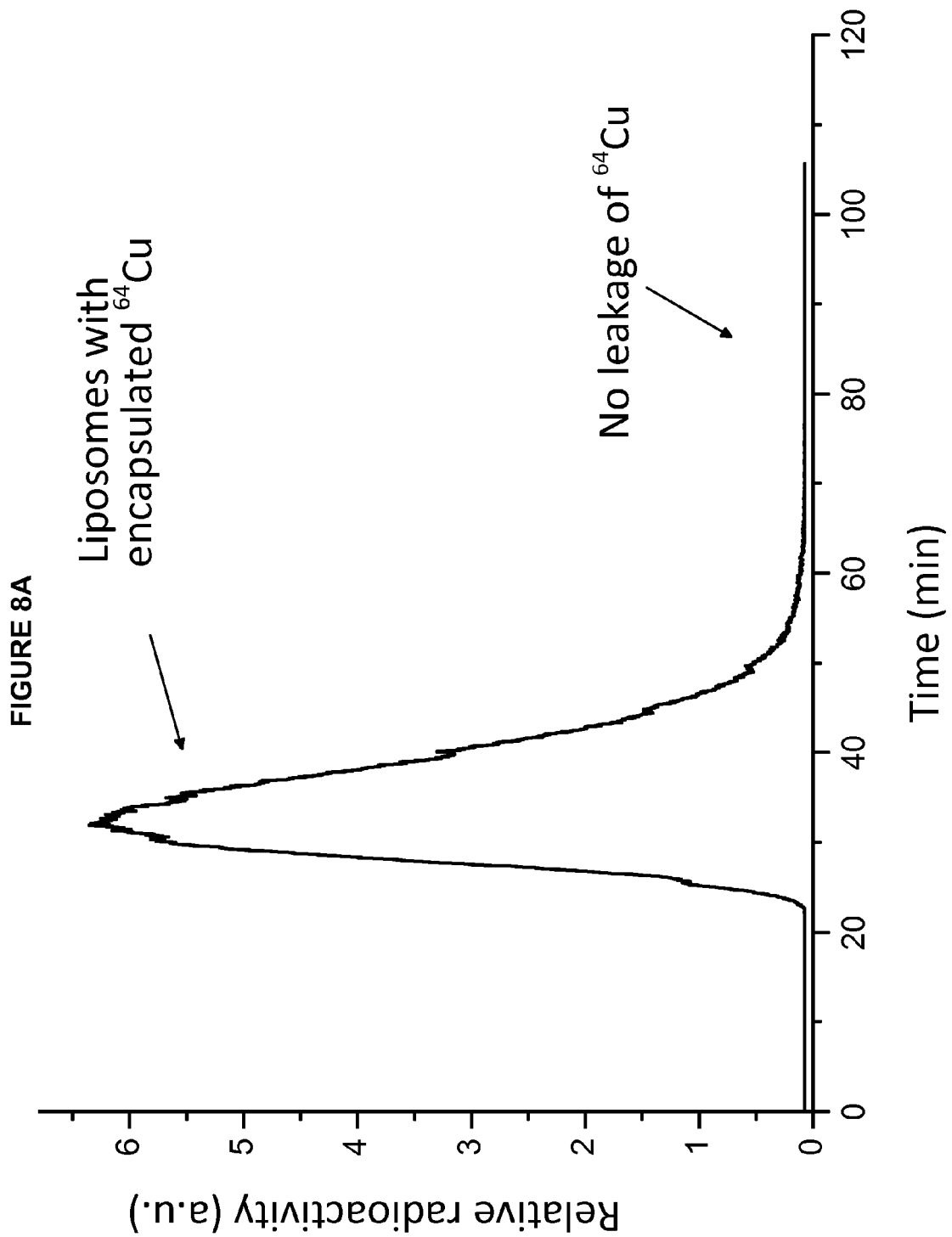

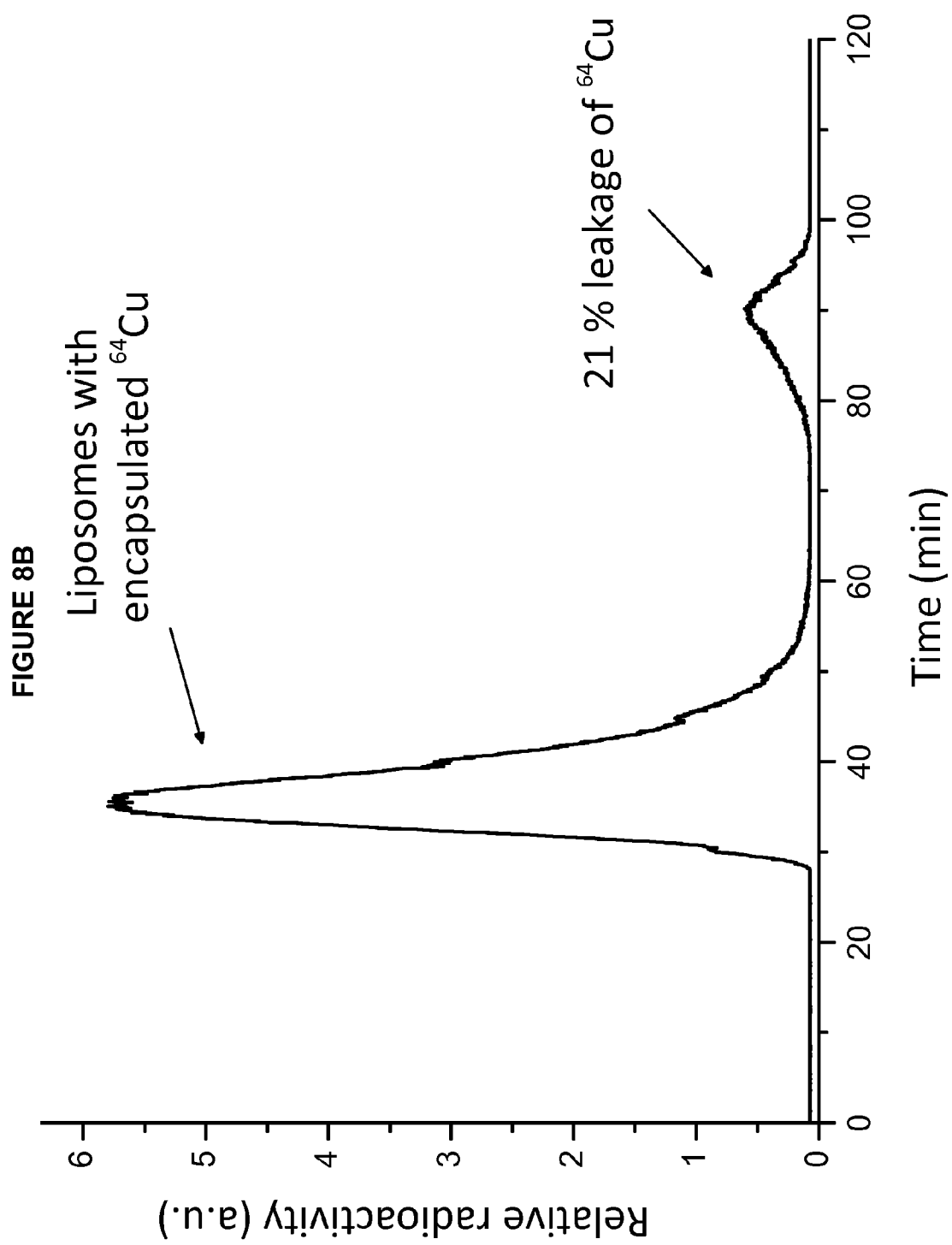

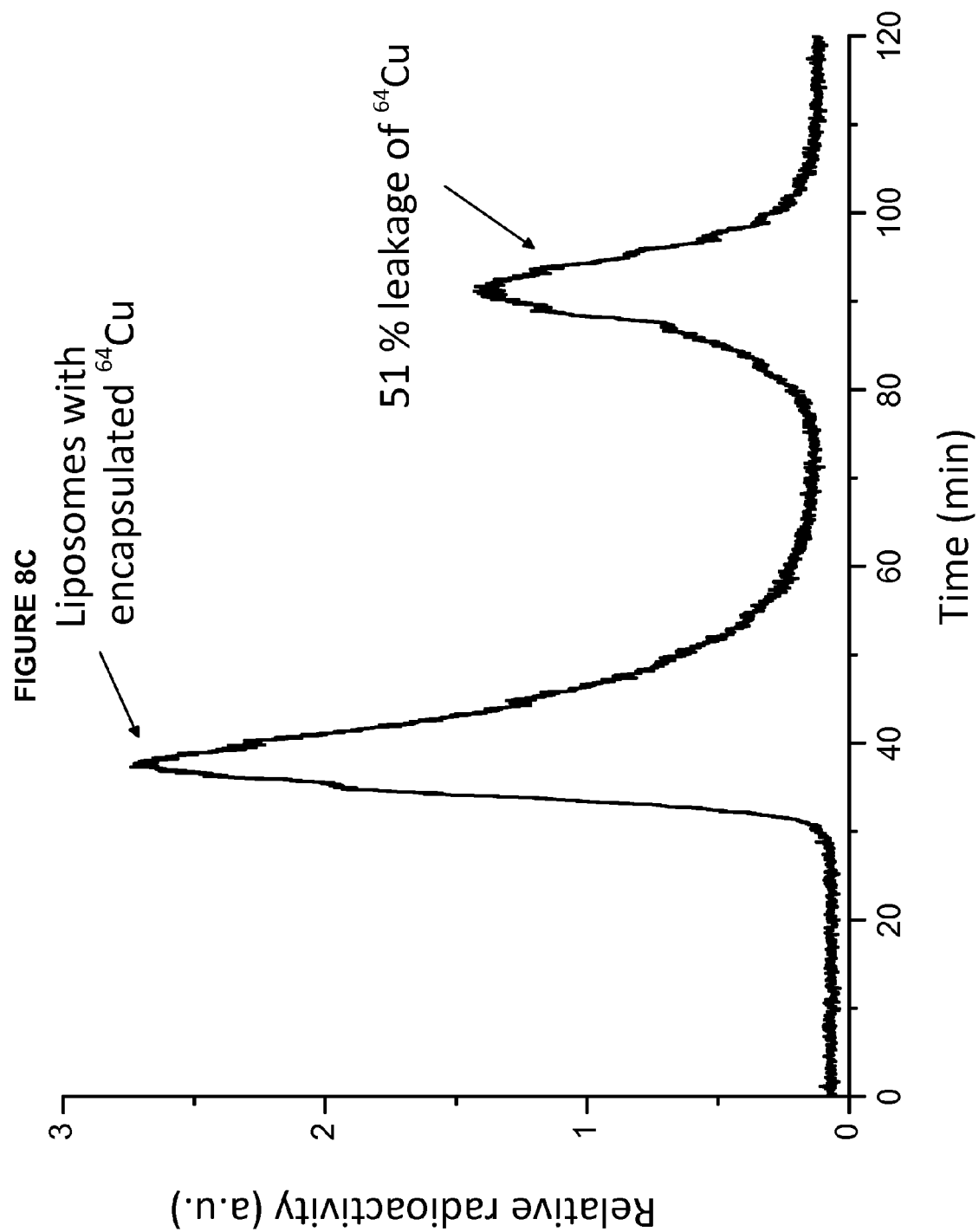

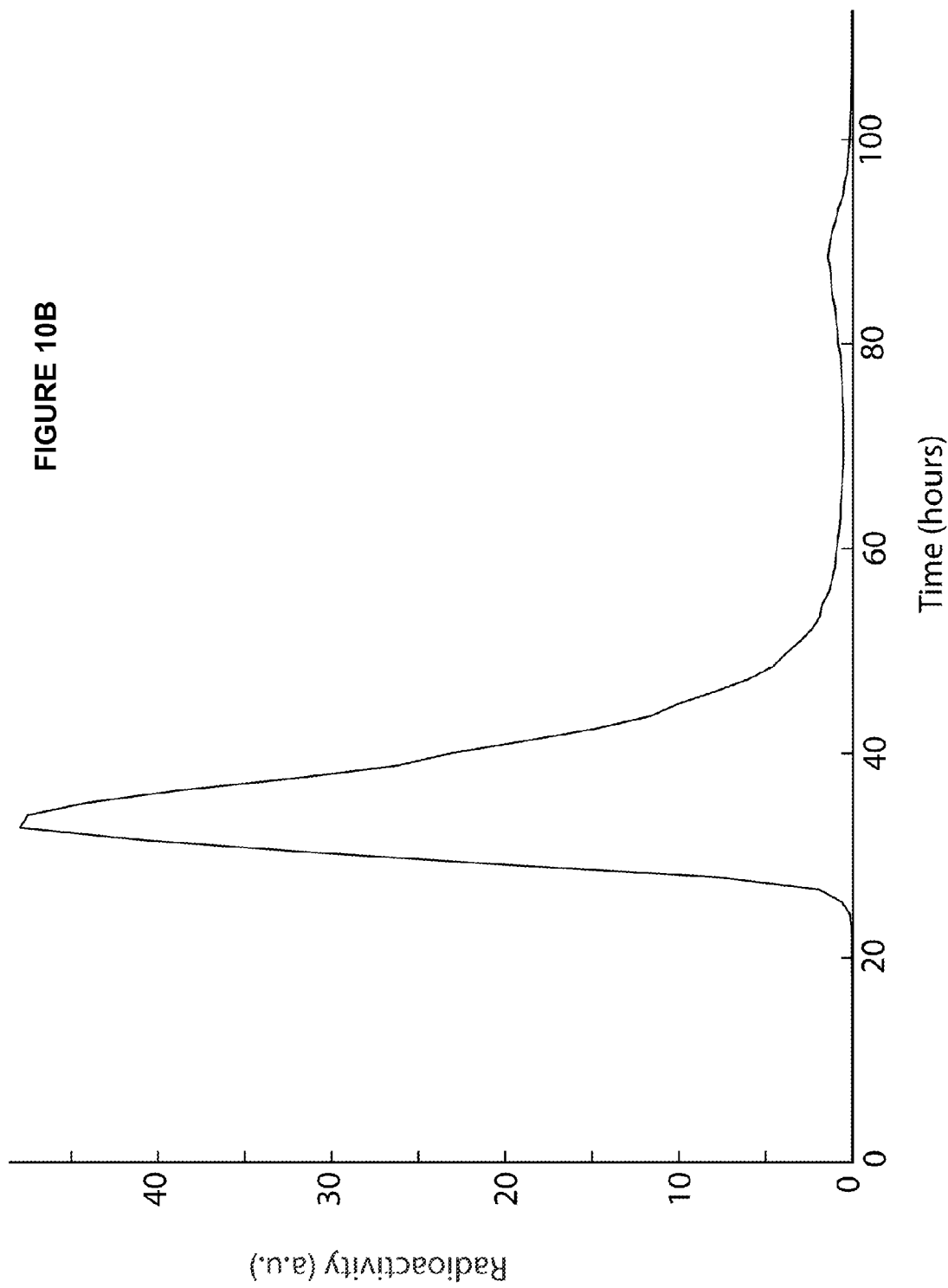

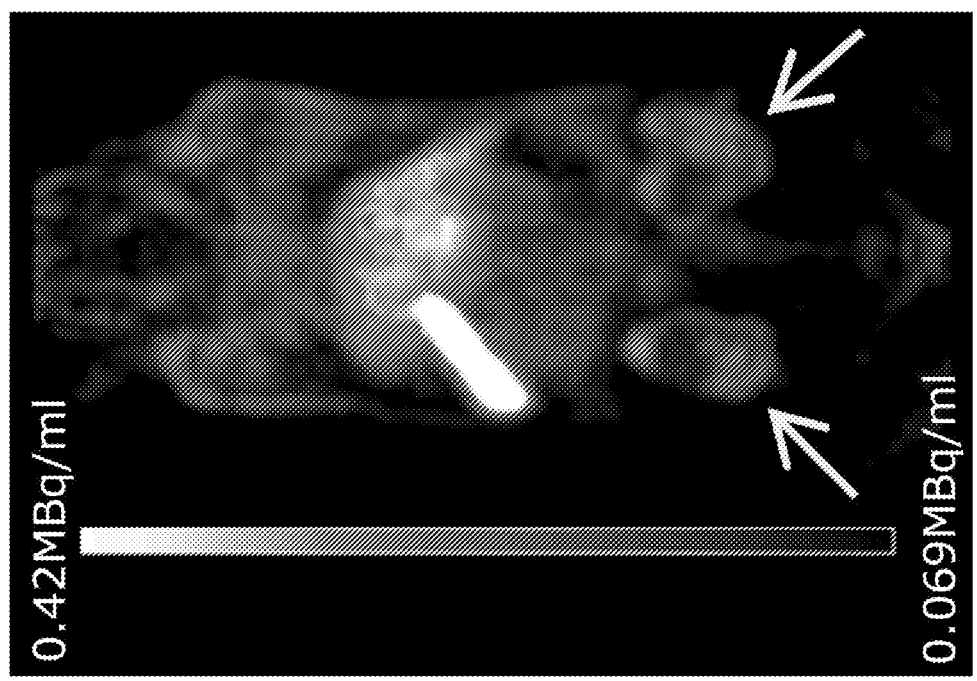

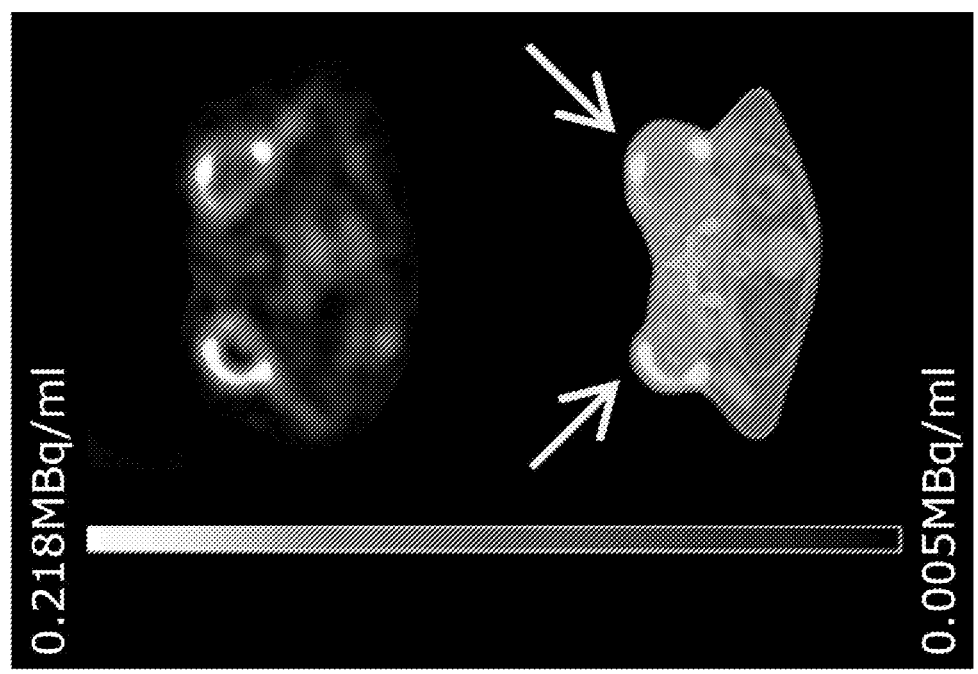

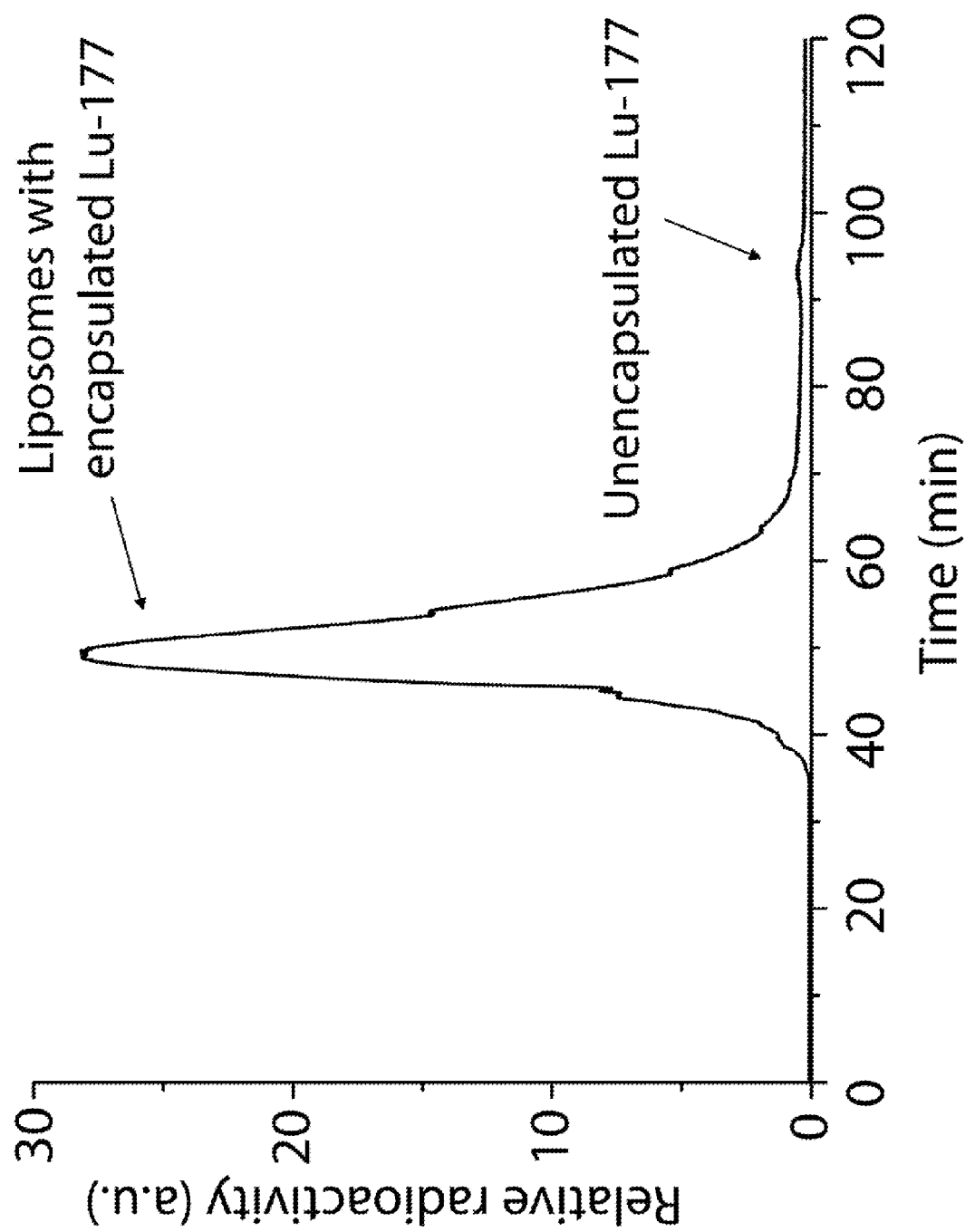

LOADING TECHNIQUE FOR PREPARING RADIONUCLIDE CONTAINING NANOPARTICLES

This application is a PCT application with priority of DK application with the serial no. PA 2009 00879 filed 17. Jul. 2009, U.S. provisional application with the Ser. No. 61/300, 782 filed 2. Feb. 2010, and the EP application with the serial no. 10152394.2 filed 2. Feb. 2010 which are hereby incorporated by reference in their entirety.

All patent and non-patent references cited in the application, or in the present application, are also hereby incorporated by reference in their entirety.

FIELD OF INVENTION

The present invention is directed to the technical field of imaging compositions useful for diagnosing cancer and other diseases in a subject. In particular, the invention relates to a class of diagnostic compounds comprising a novel liposome composition with encapsulated radionuclides, such as copper isotopes, but not limited to, $^{61}$Cu and $^{64}$Cu. The invention further relates to a novel method for loading delivery systems, such as liposome compositions, with radionuclides comprising them and uses thereof in targeted diagnostic of a target site, such as cancerous tissue and, in general, pathological conditions associated with leaky blood vessels. The present invention provides a new diagnostic tool for the utilization of positron emission tomography (PET) imaging technique.

BACKGROUND OF INVENTION

Liposomes can serve as vesicles to deliver a wide range of encapsulated and/or membrane-incorporated therapeutic or diagnostic entities. Liposomes are usually characterized as nano-scale vesicles consisting of an interior core separated from the outer environment by a membrane of one or more bilayers. The bilayer membranes can be formed by amphiphilic molecules e.g. synthetic or natural lipids that comprise a hydrophobic and a hydrophilic domain [Lasic, Trends Biotechnol., 16: 307-321, 1998]. Bilayer membranes can also be formed by amphiphilic polymers constituting particles (e.g. polymersomes and polymerparticles).

Liposomes can serve as carriers of an entity such as, without limitation, a chemical compound, or a radionuclide, that is capable of having a useful property or provide a useful activity. For this purpose, the liposomes are prepared to contain the desired entity in a liposome-incorporated form. The liposome incorporated entity can be associated with the exterior surface of the liposome membrane, located in the interior core of the liposome or within the bilayer of the liposome. Methods for the incorporation of radionuclides into liposomes are e.g. surface labeling after liposome preparation [Phillips, Adv Drug Deliv Rev., 37: 13-32, 1999], label incorporation into the lipid bilayer of preformed liposomes [Morgan et al., J Med. Microbiol., 14: 213-217, 1981], surface labeling of preformed liposomes by incorporating lipid chelator conjugate during preparation [Goto et al., Chem harm Bull. (Tokyo), 37: 1351-1354, 1989; Seo et al., Bioconjucate Chem., 19: 2577-2584, 2008], and aqueous phase loading of preformed liposome [Hwang et al., Biochim Biophys Acta., 716: 101-109, 1982; Phillips et al., Int J Rad Appl Instrum B, 19: 539-547, 1992; Gabizon et al., J Liposome Res., 1: 123-125, 1988; Henriksen et al., Nucl Med. Bio., 31: 441-449, 2004]. The incorporation of entities into liposomes by the aqueous phase loading of preformed liposome is also referred to as "loading" and thereby "encapsulating" or "entrapping" the entities.

Encapsulating entities into the interior of liposomes through aqueous phase loading seem to have the greatest in vivo stability, because of the protected location of the entity inside the liposome. The purpose of encapsulating an entity into a liposome is often to protect the entity from the destructive environment and rapid excretion in vivo. The entrapment of the entity provides the opportunity for the encapsulated entity to apply the activity of the entity mostly at the site or in the environment where such activity is advantageous but less so at other sites where the activity may be useless or undesirable. It is known that liposomes having PEG chains attached to the outer surface have prolonged circulation time in the blood stream. These liposome compositions can effectively evade the immune system, which would otherwise attack the liposomes soon after injection causing fast clearance or rupture of the liposome and premature release of the agent entrapped inside. By increasing the blood circulation time, the agent entrapped in the liposome stays within the liposome until it reaches the target tissue. This phenomenon is referred to as passive targeting delivery, where an accumulation of long-circulating nanoparticles in tumor areas or inflammatory sites is due to leaky vasculature and lack of an effective lymphatic drainage system in these areas. For example, a radio-diagnostic entity entrapped within a long-circulating liposome can be delivered by passive targeting to a diseased site within a subject to facilitate a diagnosis thereof. Active- or ligand targeting delivery systems is referred to liposome compositions with ligands attached on the surface targeted against cell surface antigens or receptors [Allen, Science, 303: 1818-1822, 2004]. Combining the properties of targeted and long-circulating liposomes in one preparation comprising a radionuclide encapsulated liposome composition would significantly enhance the specificity and intensity of radioactivity localization in the target site e.g. a tumor.

Ideally, such liposome compositions can be prepared to include the desired entity, e.g. a chemical compound or radionuclide, (i) with a high loading efficiency, i.e., high percentage of encapsulated entity relative to the total amount of the entity used in the encapsulation process, and (ii) in a stable form, i.e., with minimal release (i.e. leakage) of the encapsulated entity upon storage or generally before the liposome reaches the site or the environment where the liposome entrapped entity is expected to apply its intended activity.

Entrapment of radionuclides such as copper isotopes into liposomes by the aqueous phase loading of preformed liposome can be obtained through use of chemical compounds called ionophores capable of transporting metal ions across lipid membranes. Upon crossing the membrane barrier the radionuclide then binds preferably to a chelator, encapsulated in the interior of the liposome composition, due to its stronger affinity thereto, allowing the release of free ionophore, and the entrapment of the radionuclide in the liposome composition.

Copper isotopes are of great interest for use in diagnostic and/or therapeutic application. For diagnostic applications this relates to the positron-emitters $^{61}$Cu and $^{64}$Cu which can be used in positron emission tomography (PET) diagnostic imaging. $^{64}$Cu is an interesting copper isotope possessing all decay modalities, and with a half-life of 12.7 h it is favorable for biological studies. A half-life of about 6-12 h appears to be ideal to allow for sufficient accumulation of liposome in inflammatory tissues or cancerous targets, yet providing enough background clearance to permit early identification of the target [Gabizon et al., Cancer Res., 50: 6371-6378]. Furthermore, $^{64}$Cu can be used as a model nuclide representing the chemical properties of all copper isotopes.

Ideal radioisotopes for therapeutic applications are those with low penetrating radiation, such as β-, α- and auger electron-emitters. Examples of such radioisotopes are $^{67}$Cu, $^{67}$Ga, $^{225}$Ac, $^{90}$Y, $^{177}$Lu and $^{119}$Sb. When the low energy emitting radioisotope in the form of a radiopharmaceutical reach the target site, the energy emitted is only deposited at the target site and nearby normal tissues are not irradiated. The energy of the emitted particles from the different radioisotopes and their ranges in tissues will vary, as well as their half-life, and the most appropriate radioisotope will be different depending on the application, the disease and the accessibility of the disease tissue.

Ideal radioisotopes for diagnostic applications are those with relatively short half-life, and those with high penetrating radiation to be detected by imaging techniques such as positron emission tomography (PET) and/or single photon emission computed tomography (SPECT). The half-life of the radionuclide must also be long enough to carry out the desired chemistry to synthesize the radiopharmaceutical and long enough to allow accumulation in the target tissue in the patient while allowing clearance through the non-target organs. The radionuclide, $^{64}$Cu, has proven to be a versatile isotope with respect to is applications in both imaging [Dehdashti et al., J Nucl Med. 38: 103P, 1997] and therapy [Anderson et al., J Nucl Med., 36: 2315-2325, 1998]. Radiopharmaceuticals and for example radiolabeled liposome compositions consisting of radionuclides, such as $^{61}$Cu ($T_{1/2}$=3.33 h) and $^{64}$Cu ($T_{1/2}$=12.7 h) can be utilized for imaging by the positron emission tomography (PET) technique, with the main advantages over single photon emission computed tomography (SPECT) being: a) employing annihilation coincidence detection (ACD) technique whereby only photons detected simultaneously (<10$^{-9}$ sec) by a pair of scintillators opposite each other are registered, instead of collimator, the sensitivity is markedly improved (×30-40) and the spatial resolution is enhanced by about a factor of two (<5 mm), since the detection field is (non-diverging) defined cylindrical volume and both the sensitivity and the resolution do not vary within the detection field [Kostarelos et al., Liposome Res., 9: 429-460, 1999]; b) PET scanners provide all images in the unit of radioactivity concentrations (e.g. Bq/ml) after corrections for photon attenuation, scatters and radoms, thereby considering PET to be a more quantitative technique than SPECT [Seo, Curr. Radiopharm., 1: 17-21, 2008].

Patent EP386 146 BI describes a composition and method of use for liposome encapsulated compounds for neutron capture tumor therapy. However, these liposomes were loaded with stable elements (e.g. boron), that become radioactive only after activation. The method in the invention lacks the utilization of ionophores and chelators.

WO/2001/060417 describes radiolabeled liposomes that are suitable for cancer therapy, loaded with heavy radionuclides (i.e., atomic weight over 150) emitting alpha particles, based on ionophoric loading using the calcium ionophore, A23187. From a diagnostic standpoint, this approach is not valuable, and the use of PET is not possible.

WO/2004/082627 and WO/2004/082626 describe liposomes with a radiolabeled complex encapsulated along with the pharmaceutical compositions useful for treating and/or detection of endometriotic implants or leaky blood vessels within the implant. The radioactive nuclide is complexed with one of the group consisting of oxine, ethylenediaminetetraacetic acid (EDTA) and diethylenetriaminepentaacetic acid (DTPA), and the radioactive nuclide is a positron-emitter or a gamma-emitter, the positron-emitter selected from the following, but not limited to, $^{11}$C, $^{18}$F, $^{76}$Br, $^{77}$Br and $^{89}$Zr, and the gamma-emitter selected from the following, but not limited to, $^{67}$Ga and $^{111}$In. However, these liposomes are not loaded with positron-emitters using ionophores other than oxine, and the pharmaceutical compositions are only directed toward treating and/or detecting endometriotic implants or leaky blood vessels within the implant.

US 20090081121 describes the loading of the radionuclides $^{111}$In, $^{177}$Lu, $^{90}$Y and $^{225}$Ac into liposome compositions using oxine as ionophore. The nuclide then binds preferably to diethylenetriaminepentaacetic acid (DTPA) or another chelator, encapsulated in the interior of the liposome, due to its stronger affinity therefore, allowing the release of free oxine, and the entrapment of the radionuclide. From a diagnostic standpoint, this approach is not useable for PET imaging applications, but only SPECT, because of the limited use of radionuclides.

WO/2006/095234 discloses a peptidomimetic moiety binding to integrin receptors which can be covalently linked to chelators which bind radionuclides such as $^{60}$Cu, $^{62}$Cu and $^{67}$Cu for various types of imaging. Methods for preparation of liposomes for MR-imaging which comprise chelated Tm and Gd are also mentioned. The method of preparation does not utilize ionophores.

In a theoretical study, Kostarelos et al., analyzed the therapeutic potential of liposomes labeled with one of the radionuclides $^{131}$I, $^{67}$Cu, $^{188}$Re or $^{211}$At, but chemical procedures for the preparation of the labeled liposomes were not suggested [Kostarelos et al., J Liposome Res, 9:407-424, 1999].

Only a few radiopharmaceuticals based on radioactive copper isotopes are discovered and available today. Examples are $^{60}$Cu-ATSM as hypoxia marker, and $^{64}$Cu-ATSM and $^{64}$Cu-PTSM, which are suggested as potential agents for tumor therapy. Further classes of substances are copper-labeled peptides and antibodies in which the radioactive copper is linked to the biomolecule via a bifunctional chelator. Yet no copper loaded liposome compositions are available.

Thus, there is a need in the technical field of diagnostic applications to provide various liposome compositions that are useful for delivery of a variety of compounds, such as, for example, radio-diagnostic and imaging entities useful for PET, such as, but not limited to, the radionuclide $^{61}$Cu. Therefore, the present invention provides a new method for loading preformed liposome compositions with radioactive copper isotopes or other radionuclides by using the chemical compound, carbostyril. The positron-emitter $^{64}$Cu is used as a model nuclide representing the chemical properties of all copper isotopes.

SUMMARY OF INVENTION

The present invention relates to liposome compositions that are useful in multifunctional and multimodality radionuclide delivery for imaging cancer or another disease, and/or for therapy.

A particular aspect of the invention provides a radionuclide encapsulated in a liposome consisting of a liposome composition having vesicle forming components, an agent-entrapping component enclosed by the vesicle forming component, and a radiolabeled agent entrapped within the liposome composition, wherein the radiolabeled agent comprises a copper radionuclide. In one embodiment of the invention the copper nuclides are Cu(II) cations. In another embodiment of the present invention, the copper nuclides are Cu(I) cations. In one embodiment of the invention, the described radionuclide further comprises one or more isotopes different from copper, which may or may not be radioactive. In one embodiment, the one or more isotopes different from copper are associated to the inner or outer surface of the nanoparticle composition via a linker molecule such as a chelator. In yet another embodiment, the one or more isotopes different from copper are enclosed within the interior of the nanoparticle composition.

In one embodiment of the invention, the described vesicle further comprises one or more isotopes different from copper, which may or may not be radioactive.

Another aspect of the present invention is further directed toward a method for preparing a radionuclide encapsulated in a liposome composition, wherein the liposome composition comprises a vesicle forming component, and an agent-entrapping component being a chelating-agent, a reducing component such as, but not limited to, ascorbic acid, glucose, fructose, glyceraldehyde, lactose, arabinose, maltose and acetol, or an agent that form low solubility salts with copper ions such as, but not limited to, phosphate, oxalate and chloride enclosed by the vesicle forming component. A radionuclide is entrapped within the liposome composition, wherein the radionuclide comprises a copper radionuclide.

Also encompassed by the present invention is a method for diagnosing and/or treating a cancer disease and, in general, pathological conditions associated with leaky blood vessels in a subject, in which a liposome composition is administered to a patient, said liposome composition having a vesicle forming component, and an agent-entrapping component enclosed by the vesicle forming component, wherein the radiolabeled agent comprises a radionuclide in the form of a copper isotope selected from the group, but not limited to, $^{61}$Cu, $^{64}$Cu and $^{67}$Cu. In one embodiment of the present, the radiolabeled agent comprises a radionuclide in the form of a copper isotope selected from the group consisting of $^{61}$Cu, $^{64}$Cu and $^{67}$Cu. In one embodiment of the method of the present invention, the described nanoparticle composition is administered intravenously. In another embodiment of the method of the present invention, the described nanoparticle composition is administered orally.

A particular important method of the invention is the preparation of liposome composition with encapsulated radionuclides. The entrapment of radionuclides is prepared by aqueous phase loading, using lipophilic chemical compounds, referred to as ionophores, capable of transporting metal entities over preformed liposome compositions and, in general, lipid membranes. The radionuclide then interacts with an agent-trapping component, and is encapsulated in the interior of the liposome composition, allowing the release of free ionophore, and the entrapment of the radionuclide in the liposome composition.

The present invention further encompass a method for preparing radiolabeled liposome compositions wherein the liposome composition further comprises a compound with intracellular nuclear targeting properties entrapped within the liposome composition. The compound with intracellular nuclear targeting properties comprises components selected from the group, but not limited to, a chelating-agent, an amino acid sequence and a radionuclide. In one embodiment, the compound is selected from the group consisting of a chelating-agent, an amino acid sequence and a radionuclide. The compound with intracellular targeting properties may be a nuclear localization sequence peptide (NLS peptide) which is conjugated to the agent-entrapping component and therefore entrapped within the nanoparticle composition.

One embodiment of the present invention or the method of the present invention further includes the step for monitoring the presence of the liposome composition in the target site in a subject by detecting the loaded liposome composition and/or labeled complex. The monitoring may be accomplished by positron emission tomography (PET) in cases where the radionuclide is a positron-emitter. In addition, monitoring may be accomplished by single photon emission computed tomography (SPECT) in cases where the radionuclide is a gamma-emitter.

A further embodiment of the invention provides a method for diagnosing and/or treating a cancer disease or another disease in a subject, wherein the nanoparticle comprises a radionuclide in the form of a copper isotope selected from the group, but not limited to, $^{61}$Cu, $^{64}$CU and $^{67}$Cu. In a preferred embodiment, the copper isotope is selected from the group consisting of $^{61}$Cu, $^{64}$Cu and $^{67}$Cu.

The invention also provides a method for diagnosing and/or treating a cancer disease, said method comprising administering a long-circulating liposome containing a radionuclide combined with an external moiety attached on the surface of the liposome composition, targeted for a tissue or cell in which neovascular or inflammatory site occurs, wherein the radionuclide is in the form of a copper isotope selected from the group, but not limited to, $^{61}$Cu, $^{64}$Cu and $^{67}$Cu. In a preferred embodiment of the invention, the radionuclide is in the form of a copper isotope selected from the group consisting of $^{61}$Cu, $^{64}$Cu and $^{67}$Cu.

Further provided is a method for preparing a drug delivery composition that includes the steps of: providing a liposome component having an external phospholipid layer and an internal phospholipid layer; attaching a moiety to the external layer which is targeted for neovascular, inflammatory site or leaky blood vessels to form a targeted liposome component; and combining the liposome component with a radiolabeled complex under suitable conditions for the complex to diffuse inside the liposome and become encapsulated therein.

It has been determined that the ionophore defined in formula A is generally capable of transporting a variety of metal radionuclides over vesicle membranes. Therefore, in another aspect of the present invention or the method of the present invention, wherein the ionophore used for transporting the radionuclides over the vesicle membrane is as defined in formula A (FIG. 2), including any preferred embodiments of A, the radionuclide loaded into the vesicles may be different from copper.

Additional aspects and advantages of the invention will be set forth in part in the description which follows, and in part will be apparent from the description, or can be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

FIG. 1 illustrates the structure of carbostyril (2-hydroxyquinoline, 2HQ) (A) and the general quinoline ($C_9H_7N$) (B). (C+D) exemplifies ionophores of the invention, but is not limited to, derivatives of carbostyril that can be used to load copper isotopes or other metal entities into liposomes. R can be, but is not limited to: H, F, Cl, Br, I, carbon chain ((C1-C24) saturated and unsaturated and with and without substituents other than H), OH, O—Z (where Z is a carbon chain (C1-C24) that can be saturated or unsaturated and with and without substituents other than H), S—H, S—Z, Se—H, Se—Z, NH2, NH—Z, N—Z—Z. X can be, but is not limited to: SH, SeH, O—Y (where Y is a carbon chain (C1-C8) that can be saturated or unsaturated and with and without substituents other than H), S—Y, Se—Y, NH2, NH—Y, N—Y—Y.

Figure 2:
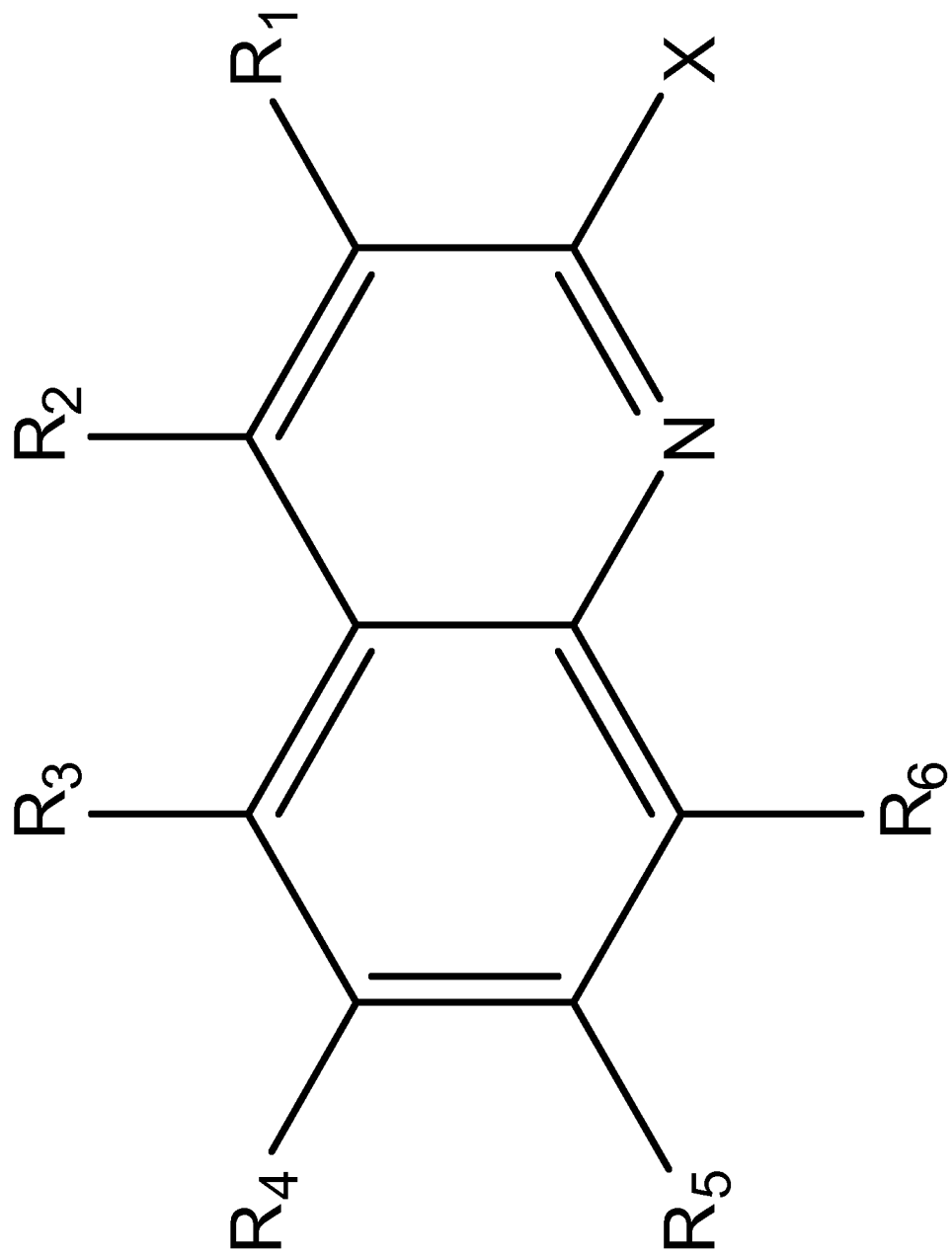

FIG. 2 illustrates the generalized structure of the 2-substituted ionophore of the present invention and the method of the present invention. In one preferred embodiment of the present invention or the method of the present invention, X is a hydroxy-group and $R_1$, $R_2$, $R_3$, $R_4$, $R_5$, and $R_6$ are all hydrogen atoms, and the compound is then named 2-hydroxyquinoline (carbostyril, 2HQ, specifically illustrated in FIG. 1A). However, in other embodiments, X is selected from the group consisting of hydroxy (OH), sulphydryl (SH) and amino ($NH_2$), and $R_1$, $R_2$, $R_3$, $R_4$, $R_5$, and $R_6$ independently of each other represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$). In one embodiment, $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

Figure 3:
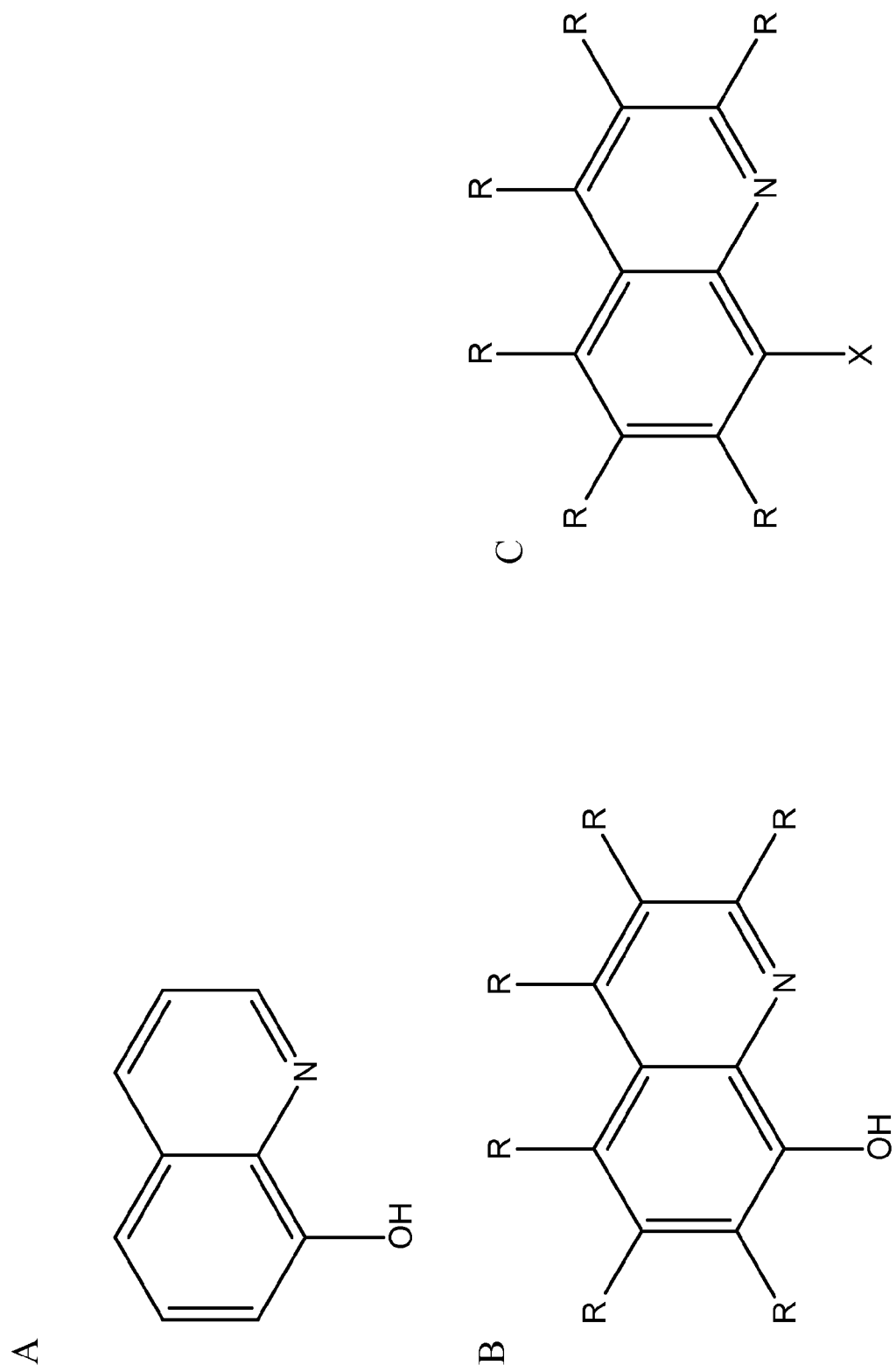

FIG. 3 illustrates the structure of oxine (8-hydroxyquinoline, 8HQ) (A). (B+C) exemplifies ionophores of the invention, but is not limited to, that can be used to load copper isotopes or other metal entities into liposomes. R can be, but is not limited to: H, F, Cl, Br, I, carbon chain ((C1-C24) saturated and unsaturated and with and without substituents other than H), OH, O—Z (where Z is a carbon chain (C1-C24) that can be saturated or unsaturated and with and without substituents other than H), S—H, S—Z, Se—H, Se—Z, NH2, NH—Z, N—Z2. X can be, but is not limited to: SH, SeH, O—Y (where Y is a carbon chain (C1-C8) that can be saturated or unsaturated and with and without substituents other than H), S—Y, Se—Y, NH2, NH—Y, N—Y2.

Figure 4:
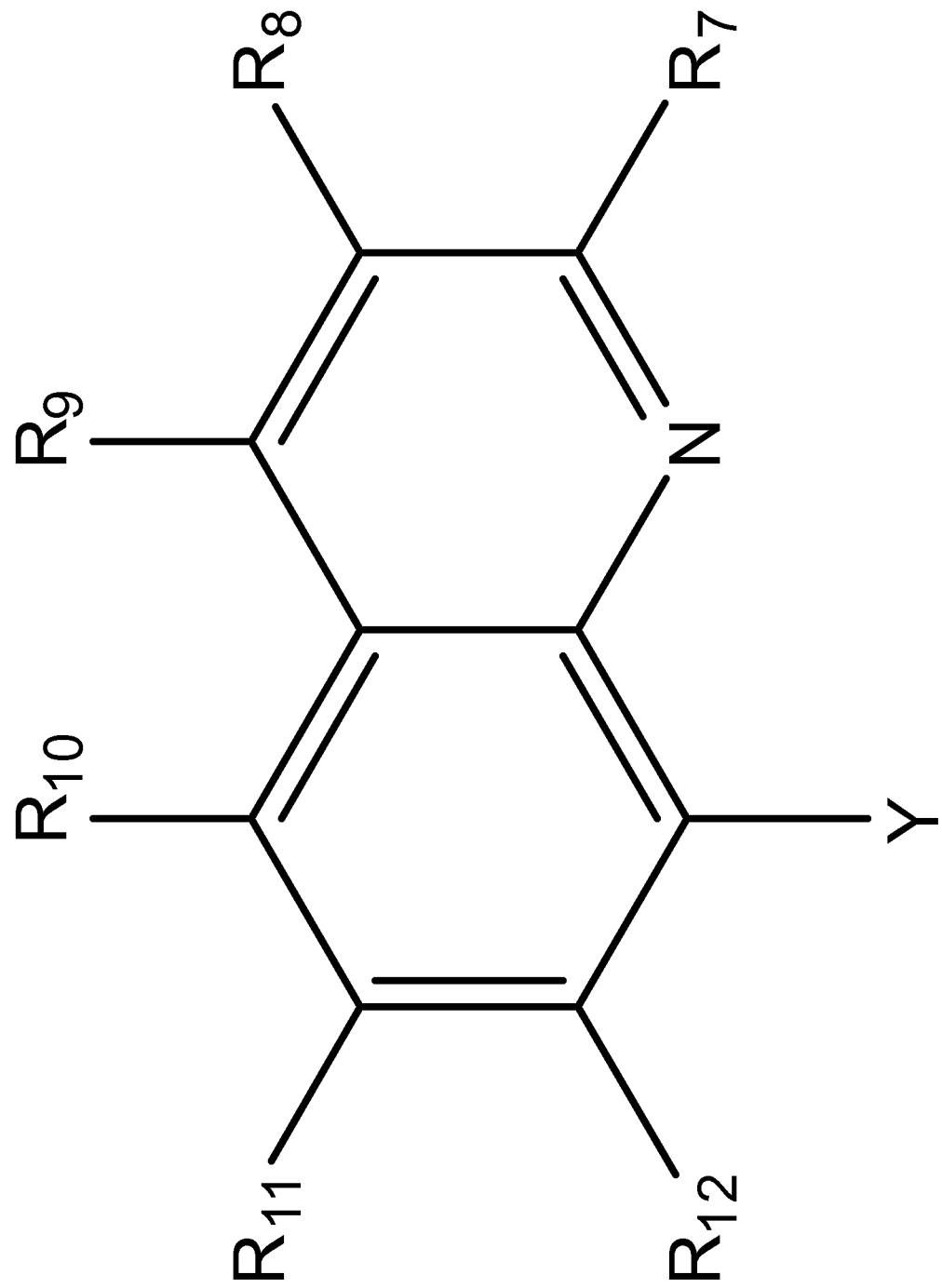

FIG. 4 illustrates the generalized structure of the 8-substituted ionophores of the present invention and the method of the present invention. In a preferred embodiment of the present invention or the method of the present invention, Y is a hydroxy-group and $R_7$, $R_8$, $R_9$, $R_{10}$, $R_{11}$, and $R_{12}$ are all hydrogen atoms, and the compound is then named 8-hydroxyquinoline (oxine, 8HQ, specifically illustrated in FIG. 3A). However, in further embodiments, Y is selected from the group consisting of hydroxy (OH), sulphydryl (SH) and amino ($NH_2$), and $R_7$, $R_8$, $R_9$, $R_{10}$, $R_{11}$, and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino ($N(CH_3)_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glucoronide ($C_6H_9O_7$), sulphonyl ($SO_3H$), benzoyl ($C_6H_4COOH$), and benzyl ($C_6H_5(CH_2)$). In one embodiment, $R_7$ and $R_8$, $R_8$ and $R_9$, $R_9$ and $R_{10}$, $R_{10}$ and $R_{11}$, or $R_{11}$ and $R_{12}$—together with the aromatic ring to which they are attached—may form a benzo-fused carbocyclic aromatic ring or an aliphatic ring.

Figure 5A:
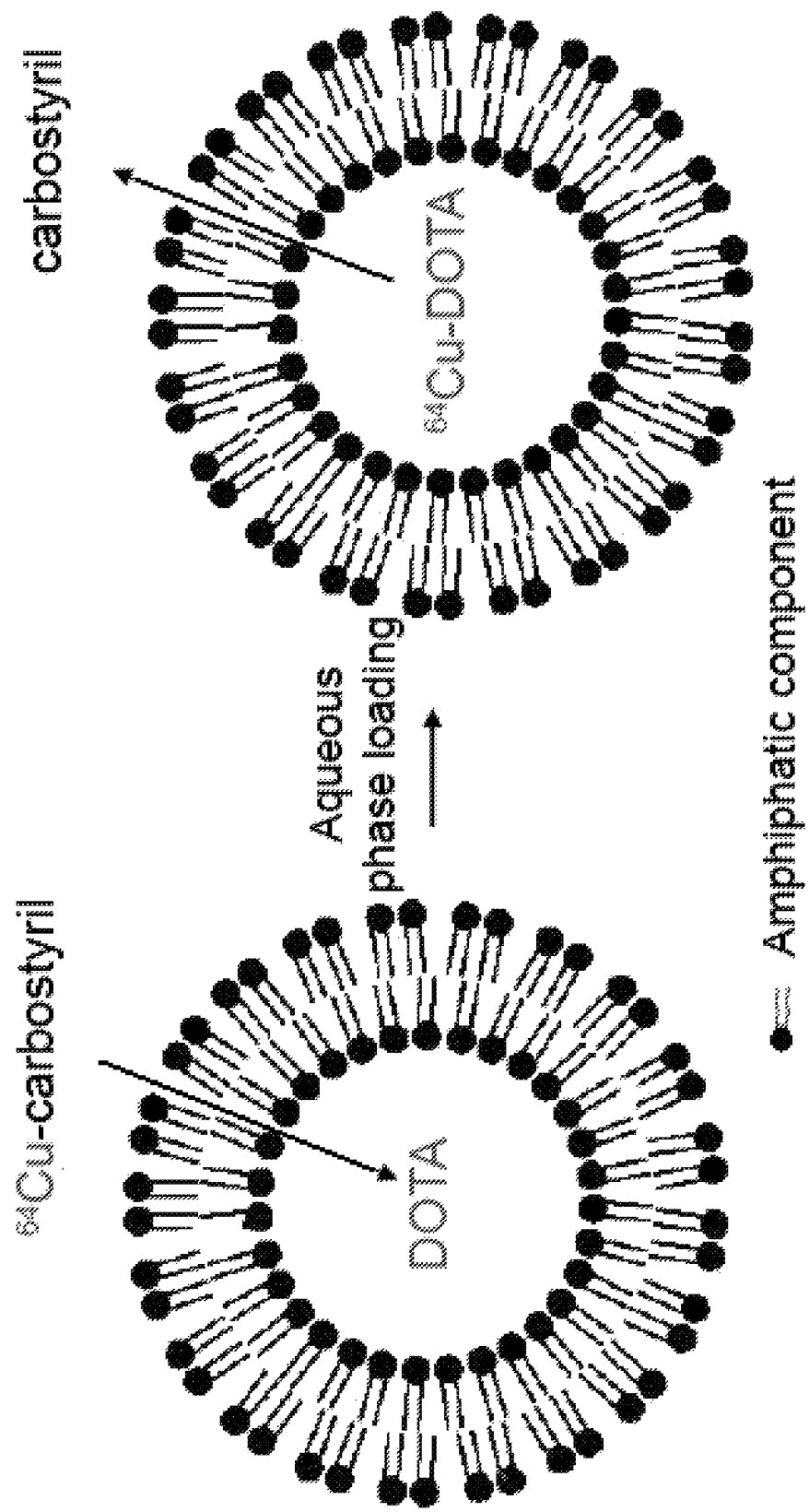
Figure 5B:
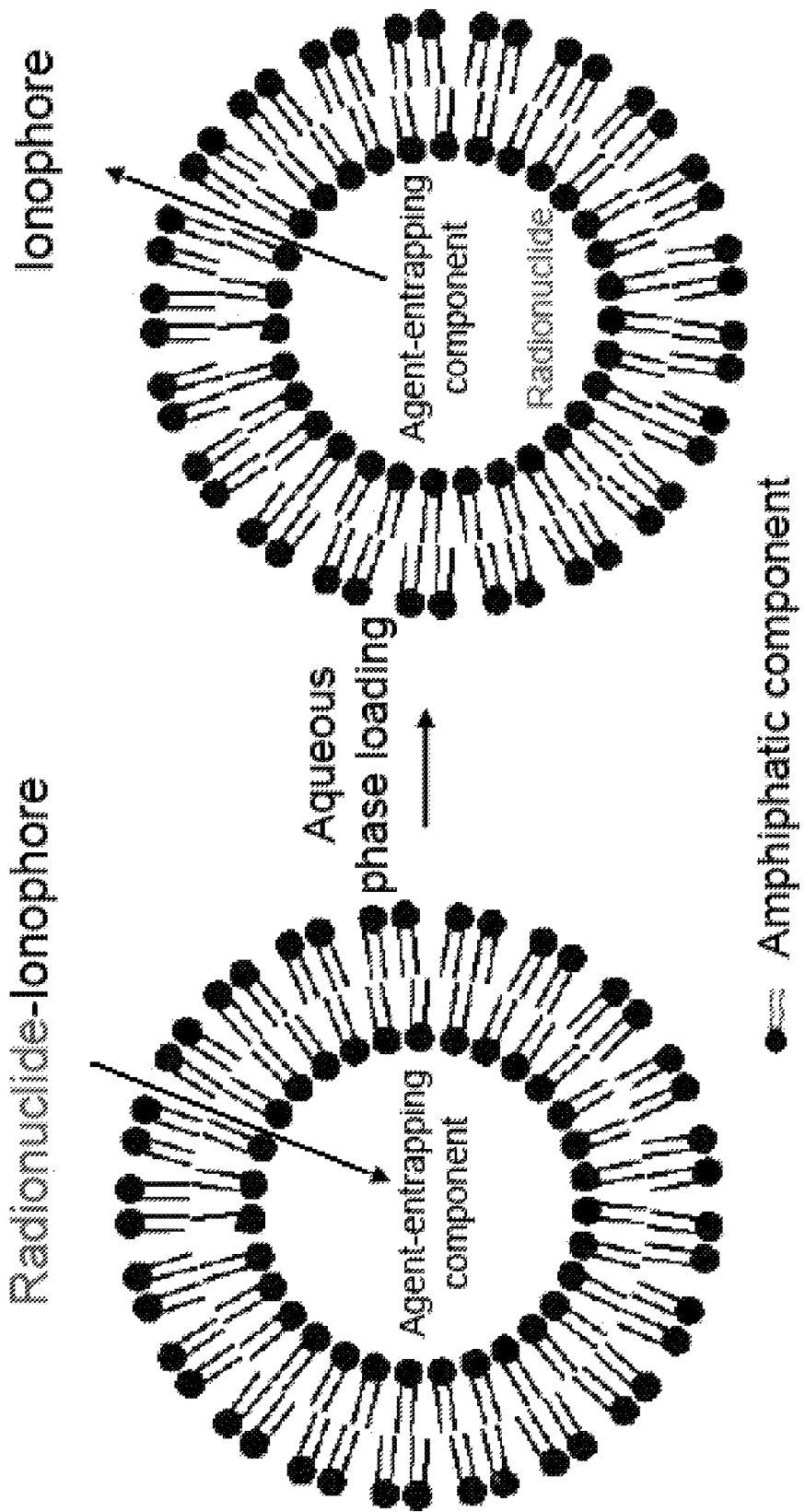

FIG. 5A illustrates the loading and encapsulation model of $^{64}$Cu-loaded liposome composition using the ionophore, carbostyril. The copper isotope loaded may be a Cu(II) cation or a Cu(I) cation. FIG. 5B illustrates the loading and encapsulation model of a radionuclide-loaded nanoparticle composition using an ionophore.

Figure 6A:
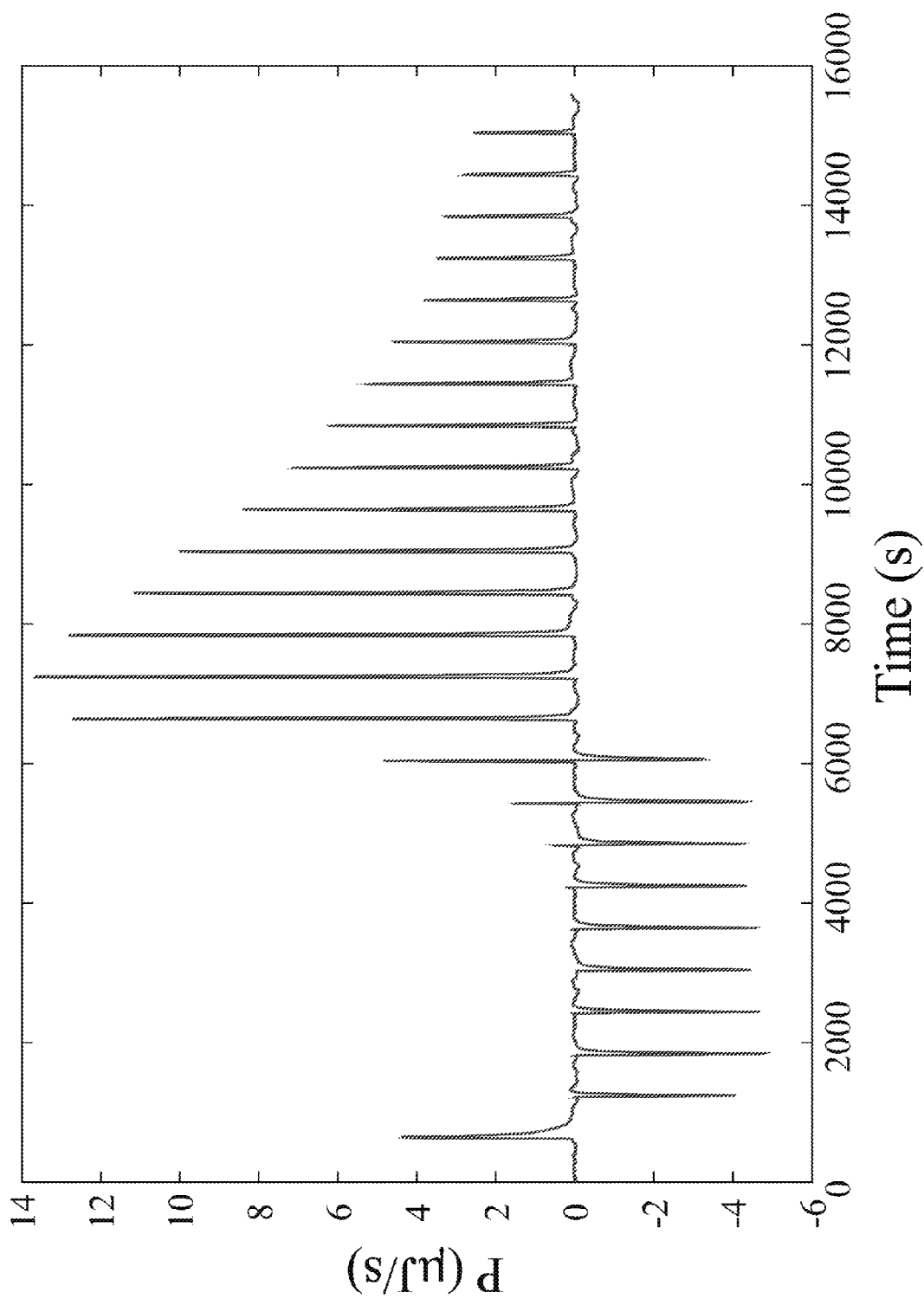
Figure 6B:
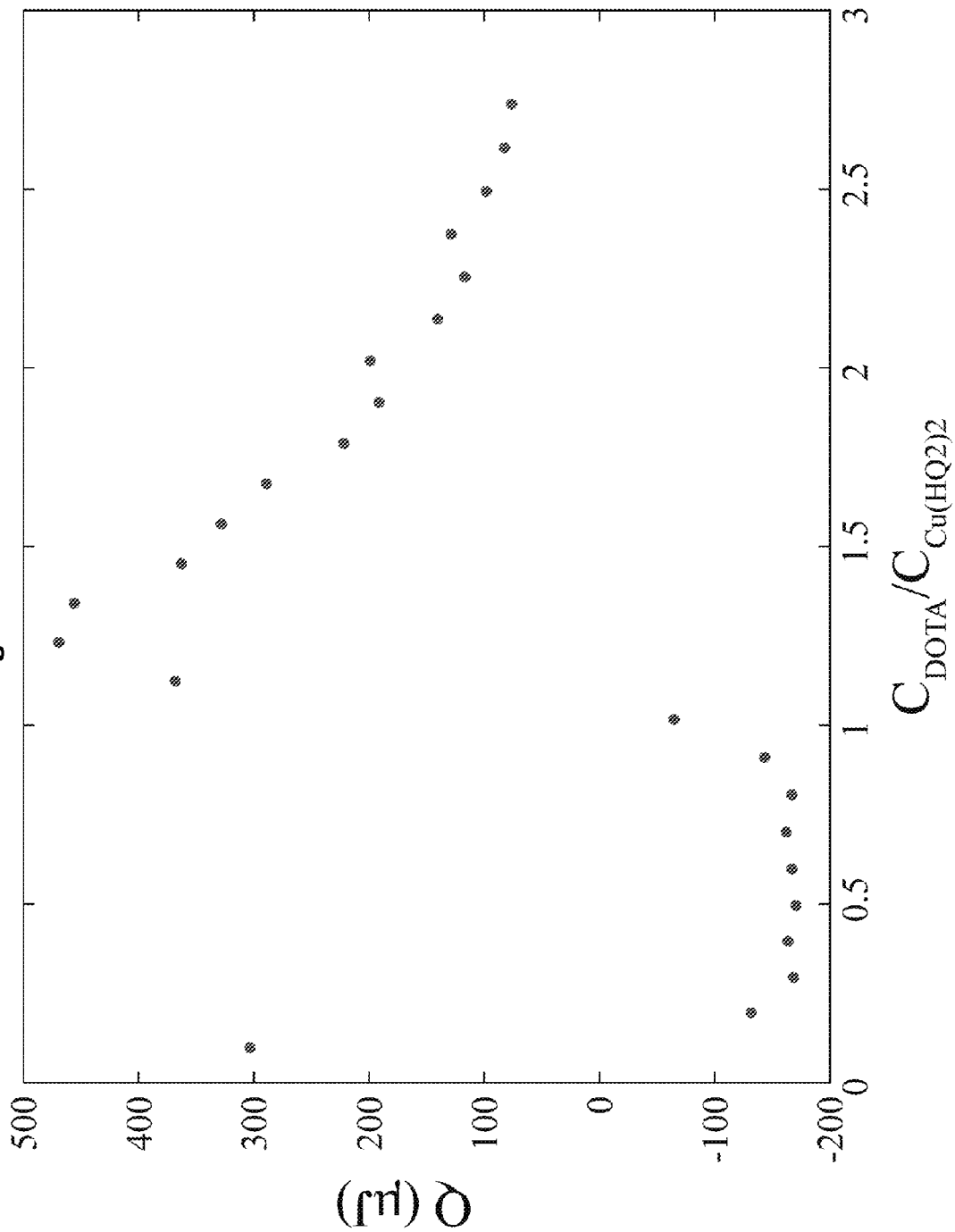

FIG. 6 illustrates the extraction of Cu(II) from 2-hydroxyquinoline by DOTA by isothermal titration calorimetry (ITC) analysis. The exchange of 2-hydroxyquinoline with DOTA are shown as heat spike plots (A) and integrated heat plots (B). Experimental conditions: 0.5 mM Cu(2-hydroxyquinoline)$_2$ is titrated with 10-μL injection of 5 mM DOTA. All solutions were prepared in Milli-Q water at pH=7.4.

FIG. 7 shows results of the encapsulation degree of $^{64}$Cu into preformed liposomes consisting of DSPC/Cholesterol/DSPE-PEG-2000 with DOTA pre-encapsulated when using carbostyril (A) and oxine (B) respectively, when analyzed with size exclusion chromatography (SEC) using a Sephadex G-50 column. In all cases, the interior pH of the liposomes was 4.0. The data of FIG. 7 and FIG. 10 is identical, only the software used in the analysis differs. Encapsulation efficiencies as high as 93% and 94%, respectively, were achieved.

FIG. 8 illustrates the in vitro stability of 100 nm sized $^{64}$Cu-Liposomes in solution (pH 7.4) at 37° C. after 24 hours of incubation. $^{64}$Cu-Liposomes are loaded with $^{64}$Cu using carbostyril (2-hydroxyquinoline, 2HQ) (A,C) and oxine (B,D) with an interior pH 4.0 (A,B) and pH 7.4 (C,D) in the liposomes.

Figure 9A:
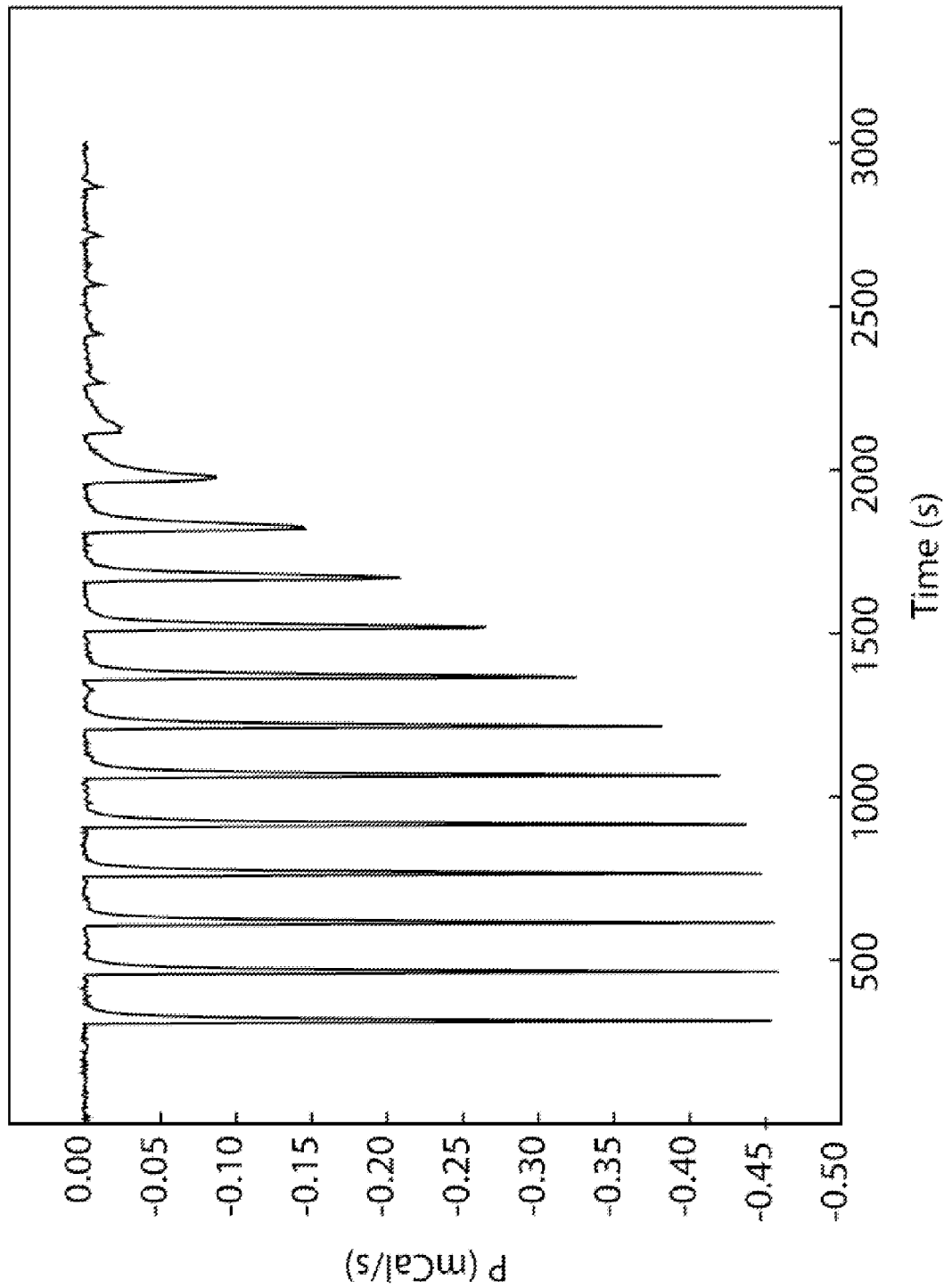
Figure 9B:
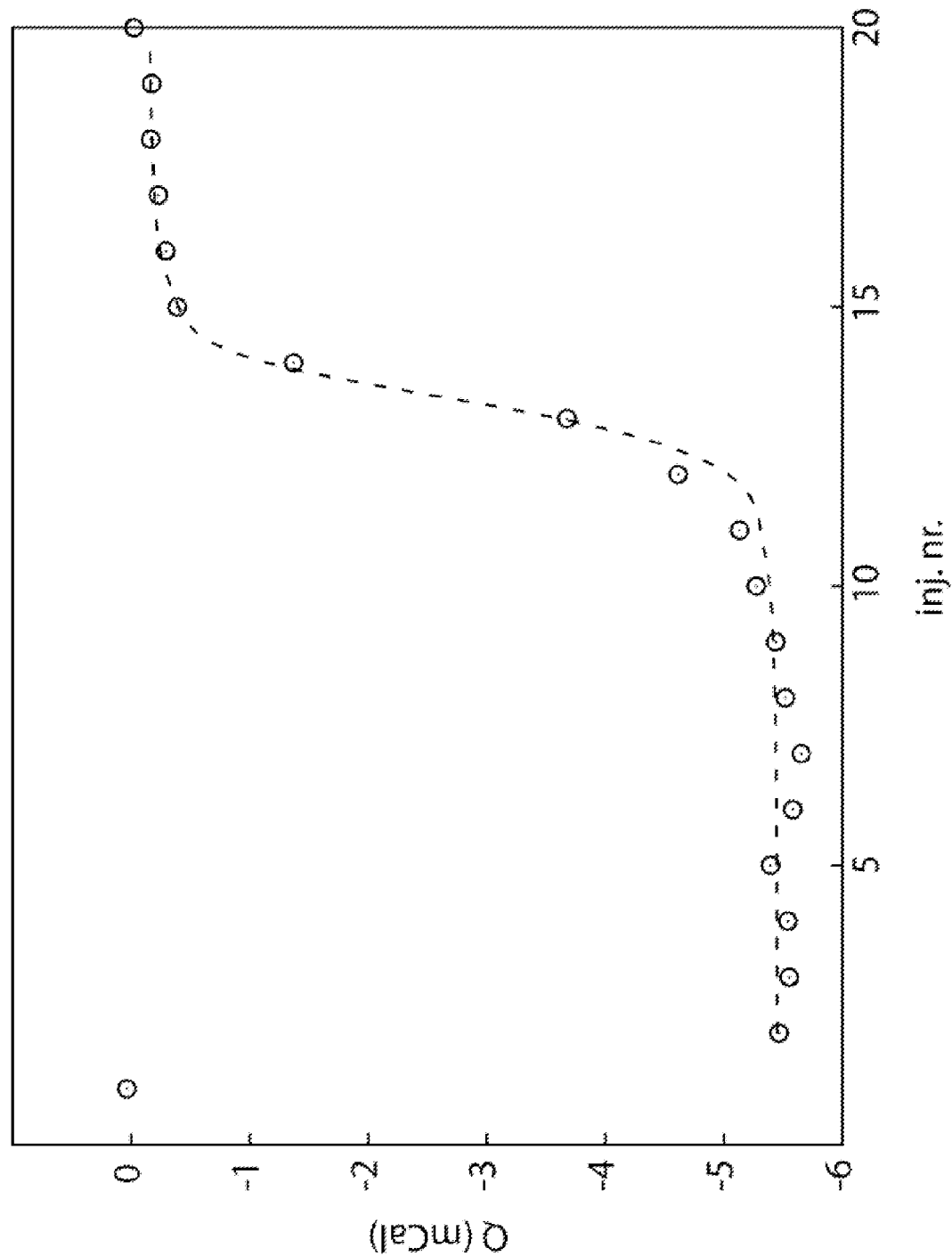

FIG. 9 illustrates the isothermal titration calorimetry (ITC) analysis of the extraction of Cu(II) from 2-hydroxyquinoline by DOTA. The exchange of 2-hydroxyquinoline with DOTA are shown as heat spike plots (A) and integrated heat plots (B). Experimental conditions: 0.5 mM Cu(2HQ)$_2$ is titrated with 2-μL injection of 5 mM DOTA. All solutions were prepared in MES buffer at pH=5.9.

FIG. 10 shows separation of $^{64}$Cu-Liposomes and free unentrapped $^{64}$Cu with size exclusion chromatography (SEC) using a Sephadex G-50 column. Preformed liposomes consisting of DSPC/Cholesterol/DSPE-PEG-2000 with DOTA pre-encapsulated were loaded with $^{64}$Cu using 2-hydroxyquinoline (2HQ) (A) or oxine (B), achieving encapsulation efficiencies as high as 93% and 94% respectively. In all cases, interior pH of the liposomes was 4.0. The data of FIG. 7 and FIG. 10 is identical, only the software used in the analysis differs.

Figure 11:
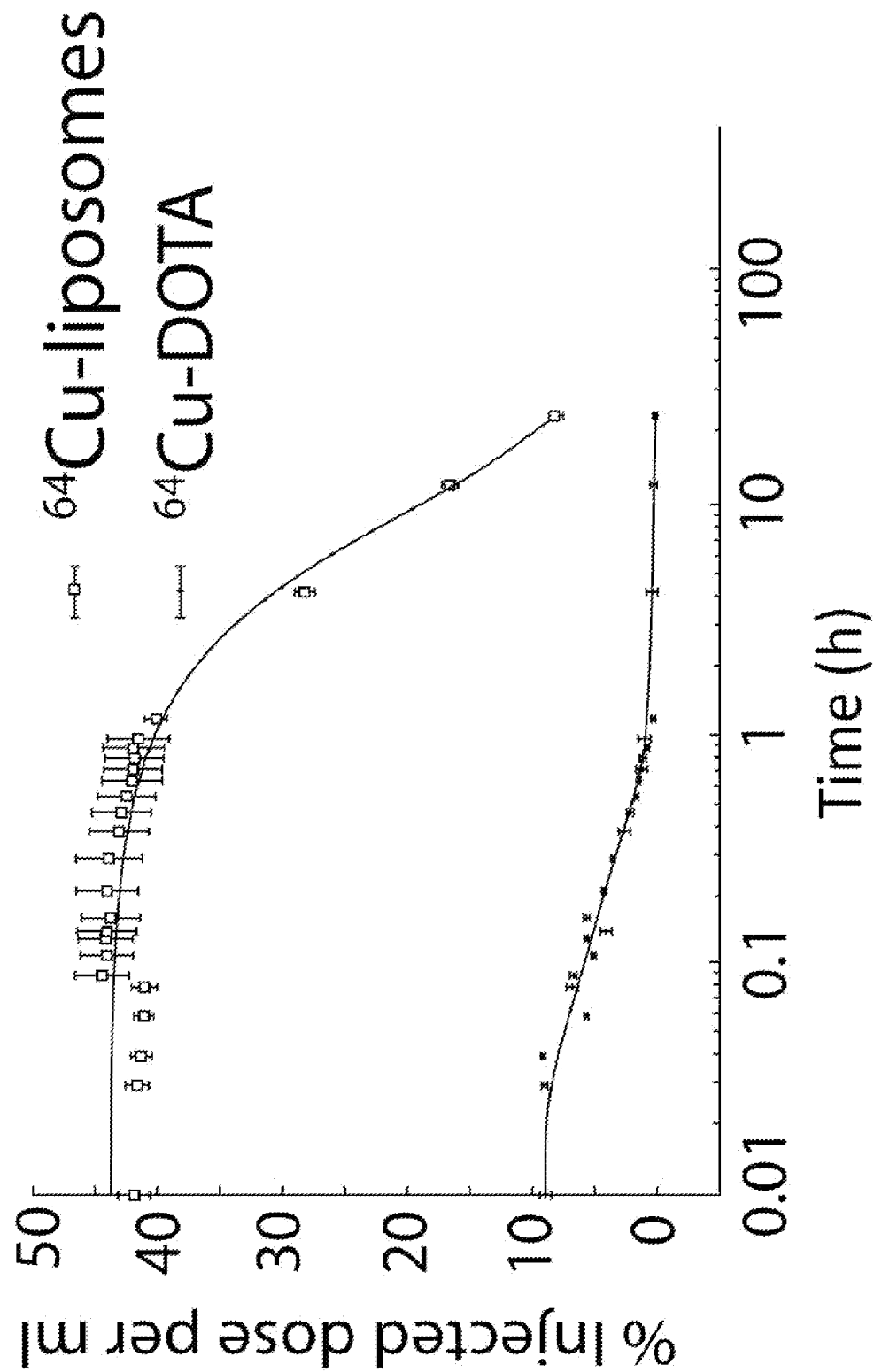

FIG. 11 is a time-activity curve (TAC) illustrating the blood concentration-time profile of $^{64}$Cu-liposome composed of (DSPC/CHOL/DSPE-PEG-2000) in the molar ratio 55:40:5 and $^{64}$Cu-DOTA in vivo in mice. The radioactivity concentrations are estimated from region of interests (ROIs) drawn around the left ventricle in the heart on axial PET/CT fusion images. The left ventricle is the most representative region in the heart of the blood concentration in the animals. The activities are expressed as percent injected dose per ml (% ID ml$^{-1}$) as function of time. All values are means±s.e.m (n=10).

Figure 12:
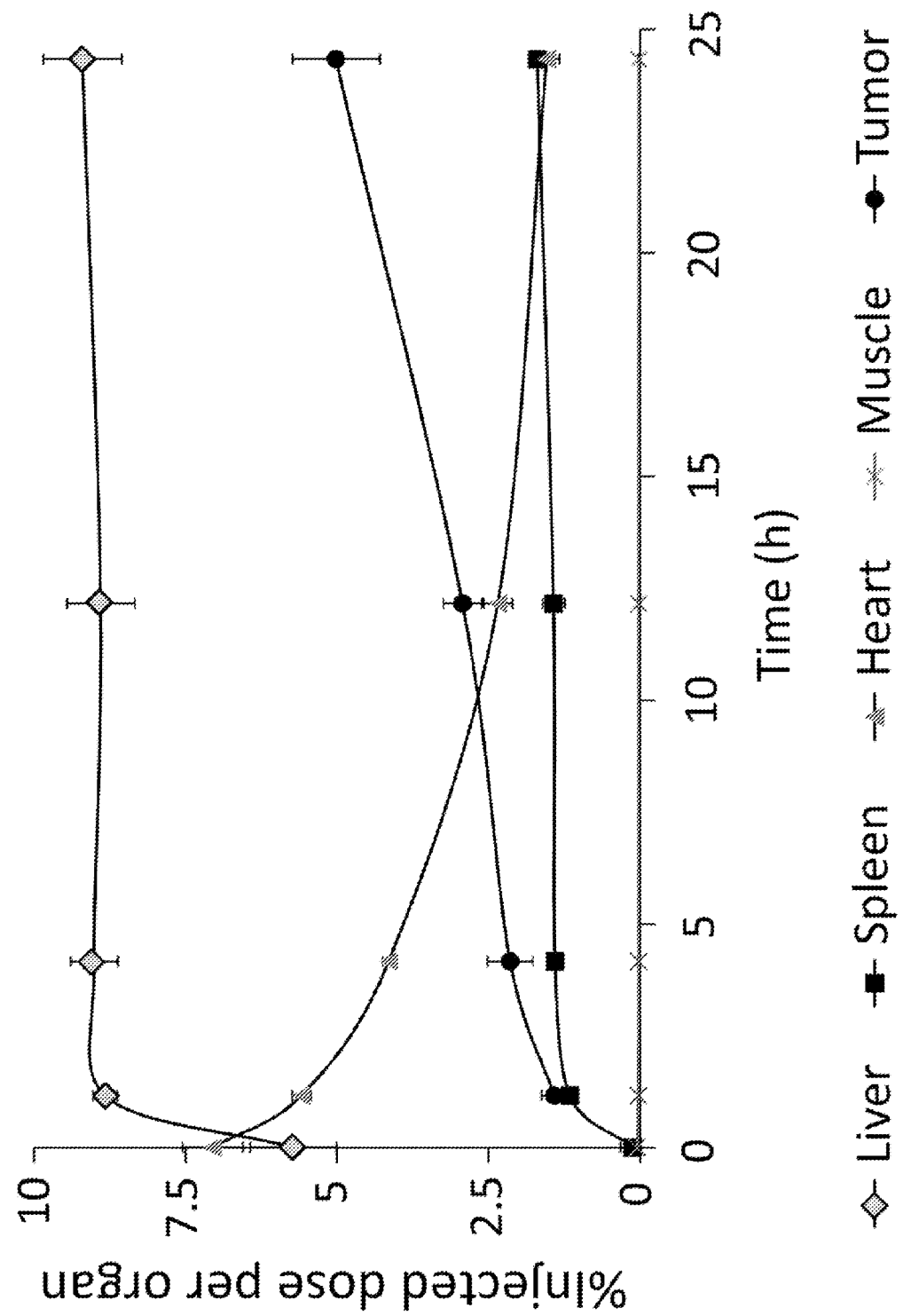

FIG. 12 is a time-activity curve (TAC) of the in vivo biodistribution of $^{64}$Cu-liposome composed of (DSPC/CHOL/DSPE-PEG-2000) in the molar ratio 55:40:5 within the liver, heart, spleen, muscle tissue and tumors expressed as percent injected dose per organ (% ID organ$^{-1}$) as function of time and calculated from region of interests (ROIs) image analysis. All values are means±s.e.m (n=10).

Figure 13A:
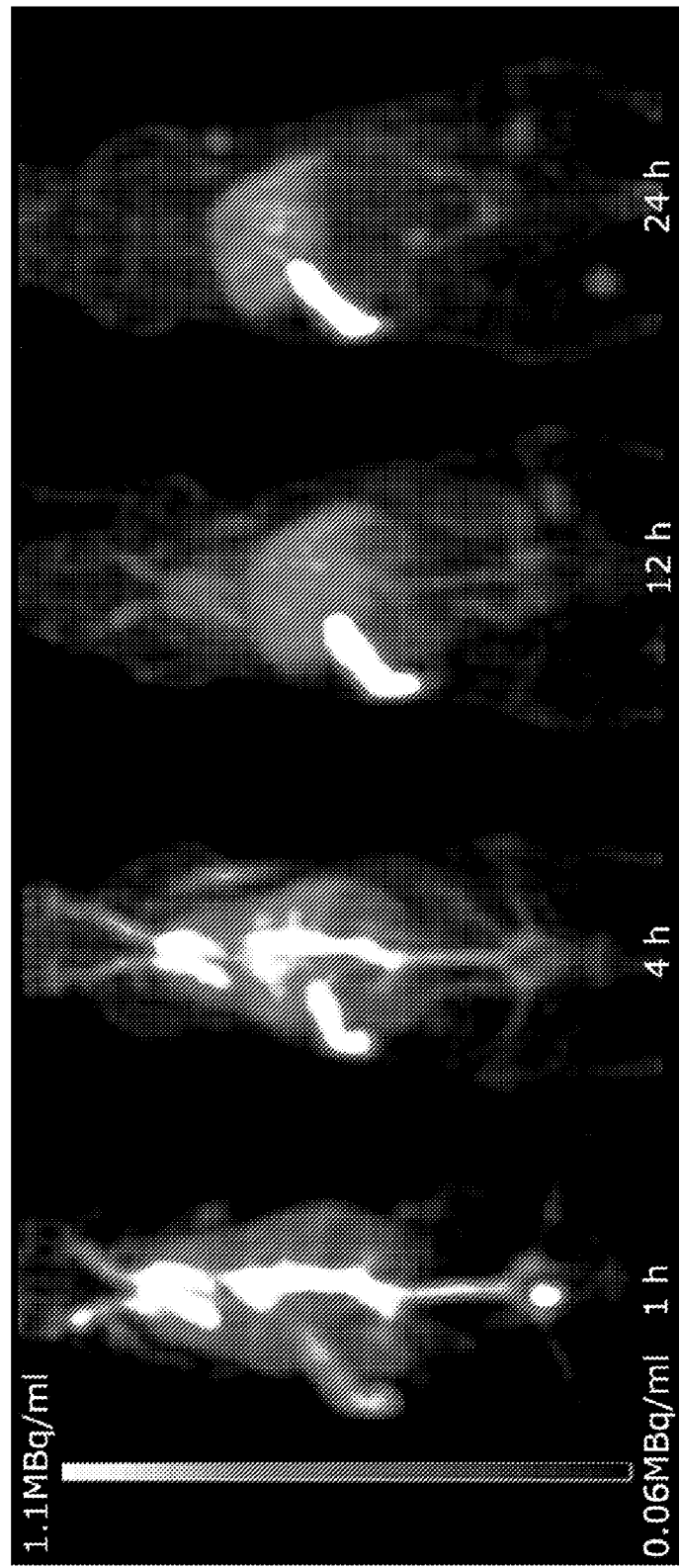
Figure 13B:
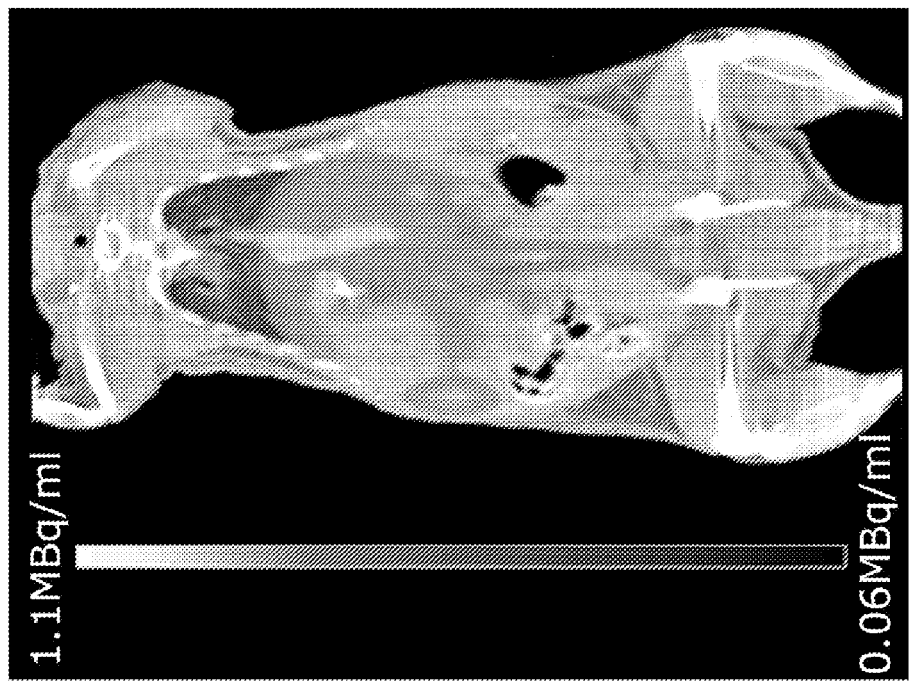

FIG. 13 shows positron emission tomography (PET)/computed tomography (CT)-images of $^{64}$Cu-liposomes distribution composed of (DSPC/CHOL/DSPE-PEG-2000) in the molar ratio 55:40:5 in normal and tumor-bearing mice. A, Coronal PET images 1, 4, 12 and 24 h after intravenous (i.v.) injection of $^{64}$Cu-liposomes into a normal mouse. B, Coronal PET/CT-fusion image 4 h after i.v. injection of $^{64}$Cu-liposomes into a normal mouse. C, Coronal PET image 24 h after i.v. injection of $^{64}$Cu-liposomes into a mouse bearing colon adenocarcinoma (HT29; marked with arrows) on right and left flank. D, Axial PET image (top) and axial PET/CT fusion (bottom) images 24 h after i.v. injection of $^{64}$Cu-liposomes into a mouse bearing colon adenocarcinoma (HT29; marked with arrows) on right and left flank.

FIG. 14 shows separation of $^{177}$Lu-liposomes and free unentrapped $^{177}$Lu with size exclusion chromatography (SEC) using a Sephadex G-50 column. Preformed liposomes consisting of DSPC/CHOL/DSPE-PEG$_{2000}$ with DOTA pre-encapsulated were loaded with $^{177}$Lu using 2-hydroxyquinoline (2HQ) achieving encapsulation efficiency as high as 96% (A). (B) illustrates the results from the storage stability test (24 h at 37° C.) where $^{177}$Lu-liposomes containing 10 mM DOTA at pH 4.0 retained more than 95% of the total radioactivity when $^{177}$Lu was loaded using 2HQ.

Figure 15:
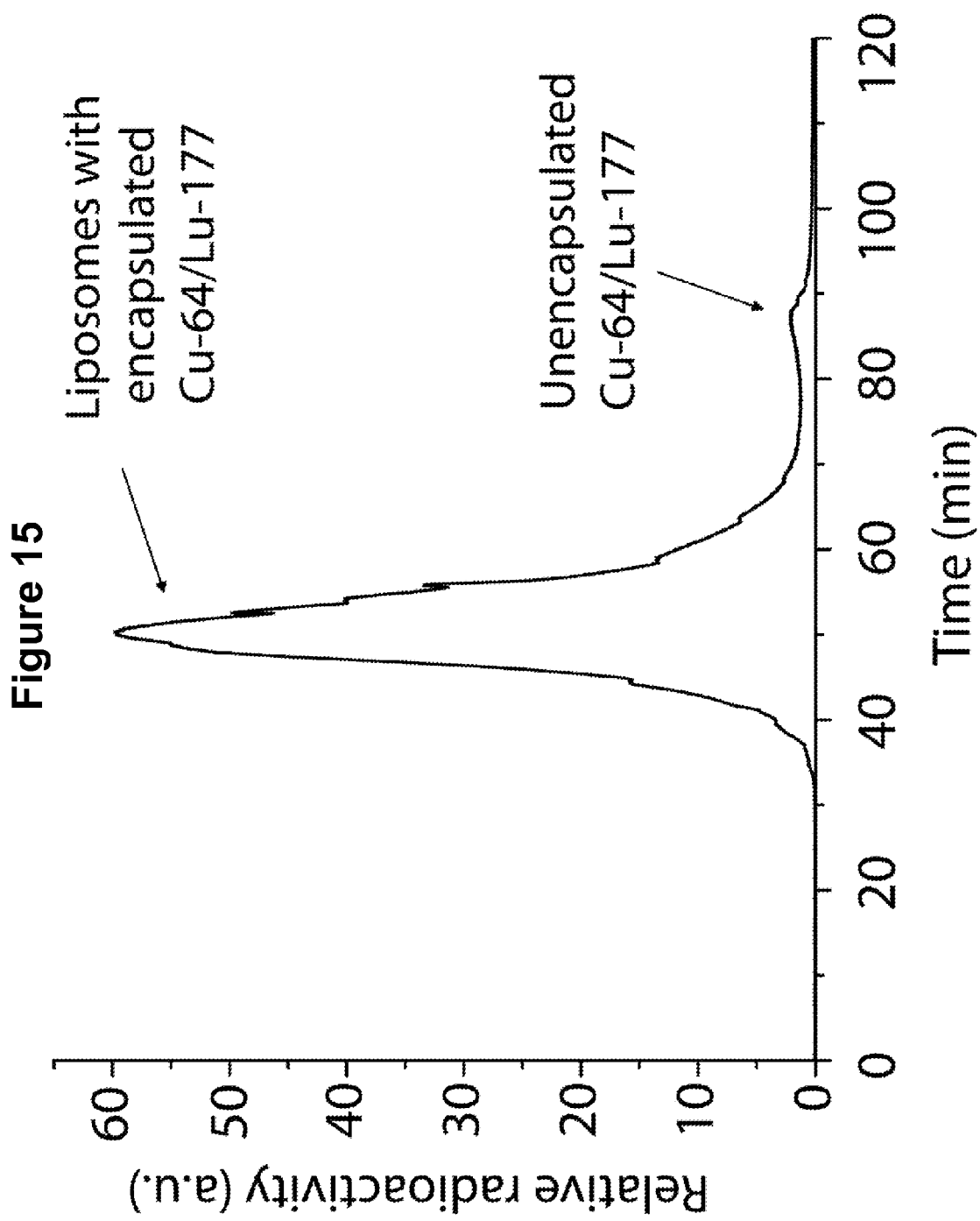

FIG. 15 shows separation of $^{64}$Cu/$^{177}$Lu-liposomes and free unentrapped $^{64}$Cu and $^{177}$Lu with size exclusion chromatography (SEC) using a Sephadex G-50 column. Preformed liposomes consisting of DSPC/CHOL/DSPE-PEG$_{2000}$ with DOTA pre-encapsulated were loaded with $^{64}$Cu and $^{177}$Lu using 2-hydroxyquinoline (2HQ) achieving encapsulation efficiency of 95% for $^{64}$Cu and 98% for $^{177}$Lu, illustrating that 2HQ efficiently loads $^{177}$Lu and $^{64}$Cu simultaneously into the interior of liposomes pre-encapsulated with DOTA.

DEFINITIONS

With the term "vesicle", as used herein, we refer to an entity which is characterized by the presence of an internal void. Preferred vesicles are formulated from lipids, including various amphiphatic components described herein.

In various aspects the term "nanoparticles", as used herein, are liposomes, polymerosomes or other lipid or polymer shell structures that constitute a membrane in its broadest term surrounding a hydrous core.

With the term "chelator" and "chelating-agent" as used herein interchangeably, we intend chemical moieties, agents, compounds, or molecules characterized by the presence of polar groups able to form a complex containing more than one coordinate bond with a transition metal or another entity.

With the term "metal entity" as used herein we intend a metal ion or a radionuclide, the latter used herein interchangeably with the term radioisotope.

With the term "phosphatide" we intend a phospholipid comprising a glycerol component.

With the term "amphiphatic" we intend a molecule which contains both polar and nonpolar regions.

With the term "binding affinity" and "affinity" as used herein interchangeably, we refer to the level of attraction between molecular entities. Affinity can be expressed quantitatively as a dissociation constant or its inverse, the association constant. In the context of this invention, as reported below, two types of affinities are considered: a) the affinity of an ionophore for example, but not limited to, carbostyril or oxine, for a transition metal ion or another metal entity, for example, Cu(II) or Cu(I) and b) the affinity of a chelator or another agent-entrapping component, for example, but not limited to, DOTA or another derivative thereof, for a transition metal ion or another metal entity, for example, Cu(II) or Cu(I).

With the term "ionophore" as used herein we refer to any compound, without limitation, capable of diffusing inside the liposome or over other bilayers. Furthermore, "ionophore" refers to any compound, without limitation, capable of forming a complex with a radionuclide or a metal entity, and hereafter transporting this complex across a bilayer.

With the term "entrapped agent" we intend a metal isotope, which may be a radionuclide or a non-radioactive isotope, entrapped within a liposome composition or a nanoparticle composition as herein described.

With the term "agent-entrapping" as used herein, we refer to any compound, without limitation, capable of trapping a metal ion or a radionuclide inside a liposome composition. Preferred agent-entrapping components are chelating-agents, substances that have the ability to reduce other substances, referred to a reducing agent, or substances that form low solubility salts with radionuclides or metal entities.

With the terms "loading", "encapsulation", or "entrapment" as used herein, is referred to an incorporation of radionuclides or metal entities into the interior of nanoparticle compositions.

With the terms "loading efficiency", "entrapment efficiency" or "encapsulation efficiency" as used herein interchangeably, is referred to the fraction of incorporation of radionuclides or metal entities into the interior of nanoparticle compositions expressed as a percentage of the total amount of radionuclide or metal entity used in the preparation.

With the term "encapsulation stability", "storage stability" or "serum stability" is referred to a stability test of the nanoparticle composition to measure the degree of leakage and/or release of the entrapped agent inside the nanoparticle composition.

With the term "radiolabeled complex" and the like, we refer to a chelating agent and a radionuclide that form a complex.

With the term "targeting moiety" as used herein we intend saccharides, oligosaccharides, vitamins, peptides, proteins, antibodies and affibodies and other receptor binding ligands characterized by being attached to the nanoparticle surface through a lipid or polymer component for delivering the nanoparticles to a higher degree to the target site or into target cells.

The terms "drug", "medicament", or "agent" as used herein include, biologically, physiologically, or pharmacologically active substances that act locally or systemically in the human or animal body.

The terms "treating", "treatment" and "therapy" as used herein refer equally to curative therapy, prophylactic or preventative therapy and ameliorating therapy. The term includes an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

DETAILED DESCRIPTION OF THE INVENTION

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The present invention relates to a novel method for preparation of radionuclides encapsulated within liposome compositions. Said liposome compositions are preferably in the form of nanoparticles.

The present invention solves a need in the technical field of diagnostic applications by providing a method for preparing liposome compositions for delivery of radioactive isotopes to cancerous tissue and, in general, to tissues with pathological conditions associated with leaky blood vessels such as inflammatory sites. Said liposome compositions are preferably in the form of nanoparticles.

According to the embodiments of the invention, the liposome composition is a micro-sized or a nano-sized particle that comprises a vesicle forming component and an agent-entrapping component. The vesicle forming components form an enclosed barrier of the particle. The agent-entrapping component has at least one chemical moiety that contains one or more negatively charged groups or is capable of trapping ions. The agent-entrapping component interacts with an encapsulated agent such as a radio-diagnostic or radio-therapeutic agent, by electrostatic interaction, to form a stable complex or low soluble salt, and substitutes the ionophore from the encapsulated agent, the ionophore being a compound such as carbostyril or other ionophores or compounds capable of transporting radionuclides across a bilayer, thus stabilizing and/or entrapping the encapsulated agent inside the vesicle. The stabilization of the encapsulated agent, such as the radio-diagnostic or radio-therapeutic agent, prevents or minimizes the release of the agent from the vesicles in the blood circulation.

In one embodiment, the nanoparticle of the present invention has a diameter of less than 120 nm.

In another embodiment, the nanoparticle composition of the present invention has a diameter of more than 80 nm.

In a preferred embodiment, the nanoparticle composition of the present invention has a diameter in the range of 30 nm to 300 nm; such as 30 nm to 60 nm, for example 60 nm to 80 nm, such as 80 nm to 100 nm, for example 100 nm to 120 nm, such as 120 nm to 150 nm, such as 150 nm to 180 nm, such as 180 nm to 210 nm, for example, 210 nm to 240 nm, such as 240 nm to 270 nm for example 270 nm to 300 nm.

In one embodiment of the present invention, a method for preparing a radiolabeled liposome is provided. The method includes, but is not limited to, a vesicle forming component, a component for transporting ions over membranes and an agent-entrapping component enclosed by the vesicle forming component. A radiolabeled agent is trapped within the liposome composition, said radiolabeled agent comprising one or more radionuclides, such as a copper isotope, such as $^{61}Cu$, $^{64}Cu$ and $^{67}Cu$. The copper isotopes used in the present invention may be in the form of Cu(II) cations or Cu(I) cations.

In a further embodiment of the invention, a method for diagnosing, treating and/or monitoring a cancerous disease such as a solid tumor or another disease in a subject is provided. The method includes providing a liposome composition having a vesicle forming component, an agent-entrapping component, a component for transporting ions over membranes, and a radiolabeled agent comprising one or more radionuclides, such as a copper isotope, but not limited to, $^{61}Cu$, $^{64}Cu$ and $^{67}Cu$. The copper isotopes may be Cu(II) cations or Cu(I) cations. The liposome composition is then administered to a subject by, for example, intravenous administration followed by measuring the amount of radiation emitted from the radionuclide within the liposome composition after a given incubation time.

The present inventors have determined that the ionophore defined in formula A is generally capable of transporting a variety of metal radionuclides over vesicle membranes. Therefore, in another aspect of the present invention or the method of the present invention, wherein the ionophore used for transporting said radionuclides over the vesicle membrane is as defined in formula A, including any preferred embodiments of A, the entrapped agent is one or more isotopes of one or more metal radionuclides.

Preferably, the entrapped isotopes of metal radionuclides are selected from the group consisting of Copper ($^{61}Cu$, $^{64}Cu$, and $^{67}Cu$), Indium ($^{111}In$), Technetium ($^{99m}Tc$), Rhenium ($^{188}Re$), Gallium ($^{67}Ga$, $^{68}Ga$), Lutetium ($^{177}Lu$), Actinium ($^{225}Ac$), Yttrium ($^{90}Y$), Antimony ($^{119}Sb$), Tin ($^{117}Sn$, $^{113}Sn$), Dysprosium ($^{159}Dy$), Cobalt ($^{56}Co$), Iron ($^{59}Fe$), Ruthenium ($^{97}Ru$, $^{103}Ru$), Palladium ($^{103}Pd$), Cadmium ($^{115}Cd$), Tellurium ($^{118}Te$, $^{123}Te$), Barium ($^{131}Ba$, $^{140}Ba$), Gadolinium ($^{149}Gd$, $^{151}Gd$), Terbium ($^{160}Tb$), Gold ($^{198}Au$, $^{199}Au$), Lanthanum ($^{140}La$), and Radium ($^{223}Ra$, $^{224}Ra$), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations. For this aspect, the nanoparticles, including vesicle forming components, agent-entrapping components, targeting moieties, size and pH characteristics as well as any uses of the nanoparticles may be as described herein below.

In another preferred embodiment, the entrapped isotopes are Rhenium $^{186}Re$), Strontium ($^{89}Sr$), Samarium ($^{153}Sm$), Ytterbium ($^{169}Yb$), Thallium ($^{201}Tl$), Astatine ($^{211}At$), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations. For this aspect, the nanoparticles, including vesicle forming components, agent-entrapping components, targeting moieties, size and pH characteristics as well as any uses of the nanoparticles may be as described herein below In another preferred embodiment of this aspect of the present invention or the method of the present invention, the ionophore used for transporting said radionuclides over the vesicle membrane is carbostyril (2-hydroxyquinoline).

In yet another embodiment, the entrapped isotope of a metal radionuclide is selected from the group consisting of Copper ($^{61}Cu$, $^{64}Cu$, and $^{67}Cu$), Indium ($^{111}In$), Technetium ($^{99m}Tc$), Rhenium ($^{188}Re$), Gallium ($^{67}Ga$, $^{68}Ga$), Actinium ($^{225}Ac$), Yttrium ($^{90}Y$), Antimony ($^{119}Sb$) and Lutetium ($^{177}Lu$), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations.

Combinations of radionuclides are useful for simultaneous monitoring/imaging and treatment of various diseases such as cancer, and/or for monitoring by use of several different imaging methods. Radionuclides and combinations of radionuclides may emit one or more types of radiation such as alpha particles, beta+ particles, beta− particles, auger electrons or gamma-rays. Combinations of radionuclides may further allow for one or more types of imaging and/or radiation therapy. Thus, in another embodiment, this invention relates to vesicles and methods for their preparation, wherein the vesicles comprise two or more radionuclides, selected from the group of Copper ($^{61}$Cu, $^{64}$Cu, and $^{67}$Cu), Indium ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), ($^{131}$Ba, $^{140}$Ba), ($^{149}$Gd, $^{151}$Gd), Terbium ($^{160}$Tb), Gold ($^{198}$Au, $^{199}$Au), Lanthanum ($^{140}$La), and Radium ($^{223}$Ra, $^{224}$Ra), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations. For this aspect, the nanoparticles, including vesicle forming components, agent-entrapping components, targeting moieties, size and pH characteristics as well as any uses of the nanoparticles may be as described herein below. Vesicles according to the present invention may comprise a combination of one or more radionuclides for imaging and one or more radionuclides for therapy. Radionuclides for imaging comprise radionuclides such as $^{64}$Cu, $^{61}$Cu, $^{99m}$Tc, $^{68}$Ga, $^{89}$Zr and $^{111}$In.

Radionuclides for therapy comprise radionuclides such as $^{64}$Cu, $^{67}$Cu, $^{111}$In, $^{67}$Ga, $^{186}$Re, $^{188}$Re, $^{89}$Sr, $^{153}$Sm, $^{169}$Yb, $^{201}$Tl, $^{211}$At, $^{177}$Lu, $^{225}$Ac, $^{90}$Y, $^{119}$Sb, $^{117}$Sn, $^{113}$Sn, $^{159}$Dy, $^{56}$Co, $^{59}$Fe, $^{97}$Ru, $^{103}$Ru, $^{103}$Pd, $^{115}$Cd, $^{118}$Te, $^{123}$Te, $^{131}$Be, $^{140}$Ba, $^{149}$Gd, $^{151}$Gd, $^{160}$Tb, $^{198}$Au, $^{199}$Au, $^{140}$La, $^{223}$Ra and $^{224}$Ra.

A preferred embodiment of the present invention relates to vesicles and methods for their preparation, wherein the vesicles comprise two or more radionuclides selected $^{61}$Cu, $^{64}$Cu, $^{67}$Cu, $^{67}$Ga, $^{68}$Ga, $^{225}$Ac, $^{90}$Y, $^{177}$Lu, $^{186}$Re, from the group of $^{188}$Re and $^{119}$Sb.

An even more preferred embodiment of the present invention relates to vesicles and methods for their preparation wherein the vesicles comprises $^{64}$Cu and $^{177}$Lu, or $^{64}$Cu and $^{67}$Cu, or $^{61}$Cu and $^{67}$Cu, or $^{64}$Cu and $^{90}$Y, or $^{64}$Cu and $^{119}$Sb, or $^{64}$Cu and $^{225}$Ac, or $^{64}$Cu and $^{188}$Re, or $^{64}$Cu and $^{186}$Re, or $^{64}$Cu and $^{211}$At, or $^{64}$Cu and $^{67}$Ga, or $^{61}$Cu and $^{177}$Lu, or $^{61}$Cu and $^{90}$Y, or $^{61}$Cu and $^{119}$Sb, or $^{61}$Cu and $^{225}$Ac, or $^{61}$Cu and $^{188}$Re, or $^{61}$Cu and $^{186}$Re, or $^{61}$Cu and $^{211}$At, or $^{61}$Cu and $^{67}$Ga, or $^{67}$Cu and $^{177}$Lu, or $^{67}$Cu and $^{90}$Y, or $^{67}$Cu and $^{119}$Sb, or $^{67}$Cu and $^{225}$Ac, or $^{67}$Cu and $^{188}$Re, or $^{67}$Cu and $^{186}$Re, or $^{67}$Cu and $^{211}$At, or $^{68}$Ga and $^{177}$Lu, or $^{68}$Ga and $^{90}$Y, or $^{68}$Ga and $^{119}$Sb, or $^{68}$Ga and $^{225}$Ac, or $^{68}$Ga and $^{188}$Re, or $^{68}$Ga and $^{186}$Re, or $^{68}$Ga and $^{211}$At, or $^{68}$Ga and $^{67}$Cu.

Vesicles comprising one or more radionuclides according to the present invention may be used for clinical imaging and/or radiotherapy. Clinical imaging includes imaging for diagnosis, monitoring the effects of treatment, or monitoring the location of vesicles used for radiotherapy.

The vesicles according to the present invention may be used for one or more types of imaging. Such imaging includes, but is not limited to, x-ray imaging, computed tomography (CT) imaging, magnetic resonance imaging (MRI), positron emission tomography (PET) imaging, single photon emission computed tomography (SPECT) imaging or nuclear scintigraphy imaging.

In a preferred embodiment, vesicles of the present invention comprise a combination of radionuclides useful for combined positron emission tomography (PET) imaging and radiation therapy, such as $^{64}$Cu and $^{177}$Lu, or such as $^{64}$Cu and $^{67}$Cu, or such as $^{61}$Cu and $^{67}$Cu, or such as $^{64}$Cu and $^{90}$Y, or such as $^{64}$Cu and $^{119}$Sb, or such as $^{64}$Cu and $^{225}$Ac, or such as $^{64}$Cu and $^{188}$Re, or such as $^{64}$Cu and $^{186}$Re, or such as $^{64}$Cu and $^{211}$At.

In an even more preferred embodiment, vesicles of the present invention comprise a combination of radionuclides useful for combined positron emission tomography (PET) imaging and radiation therapy, such as $^{64}$Cu and $^{177}$Lu.

According to the present invention, the nanoparticles may comprise one or more isotopes different from copper which may be associated to the inner or outer surface of the nanoparticle composition via a linker molecule such as a chelator. Such isotopes may be selected from the group of Indium, ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), Radium ($^{223}$Ra, $^{224}$Ra), Rhenium ($^{186}$Re), Strontium ($^{89}$Sr), Samarium ($^{153}$Sm), Ytterbium ($^{169}$Yb), Thallium ($^{201}$Tl) and Astatine ($^{211}$At), wherein said isotope of a metal radionuclide may appear in any of the existing oxidation states for the metal. These oxidation states include monovalent cations, divalent cations, trivalent cations, tetravalent cations, pentavalent cations, hexavalent cations and heptavalent cations. For this aspect, the nanoparticles, including vesicle forming components, agent-entrapping components, targeting moieties, size and pH characteristics as well as any uses of the nanoparticles may be as described herein below.

In a further embodiment of the invention, the radionuclide may also be entrapped within another carrier such as a nanoparticle that is useful in diagnosing and/or treating a cancerous disease and, in general a pathological condition associated with leaky blood vessels or another disease in a subject.

A detailed description of exemplary vesicle forming components, agent-entrapping components, and ionophores for preparing the liposome compositions of the present invention are set forth below.

Vesicle Forming Component:

A vesicle forming component is a synthetic or naturally-occurring amphiphatic compound which comprises a hydrophilic part and a hydrophobic part. Vesicle forming components include, for example, fatty acids, neutral fats, phosphatides, glycolipids, aliphatic alcohols, and steroids.

The vesicle forming component of the present invention or the method of the present invention may contain a hydrophilic polymer such as, but not limited to, a polyethylene glycol (PEG) component or a derivate thereof or a polysaccharide. In such a case the vesicle forming component is said to be derivatized with the hydrophilic polymer (e.g. PEG) or the polysaccharide. In one embodiment, the polymer enables conjugation of proteins or other receptor affinity molecules to the vesicle forming component derivatized with the polymer. In another embodiment, the attachment of the polymer (e.g. PEG) to the liposome composition, allows for prolonged circulation time within the blood stream. Vesicles comprising PEG chains on their surface are capable of extravasating leaky blood vessels.

Examples of suitable vesicle forming lipids used in the present invention or the method of the present invention include, but are not limited to: phosphatidylcholines such as 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2-palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine; phosphatidylethanolamines such as 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoyl-phosphatidylethanolamine; phosphatidylserines such as 1,2-dioleoyl-phosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl-2-oleoyl-phosphatidylserine and 1-stearoyl-2-oleoyl-phosphatidylserine; phosphatidylglycerols such as 1,2-dioleoyl-phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl-2-oleoyl-phosphatidylglycerol and 1-stearoyl-2-oleoyl-phosphatidylglycerol; pegylated lipids; pegylated phosphoholipids such as phosphatidylethanolamine-N-[methoxy(polyethyleneglycol)-1000], phosphatidylethanolamine-N-[methoxy(polyethyleneglycol)-2000], phosphatidylethanolamine-N-[methoxy(polyethylene glycol)-3000], phosphatidylethanolamine-N-[methoxy(polyethyleneglycol)-5000]; pegylated ceramides such as N-octanoyl-sphingosine-1-{succinyl[methoxy(polyethyleneglycol)1000]}, N-octanoyl-sphingosine-1-{succinyl[methoxy(polyethylene glycol)2000]}, N-octanoyl-sphingosine-1-{succinyl[methoxy(polyethyleneglycol)3000]}, N-octanoyl-sphingosine-1-{succinyl[methoxy(polyethyleneglycol)5000]}; lyso-phosphatidylcholines, lyso-phosphatidylethanolamines, lyso-phosphatidylglycerols, lyso-phosphatidylserines, ceramides; sphingolipids; glycolipids such as ganglioside GMI; glucolipids; sulphatides; phosphatidic acid, such as di-palmitoyl-glycerophosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; polyoxyethylene fatty acids esters and polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; di-oleoyl-sn-glycerol; dipalmitoyl-succinylglycerol; 1,3-dipalmitoyl-2-succinylglycerol; 1-alkyl-2-acyl-phosphatidylcholines such as 1-hexadecyl-2-palmitoyl-phosphatidylcholine; 1-alkyl-2-acyl-phosphatidylethanolamines such as 1-hexadecyl-2-palmitoyl-phosphatidylethanolamine; 1-alkyl-2-acyl-phosphatidylserines such as 1-hexadecyl-2-palmitoyl-phosphatidylserine; 1-alkyl-2-acyl-phosphatidylglycerols such a s 1-hexadecyl-2-palmitoyl-phosphatidylglycerol; 1-alkyl-2-alkyl-phosphatidylcholines such as 1-hexadecyl-2-hexadecyl-phosphatidylcholine; 1-alkyl-2-alkyl-phosphatidylethanolamines such as 1-hexadecyl-2-hexadecyl-phosphatidylethanolamine; 1-alkyl-2-alkyl-phosphatidylserines such as 1-hexadecyl-2-hexadecyl-phosphatidylserine; 1-alkyl-2-alkyl-phosphatidylglycerols such as 1-hexadecyl-2-hexadecyl-phosphatidylglycerol; N-Succinyl-dioctadecylamine; palmitoylhomocysteine; lauryltrimethylammonium bromide; cetyltrimethyl-ammonium bromide; myristyltrimethylammonium bromide; N-[1,2,3-dioleoyloxy)-propyl]-N,N,Ntrimethylammoniumchloride (DOTMA); 1,2-dioleoyloxy-3 (trimethylammonium)propane(DOTAP); and 1,2-dioleoyl-c-(4'-trimethylammonium)-butanoyl-sn-glycerol (DOTB).

In one embodiment the vesicle forming component include compounds selected from the group of DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]), POP C (1-palmitoyl-2-oleoyl-sn-glycero-3-phosphocholine), DPPC (1,2-dipalmitoyl-sn-glycero-3-phosphocholine), DSPE-PEG$_{2000}$-TATE, (1,2-distearoyl-sn-glycero-3-phosphoethanolamine-N-[methoxy (polyethylene glycol)-2000]-TATE).

In one embodiment of the nanoparticle composition, the vesicle forming component consists of amphiphatic compounds selected from the group consisting of 1,2-distearoyl-sn-glycero-3-phosphocholine (DSPC), cholesterol, and 1,2-distearoyl-sn-glycero-3-phosphoethanolamine-N-[methoxy (polyethylene glycol)-2000] (DSPE-PEG-2000) in the molar ratio of 55:40:5.

In another embodiment of the nanoparticle composition, the vesicle forming component consists of amphiphatic compounds selected from the group consisting of 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C" in the molar ratio of A:B:C, wherein A is selected from the interval 45 to 65, B is selected from the interval 35 to 45, and C is selected from the interval 2 to 8 and wherein A+B+C=100.

In one embodiment of the disclosed method, the vesicle forming component consists of amphiphatic compounds selected from the group consisting of 1,2-distearoyl-sn-glycero-3-phosphocholine (DSPC), cholesterol, and 1,2-distearoyl-sn-glycero-3-phosphoethanolamine-N-[methoxy (polyethylene glycol)-2000] (DSPE-PEG-2000) in the molar ratio of 55:40:5.

In another embodiment of the disclosed method, the vesicle forming component consists of amphiphatic compounds selected from the group consisting of 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C" with the molar ratio A:B:C, wherein A is selected from the interval 45 to 65, B is selected from the interval 35 to 45, and C is selected from the interval 2 to 8 and wherein A+B+C=100.

In a preferred embodiment the vesicle forming component include DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]) in a molar ratio of 50:40:10.

In another preferred embodiment the vesicle forming component include DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]) in a molar ratio of 55:40:5.

In another embodiment of the disclosed method, the vesicle forming component consists of amphiphatic compounds selected from the group consisting of 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000)

"C", and 1,2-distearoyl-sn-glycero-3-phosphoethanolamine-N-[methoxy (polyethylene glycol)-2000]-TATE (DSPE-PEG-2000-TATE) "D" with the molar ratio A:B:C:D, wherein A is selected from the interval 45 to 65, B is selected from the interval 35 to 45, C is selected from the interval 5 to 13, D is selected from the interval 0 to 3, and wherein A+B+C+D=100.

In a preferred embodiment the vesicle forming component include DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]) and 1,2-distearoyl-sn-glycero-3-phosphoethanolamine-N-[methoxy (polyethylene glycol)-2000]-TATE (DSPE-PEG-2000-TATE) in a molar ratio of 50:40:9:1.

The vesicle forming component may further comprise a lipid-conjugate of an antibody or an affibody or a peptide that acts as a targeting moiety to enable the nanoparticle to specifically bind to target cell bearing a target molecule.

The vesicle forming component may also consist of a lipid-conjugate of an antibody or an affibody or a peptide that acts as a targeting moiety to enable the nanoparticle to specifically bind to diseased target.

The antibodies useful in the present invention may be monospecific, bispecific, trispecific, or of greater multi-specificity. For example, multi-specific antibodies may be specific for different epitopes of a cytokine, cell, or enzyme which may be present in an increased amount at the target site compared to the normal tissues.

An "antibody" in accordance with the present specification is defined as a protein that binds specifically to an epitope. The antibody may be polyclonal or monoclonal. Examples of monoclonal antibodies useful in the present invention is selected from the group consisting of, but not limited to, Rituximab, Trastuzumab, Cetuximab, LymphoCide, Vitaxin, Lym-1 and Bevacizumab. In a preferred embodiment, the monoclonal antibodies are selected from the group consisting of Rituximab, Trastuzumab, Cetuximab, LymphoCide, Vitaxin, Lym-1, and Bevacizumab.

An "affibody" is defined as a small and stable antigen-binding molecule that can be engineered to bind specifically to a large number of target proteins. The affibody molecules mimic monoclonal antibodies in many ways, and in addition offer several unique properties making them a superior choice for a number of applications. These applications include incorporating the affibodies as lipid-conjugates in liposome compositions targeted for a tissue or a cell in a neovascular or inflammatory site, wherein the radionuclide, such as a copper isotope, but not limited to, $^{61}$Cu, $^{64}$Cu and $^{67}$Cu, is included for diagnostic and/or therapeutic applications. Examples of affibody molecules useful in the present invention is collected for the group consisting of, but not limited to, anti-ErbB2 affibody molecule and anti-Fibrinogen affibody molecule.

The peptides useful in the present invention act as a targeting moiety to enable the nanoparticle to specifically bind to a diseased target, wherein the peptides are selected from the group consisting of, but not limited to, RGD, somatostatin and analogs thereof, and cell-penetrating peptides. In one embodiment, the peptides are selected from the group consisting of RGD, somatostatin and analogs thereof, and cell-penetrating peptides. In one embodiment, the somatostatin analog is octreotate (TATE).

The vesicle forming components are selected to achieve a specified degree of fluidity or rigidity, to control the stability of the liposome compositions in vivo and to control the rate of release of the entrapped agent inside the liposome composition. The rigidity of the liposome composition, as determined by the vesicle forming components, may also play a role in the fusion or endocytosis of the liposome to a targeted cell.

Agent-entrapping Component:

The agent-entrapping component of the present invention or the method of the present invention can be a chelating agent that forms a chelating complex with the transition metal or the radiolabeled agent, such as the radionuclide. Examples of chelators include, but are not limited to, 1,4,7,10-tetraazacyclododecane-1,4,7,10-tetraacetic acid (DOTA) and derivative thereof; 1,4,8,11-tetraazacyclotetradecane (cyclam) and derivative thereof; 1,4,7,10-tetraazacyclododecane (cyclen) and derivative thereof; 1,4-ethano-1,4,8,11-tetraazacyclotetradecane (et-cyclam) and derivative thereof; 1,4,7,11-tetraazacyclotetradecane (isocyclam) and derivative thereof; 1,4,7,10-tetraazacyclotridecane ([13]aneN$_4$) and derivative thereof; 1,4,7,10-tetraazacyclododecane-1,7-diacetic acid (DO2A) and derivative thereof; 1,4,7,10-tetraazacyclododecane-1,4,7-triacetic acid (DO3A) and derivative thereof; 1,4,7,10-tetraazacyclododecane-1,7-di(methanephosphonic acid) (DO2P) and derivative thereof; 1,4,7,10-tetraazacyclododecane-1,4,7-tri(methanephosphonic acid) (DO3P) and derivative thereof; 1,4,7,10-tetraazacyclododecane-1,4,7,10-tetra(methanephosphonic acid) (DOTP) and derivative thereof; ethylenediaminetetraacetic acid (EDTA) and derivative thereof; diethylenetriaminepentaacetic acid (DTPA) and derivative thereof; 1,4,8,11-tetraazacyclotetradecane-1,4,8,11-tetraacetic acid (TETA) and derivative thereof, or other adamanzanes and derivates thereof.

The agent-entrapping component of the present invention or the method of the present invention can also be a substance that has the ability to reduce other substances, thus referred to as a reducing agent. Examples of reducing agents include, but are not limited to, ascorbic acid, glucose, fructose, glyceraldehyde, lactose, arabinose, maltose and acetol. In one embodiment of the present invention the loaded copper isotope, which may be Cu(II) or Cu(I) cations, is reduced to a lower oxidation state upon diffusion through the vesicle membrane, thus trapping the copper isotope within the vesicle. In another embodiment, the radionuclide different from copper, is reduced to a lower oxidation state upon diffusion through the vesicle membrane, thus trapping the radionuclide different from copper within the vesicle.

An agent-entrapping component within the scope of the present invention or the method of present invention may also be a substance with which the radionuclide or metal entity, such as copper isotope, forms a low solubility salt. Examples of such are copper phosphates, copper oxalate and copper chlorides. In one embodiment, the low solubility salt formed with copper (Cu(II) or Cu(I)) is selected from the group consisting of copper phosphates, copper oxalate and copper chlorides.

In one embodiment of the present invention or the method of the present invention the agent-entrapping component is a chelator selected from the group consisting of macrocyclic compounds comprising adamanzanes; 1,4,7,10-tetraazacyclododecane ([12]aneN$_4$) or a derivative thereof; 1,4,7,10-tetraazacyclotridecane ([13]aneN$_4$) or a derivative thereof; 1,4,8,11-tetraazacyclotetradecane ([14]aneN$_4$) or a derivative thereof; 1,4,8,12-tetraazacyclopentadecane ([15]aneN$_4$) or a derivative thereof; 1,5,9,13-tetraazacyclohexadecane ([16]aneN$_4$) or a derivative thereof; and other chelators capable of binding metal ions such as ethylene-diamine-tetraacetic-acid (EDTA) or a derivative thereof, diethylene-triamine-penta-acetic acid (DTPA) or a derivative thereof.

In one embodiment of the present invention or the method of the present invention the agent-entrapping component is a chelator selected from the group consisting of 1,4-ethano-1, 4,8,11-tetraazacyclotetradecane (et-cyclam) or a derivative thereof; 1,4,7,11-tetraazacyclotetradecane (iso-cyclam) or a derivative thereof; 1,4,7,10-tetraazacyclododecane-1,4,7,10-tetraacetic acid (DOTA) or a derivative thereof; 2-(1,4,7,10-tetraazacyclododecan-1-yl)acetate (DO1A) or a derivative thereof; 2,2'-(1,4,7,10-tetraazacyclododecane-1,7-diyl) diacetic acid (DO2A) or a derivative thereof; 2,2',2"-(1,4,7,10-tetraazacyclododecane-1,4,7-triyl) triacetic acid (DO3A) or a derivative thereof; 1,4,7,10-tetraazacyclododecane-1,4,7,10-tetra(methanephosphonic acid) (DOTP) or a derivative thereof; 1,4,7,10-tetraazacyclododecane-1,7-di(methanephosphonic acid) (DO2P) or a derivative thereof; 1,4,7,10-tetraazacyclododecane-1,4,7-tri(methanephosphonic acid) (DO3P) or a derivative thereof; 1,4,8,11-15 tetraazacyclotetradecane-1,4,8,11-tetraacetic acid (TETA) or a derivative thereof; 2-(1,4,8,11-tetraazacyclotetradecane-1-yl)acetic acid (TE1A) or a derivative thereof; 2,2'-(1,4,8,11-tetraazacyclotetradecane-1,8-diyl) diacetic acid (TE2A) or a derivative thereof; and other adamanzanes or derivates thereof.

In one embodiment of the present invention or the method of the present invention the agent-entrapping component is selected from the group consisting of 1,4,7,10-tetraazacyclododecane-1,4,7,10-tetraacetic acid (DOTA) or a derivative thereof, 1,4,8,11-15 tetraazacyclotetradecane-1,4,8,11-tetraacetic acid (TETA) or a derivative thereof, 1,4,7,10-tetraazacyclododecane-1,4,7,10-tetra(methanephosphonic acid) (DOTP), cyclam and cyclen.

In one preferred embodiment of the present invention or the method of the present invention the agent-entrapping component is selected from the group consisting of 1,4,7,10-tetraazacyclododecane-1,4,7,10-tetraacetic acid (DOTA), 1,4,8,11-15 tetraazacyclotetradecane-1,4,8,11-tetraacetic acid (TETA), 1,4,7,10-tetraazacyclododecane-1,4,7,10-tetra (methanephosphonic acid) (DOTP), cyclam, and cyclen. In one embodiment of the present invention or the method of the present invention the agent-entrapping component is selected from the group consisting of 1,4,7,10-tetraazacyclododecane-1,4,7,10-tetraacetic acid (DOTA) or a derivative thereof.

In a particularly important embodiment of the present invention or method of the present invention, the agent-entrapping component is 1,4,7,10-tetraazacyclododecane-1,4,7,10-tetraacetic acid (DOTA).

In a particularly important embodiment of the present invention or the method of the present invention, the interior pH of the liposome composition is controlled, thus achieving a desired protonation state of the agent entrapping component and/or the ionophore, thereby securing efficient loading and entrapment of the radionuclide. In one embodiment of the present invention or the method of the present invention, the interior pH of the nanoparticle is within the range of 1 to 10, such as 1-2, for example 2-3, such as 3-4, for example 4-5, such as 5-6, for example 6-7, such as 7-8, for example 8-9, such as 9-10. In a preferred embodiment of the present invention or the method of the present invention, the interior pH of the nanoparticle is within the range of 3 to 8, such as 3.0 to 3.5, for example 3.5 to 4.0, such as 4.0 to 4.5, for example 4.5 to 5.0, such as 5.0 to 5.5 for example 5.5 to 6.0.

In another preferred embodiment, the interior pH of the nanoparticle is within the range of 3 to 8, such as 3.0 to 3.5, for example 3.5 to 4.0, such as 4.0 to 4.5, for example 4.5 to 5.0, such as 5.0 to 5.5 for example 5.5 to 6.0, such as 6.0 to 6.5, for example 6.5 to 7.0, such as 7.0 to 7.5, for example 7.5 to 8

Ionophore:

An ionophore of the present invention or the method of the present invention is a lipid-soluble molecule capable of complexing a radionuclide or a metal entity, and hereafter transporting this complex across a bilayer. Within the present invention the ionophore forms complexes with a radionuclide and transports the radiolabeled complex over the liposome lipid bilayer. Examples of ionophores of the present invention or the method of the present invention include, but are not limited to, 2-hydroxyquinoline (carbostyril) in FIG. 1A, which illustrates the structure of carbostyril and the quinoline ($C_9H_7N$) (FIG. 1B) in general, such as, but not limited to, 2-hydroxyquinoline-4-carboxylic acid; 6-chloro-2-hydroxyquinoline; 8-chloro-2-hydroxyquinoline; carbostyril 124; carbostyril 165; 4,6-dimethyl-2-hydroxyquinoline; 4,8-dimethyl-2-hydroxyquinoline; or other 2-quinolinol compounds; or other structures, but not limited, to the compounds illustrated in FIG. 1 or preferably FIG. 2. Such examples also includes compounds illustrated in FIG. 1 or FIG. 2—wherein R, $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X is selected from the group consisting of hydroxy (OH), sulphydryl (SH) and amino ($NH_2$), and $R_1$, $R_2$, $R_3$, $R_4$, $R_5$, and $R_6$ independently of each other represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$, and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X is selected from the group consisting of hydroxy (OH), and $R_1$, $R_2$, $R_3$, $R_4$, $R_5$, and $R_6$ independently of each other represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$), and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X is selected from the group consisting of hydroxy (OH), sulphydryl (SH) and amino ($NH_2$), $R_1$ is hydrogen (H) and $R_2$, $R_3$, $R_4$, $R_5$, and $R_6$ independently of each other represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$), and wherein $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X is selected from the group consisting of hydroxy (OH), sulphydryl (SH) and amino ($NH_2$), $R_1$ and $R_2$ is hydrogen (H) and $R_3$, $R_4$, $R_5$, and $R_6$ independently of each other represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$), and wherein $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X is selected from the group consisting of hydroxy (OH), sulphydryl (SH) and amino ($NH_2$), $R_1$, $R_2$ and $R_3$ is hydrogen (H), and $R_4$, $R_5$, and $R_6$ independently of each other represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$), and wherein $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X is selected from the group consisting of hydroxy (OH), sulphydryl (SH) and amino ($NH_2$), $R_1$, $R_2$, $R_3$ and $R_4$ is hydrogen (H) and $R_5$ and $R_6$ independently of each other represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$), and wherein $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X is selected from the group consisting of hydroxy (OH), sulphydryl (SH) and amino ($NH_2$), $R_1$, $R_2$, $R_3$, $R_4$ and $R_5$ is hydrogen (H) and $R_6$ represents substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), glucoronide ($C_6H_9O_7$), sulphonyl ($SO_3H$), benzoyl ($C_6H_4COOH$), and benzyl ($C_6H_5(CH_2)$).

In one embodiment of the present invention or the method of the present invention, the ionophore is illustrated in FIG. 2, wherein X represents hydroxy (OH), sulphydryl (SH) and amino ($NH_2$), and $R_1$, $R_2$, $R_3$, $R_4$, $R_5$, and $R_6$ independently of each other, represent substituents selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino ($N(CH_3)_2$), hydroxy (OH), cyano (CN), sulphydryl (SH), carboxy (COOH), β-D-galactopyranoside ($C_6O_6H_{11}$), β-D-glucopyranoside ($C_6O_6H_{11}$), and sulphonyl ($SO_3H$), and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X represents hydroxy (OH), sulphydryl (SH) and amino ($NH_2$), and $R_1$, $R_2$, $R_3$, $R_4$, $R_5$, and $R_6$ independently of each other, represent substituents selected from the group consisting of hydrogen (H), halo (Cl, Br, I), methyl ($CH_3$), ethyl ($C_2H_5$), propyl ($C_3H_8$), amino ($NH_2$), dimethylamino ($N(CH_3)_2$), hydroxy (OH), cyano (CN), sulphydryl (SH), carboxy (COOH), and sulphonyl ($SO_3H$), and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X represents hydroxy (OH), sulphydryl (SH) and amino ($NH_2$), and $R_1$, $R_2$, $R_3$, $R_4$, $R_5$, and $R_6$ independently of each other, represent substituents selected from the group consisting of hydrogen (H), halo (Cl, Br, I), methyl ($CH_3$), ethyl ($C_2H_5$), propyl ($C_3H_8$), amino ($NH_2$), hydroxy (OH), sulphydryl (SH), and carboxy (COOH), and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X represents hydroxy (OH), sulphydryl (SH) and amino ($NH_2$), and $R_1$, $R_2$, $R_3$, $R_4$, $R_5$, and $R_6$ independently of each other, represent substituents selected from the group consisting of hydrogen (H), halo (Cl, Br, I), methyl ($CH_3$), ethyl ($C_2H_5$), amino ($NH_2$), hydroxy (OH), sulphydryl (SH), and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In one embodiment of the present invention or the method of the present invention, the ionophore is illustrated in FIG. 2, wherein X represents hydroxy (OH), sulphydryl (SH) and amino ($NH_2$), and $R_1$, $R_2$, $R_3$, $R_4$, $R_5$, and $R_6$ independently of each other, represent substituents selected from the group consisting of hydrogen (H), amino ($NH_2$), and hydroxy (OH), ethyl ($C_2H_5$), and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

In a preferred embodiment of the invention or the method of the invention, the ionophore is selected from the group consisting of 2-hydroxyquinoline, 2-hydroxyquinoline-4-carboxylic acid; 6-chloro-2-hydroxyquinoline; 8-chloro-2-hydroxyquinoline; carbostyril 124; carbostyril 165; 4,6-dimethyl-2-hydroxyquinoline; 4,8-dimethyl-2-hydroxyquinoline.

Other ionophores used within the present invention or the method of the present invention are illustrated in FIG. 3 or preferably FIG. 4 and include, but are not limited to, 8-hydroxyquinoline (oxine); 8-hydroxyquinoline β-D-galactopyranoside; 8-hydroxyquinoline β-D-glucopyranoside; 8-hydroxyquinoline glucuronide; 8-hydroxyquinoline-5-sulfonic acid; 8-hydroxyquinoline-β-D-glucuronide sodium salt; 8-quinolinol hemisulfate salt; 8-quinolinol N-oxide; 2-amino-8-quinolinol; 5,7-dibromo-8-hydroxyquinoline; 5,7-dichloro-8-hydroxyquinoline; 5,7-diiodo-8-hydroxyquinoline; 5,7-dimethyl-8-quinolinol; 5-amino-8-hydroxyquinoline dihydro-chloride; 5-chloro-8-quinolinol; 5-nitro-8-hydroxyquinoline; 7-bromo-5-chloro-8-quinolinol; N-butyl-2,2'-imino-di(8-quinolinol); 8-hydroxyquinoline benzoate; 2-benzyl-8-hydroxyquinoline; 5-chloro-8-hydroxyquinoline hydrochloride; 2-methyl-8-quinolinol; 5-chloro-7-iodo-8-quinolinol; 8-hydroxy-5-nitroquinoline; 8-hydroxy-7-iodo-5-quinolinesulfonic acid; 5,7-dichloro-8-hydroxy-2-methylquinoline, other quinoline consisting chemical compounds and derivative thereof, and other ionophores.

In one embodiment of the present invention or the method of the present invention the ionophore is illustrated in FIG. 4, wherein Y is selected from the group consisting of hydroxy (OH), sulphydryl (SH) and amino ($NH_2$), and $R_7$, $R_8$, $R_9$, $R_{10}$, $R_{11}$, and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino ($N(CH_3)_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glu-coronide ($C_6H_9O_7$), sulphonyl ($SO_3H$), benzoyl ($C_6H_4COOH$), and benzyl ($C_6H_5(CH_2)$), and wherein $R_7$ and $R_8$, $R_8$ and $R_9$, $R_9$ and $R_{10}$, $R_{10}$ and $R_{11}$, or $R_{11}$ and $R_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH) and $R_7$, $R_8$, $R_9$, $R_{10}$, $R_{11}$, and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino ($N(CH_3)_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glucoronide ($C_6H_9O_7$), sulphonyl ($SO_3H$), benzoyl ($C_6H_4COOH$), and benzyl ($C_6H_5(CH_2)$), and wherein $R_7$ and $R_8$, $R_8$ and $R_9$, $R_9$ and $R_{10}$, $R_{10}$ and $R_{11}$, or $R_{11}$ and $R_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino ($NH_2$), $R_7$ represents hydrogen (H) and $R_8$, $R_9$, $R_{10}$, $R_{11}$, and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino ($N(CH_3)_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glucoronide ($C_6H_9O_7$), sulphonyl ($SO_3H$), benzoyl ($C_6H_4COOH$), and benzyl ($C_6H_5(CH_2)$), and wherein $R_8$ and $R_9$, $R_9$ and $R_{10}$, $R_{10}$ and $R_{11}$, or $R_{11}$ and $R_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino ($NH_2$), $R_7$ and $R_8$ represent hydrogen (H) and $R_9$, $R_{10}$, $R_{11}$, and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino ($N(CH_3)_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glucoronide ($C_6H_9O_7$), sulphonyl ($SO_3H$), benzoyl ($C_6H_4COOH$), and benzyl ($C_6H_5(CH_2)$), and wherein $R_9$ and $R_{10}$, $R_{10}$ and $R_{11}$, or $R_{11}$ and $R_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino ($NH_2$), $R_7$, $R_8$, and $R_9$ represent hydrogen (H) and $R_{10}$, $R_{11}$, and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino ($N(CH_3)_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glucoronide ($C_6H_9O_7$), sulphonyl ($SO_3H$), benzoyl ($C_6H_4COOH$), and benzyl ($C_6H_5(CH_2)$), and wherein $R_{10}$ and $R_{11}$, or $R_{11}$ and $R_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino ($NH_2$), $R_7$, $R_8$, $R_9$, and $R_{10}$ represent hydrogen (H) and $R_{11}$ and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino (N($CH_3$)$_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glucoronide ($C_6H_9O_7$), sulphonyl ($SO_3H$), benzoyl ($C_6H_4COOH$), and benzyl ($C_6H_5(CH_2)$), and wherein $R_{11}$ and $R_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino ($NH_2$), and $R_7$, $R_8$, $R_9$, $R_{10}$ and $R_{11}$ represent hydrogen (H) and $R_{12}$ is selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), nitro ($NO_2$), dimethylamino (N($CH_3$)$_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), glucoronide ($C_6H_9O_7$), sulphonyl ($SO_3H$), benzoyl ($C_6H_4COOH$), and benzyl ($C_6H_5(CH_2)$).

In one embodiment of the present invention or the method of the present invention the ionophore is illustrated in FIG. 4, wherein Y is selected from the group consisting of hydroxy (OH), sulphydryl (SH) and amino ($NH_2$), and $R_7$, $R_8$, $R_9$, $R_{10}$, $R_{11}$, and $R_{12}$ are independently selected from the group consisting of hydrogen (H), halo (Cl, Br, I), methyl ($CH_3$), ethyl ($C_2H_5$), propyl ($C_3H_8$), butyl ($C_4H_{11}$), amino ($NH_2$), dimethylamino (N($CH_3$)$_2$), hydroxy (OH), cyano (CN), carboxy (COOH), β-D-galactopyranoside ($C_6O_6H_{11}$), β-D-glucopyranoside ($C_6O_6H_{11}$), sulphydryl (SH), and sulphonyl ($SO_3H$), and wherein $R_7$ and $R_8$, $R_8$ and $R_9$, $R_9$ and $R_{10}$, $R_{10}$ and $R_{11}$, or $R_{11}$ and $R_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino ($NH_2$), and $R_7$, $R_8$, $R_9$, $R_{10}$, $R_{11}$, and $R_{12}$ independently of each other, represent substituents selected from the group consisting of hydrogen (H), halo (Cl, Br, I), methyl ($CH_3$), ethyl ($C_2H_5$), propyl ($C_3H_8$), amino ($NH_2$), dimethylamino (N($CH_3$)$_2$), hydroxy (OH), cyano (CN), carboxy (COOH), sulphydryl (SH), and sulphonyl (SO$_3$H), and wherein R$_7$ and R$_8$, R$_8$ and R$_9$, R$_9$ and R$_{10}$, R$_{10}$ and R$_{11}$, or R$_{11}$ and R$_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino (NH$_2$), and R$_7$, R$_8$, R$_9$, R$_{10}$, R$_{11}$, and R$_{12}$ independently of each other, represent substituents selected from the group consisting of hydrogen (H), halo (Cl, Br, I), methyl (CH$_3$), ethyl (C$_2$H$_5$), propyl (C$_3$H$_8$), amino (NH$_2$), hydroxy (OH), sulphydryl (SH), and carboxy (COOH), and wherein R$_7$ and R$_8$, R$_8$ and R$_9$, R$_9$ and R$_{10}$, R$_{10}$ and R$_{11}$, or R$_{11}$ and R$_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino (NH$_2$), and R$_7$, R$_8$, R$_9$, R$_{10}$, R$_{11}$, and R$_{12}$ independently of each other, represent substituents selected from the group consisting of hydrogen (H), halo (Cl, Br, I), methyl (CH$_3$), ethyl (C$_2$H$_5$), hydroxy (OH), carboxy (COOH), and sulphydryl (SH), and wherein R$_7$ and R$_8$, R$_8$ and R$_9$, R$_9$ and R$_{10}$, R$_{10}$ and R$_{11}$, or R$_{11}$ and R$_{12}$—together with the aromatic ring to which they are attached—may form a benzo-fused carbocyclic aromatic ring or an aliphatic ring.

In one embodiment of the present invention or the method of the present invention the ionophore is illustrated in FIG. 4, wherein Y is selected from the group consisting of hydroxy (OH), sulphydryl (SH) and amino (NH$_2$), and R$_7$, R$_8$, R$_9$, R$_{10}$, R$_{11}$, and R$_{12}$ independently of each other, represent substituents selected from the group consisting of hydrogen (H), ethyl (C$_2$H$_5$), amino (NH$_2$), and hydroxy (OH), and wherein R$_7$ and R$_8$, R$_8$ and R$_9$, R$_9$ and R$_{10}$, R$_{10}$ and R$_{11}$, or R$_{11}$ and R$_{12}$—together with the aromatic ring to which they are attached—may form a benzo-fused carbocyclic aromatic ring or an aliphatic ring.

In a preferred embodiment of the invention or the method of the invention, the ionophore is selected from the group consisting of 8-hydroxyquinoline (oxine); 8-hydroxyquinoline β-D-galactopyranoside; 8-hydroxyquinoline β-D-glucopyranoside; 8-hydroxyquinoline glucuronide; 8-hydroxyquinoline-5-sulfonic acid; 8-hydroxyquinoline-β-D-glucuronide sodium salt; 8-quinolinol hemisulfate salt; 8-quinolinol N-oxide; 2-amino-8-quinolinol; 5,7-dibromo-8-hydroxyquinoline; 5,7-dichloro-8-hydroxyquinoline; 5,7-di-iodo-8-hydroxyquinoline; 5,7-dimethyl-8-quinolinol; 5-amino-8-hydroxyquinoline dihydrochloride; 5-chloro-8-quinolinol; 5-nitro-8-hydroxyquinoline; 7-bromo-5-chloro-8-quinolinol; N-butyl-2,2'-imino-di(8-quinolinol); 8-hydroxyquinoline benzoate; 2-benzyl-8-hydroxyquinoline; 5-chloro-8-hydroxyquinoline hydrochloride; 2-methyl-8-quinolinol; 5-chloro-7-iodo-8-quinolinol; 8-hydroxy-5-nitroquinoline; 8-hydroxy-7-iodo-5-quinolinesulfonic acid; 5,7-dichloro-8-hydroxy-2-methylquinoline.

In one embodiment of the invention or the method of the invention, the ionophore is selected from the group consisting A23187, hexamethylpropylene amine oxime (HMPAO) and derivatives thereof, diisopropyl iminodiacetic acid diisopropyl iminodiacetic acid (DISIDA) and derivatives thereof, phthaldialdehyde and derivatives thereof, 2,4-dinitrophenol and derivatives thereof, beauvericin and derivatives thereof, di-benzo-18-crown-6 and derivatives thereof, o-xylylenebis (N,N-diisobutyldithiocarbamate) and derivatives thereof, N,N,N',N'-Tetracyclohexyl-2,2'-thiodiacetamide and derivates thereof, 2-(1,4,8,11-Tetrathiacyclotetradec-6-yloxy) hexanoic acid, 2-(3,6,10,13-Tetrathiacyclotetradec-1-oxy) hexanoic acid and derivates thereof, N,N-bis(2-mercaptoethyl)-N',N'-diethylethylenediamine and derivates thereof.

In a preferred embodiment of the present invention, the ionophore is carbostyril (2-hydroxyquinoline, 2HQ).

In one embodiment of the present invention or the method of the present invention, the nanoparticle composition contains measurable amounts of the ionophore after loading of the nanoparticles with the copper isotope and purification of said loaded nanoparticles.

In one embodiment of the present invention or the method of the present invention, the nanoparticle composition contains only trace amounts of the ionophore after loading of the nanoparticles with the copper isotope and purification of said loaded nanoparticles.

In one embodiment of the present invention or the method of the present invention, the nanoparticle composition contains no measurable amounts of the ionophore after loading of the nanoparticles with the copper isotope and purification of said loaded nanoparticles.

In one embodiment of the present invention or the method of the present invention, the nanoparticle composition contains measurable amounts of the ionophore after loading of the nanoparticles with the radionuclide and purification of said loaded nanoparticles.

In one embodiment of the present invention or the method of the present invention, the nanoparticle composition contains only trace amounts of the ionophore after loading of the nanoparticles with the radionuclide and purification of said loaded nanoparticles.

In one embodiment of the present invention or the method of the present invention, the nanoparticle composition contains no measurable amounts of the ionophore after loading of the nanoparticles with the radionuclide and purification of said loaded nanoparticles.

In one embodiment of the present invention or the method of the present invention for producing a nanoparticle composition loaded with a copper isotope, the described agent-entrapping component is a chelator (e.g. DOTA) and the reaction of transfer of copper from the ionophore to the chelating agent is spontaneous either inherently when $\Delta G° < 0$, where $\Delta G°$ is the standard Gibbs free energy of exchange, or as a result of a high concentration of chelating agent within the nanoparticle composition.

In one embodiment of the present invention or the method of the present invention for producing a nanoparticle composition loaded with a radionuclide, the described agent-entrapping component is a chelator (e.g. DOTA) and the reaction of transfer of radionuclide from the ionophore to the chelating agent is spontaneous either inherently when $\Delta G° < 0$, where $\Delta G°$ is the standard Gibbs free energy of exchange, or as a result of a high concentration of chelating agent within the nanoparticle composition.

In one embodiment of the present invention or the method of the present invention, the stability of the radiolabeled nanoparticles generated by the disclosed method is such that less than 20% leakage of radioactivity is observed following 24 hours incubation in buffer or human serum at 37° C. followed by a purification procedure to separate the radiolabeled nanoparticles from leaked radionuclide, for example less than 15% leakage, such as less than 12% leakage, for example less than 10% leakage, such as less than 8% leakage, for example less than 6% leakage, such as less than 4% leakage, for example less than 3% leakage, such as less than 2% leakage, for example less than 1% leakage. Said purification procedure comprises size exclusion chromatography (SEC), ion-exchange chromatography or dialysis.

In one embodiment of the disclosed method for producing a nanoparticle composition loaded with a copper isotope, the described agent entrapping compound is a chelator (e.g. DOTA) and the molar ratio of ionophore to chelator is in the range of 1:1 to 1:10000000, for example 1:5, such as 1:10, for example 1:50, such as 1:100, for example 1:250, such as 1:500, for example 1:1000, such as 1:5000, for example 1:10000, such as 1:50000, for example 1:100000, such as 1:500000, for example 1:1000000, such as 1:5000000, for example 1:10000000.

In one embodiment of the disclosed method for producing a nanoparticle composition loaded with a radionuclide, wherein the ionophore described in formula A is used for loading, the described agent entrapping component is a chelator (e.g. DOTA) and the molar ratio of ionophore to chelator is in the range of 1:1 to 1:10000000, for example 1:5, such as 1:10, for example 1:50, such as 1:100, for example 1:250, such as 1:500, for example 1:1000, such as 1:5000, for example 1:10000, such as 1:50000, for example 1:100000, such as 1:500000, for example 1:1000000, such as 1:5000000, for example 1:10000000.

In one embodiment of the present invention or the disclosed method for producing a nanoparticle composition loaded with a copper isotope, the interior pH is controlled during synthesis of the nanoparticles in such a way that the interior pH of the nanoparticles is within the range 4-5. In another embodiment of the disclosed method for producing a nanoparticle composition loaded with a copper isotope, the interior pH is controlled during synthesis of the nanoparticles in such a way that the interior pH of the nanoparticles is within the range of 1 to 10, such as 1-2, for example 2-3, such as 3-4, for example 4-5, such as 5-6, for example 6-7, such as 7-8, for example 8-9, such as 9-10.

In one embodiment of the present invention or the disclosed method for producing a nanoparticle composition loaded with a radionuclide, wherein the ionophore described in formula A is used for loading, the interior pH is controlled during synthesis of the nanoparticles in such a way that the interior pH of the nanoparticles is within the range 4-5. In another embodiment of the disclosed method for producing a nanoparticle composition loaded with a radionuclide, the interior pH is controlled during synthesis of the nanoparticles in such a way that the interior pH of the nanoparticles is within the range of 1 to 10, such as 1-2, for example 2-3, such as 3-4, for example 4-5, such as 5-6, for example 6-7, such as 7-8, for example 8-9, such as 9-10.

In a preferred embodiment of the present invention, the interior pH of the nanoparticles is in the range of 3 to 8, such as 3.0 to 3.5, for example 3.5 to 4.0, such as 4.0 to 4.5, for example 4.5 to 5.0, such as 5.0 to 5.5 for example 5.5 to 6.0, such as 6.0 to 6.5, for example 6.5 to 7.0, such as 7.0 to 7.5, for example 7.5 to 8.

In one embodiment, the disclosed method for producing a nanoparticle loaded with copper results in nanoparticles which have a diameter of less than 120 nm.

In one embodiment, the disclosed method for producing a nanoparticle loaded with a radionuclide results in nanoparticles which have a diameter of less than 120 nm.

In another embodiment, the disclosed method for producing a nanoparticle loaded with copper results in nanoparticles which have a diameter of more than 80 nm.

In another embodiment, the disclosed method for producing a nanoparticle loaded with a radionuclide results in nanoparticles which have a diameter of more than 80 nm.

In a preferred embodiment, the disclosed method for producing a nanoparticle loaded with copper results in nanoparticles which has a diameter in the range of 30 nm to 300 nm; such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm.

In a preferred embodiment, the disclosed method for producing a nanoparticle loaded with radionuclides results in nanoparticles which has a diameter in the range of 30 nm to 300 nm; such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm.

In one embodiment of the present invention or the method of the present invention, the efficiency of loading is higher than 90% when assayed using size exclusion chromatography (SEC, described in examples), ion-exchange chromatography or dialysis. In another embodiment of the present method the efficiency of loading is higher than 35%, for example higher than 40%, such as higher than 50%, for example higher than 60%, such as higher than 65%, for example higher than 70%, such as higher than 75%, for example higher than 80%, such as higher than 85%, for example higher than 90%, such as higher than 95%.

In one embodiment of the invention or the disclosed method of the invention, the generated nanoparticles loaded with copper are purified using SEC, ion-exchange chromatography or dialysis.

In one embodiment of the invention or the disclosed method of the invention, the generated nanoparticles loaded with radionuclides are purified using SEC, ion-exchange chromatography or dialysis.

In one embodiment of the disclosed method, the size of the nanoparticle compositions remains essentially unaltered following loading of said nanoparticles with copper. In another embodiment of the disclosed method, the size of the nanoparticle compositions is altered less than 20% following loading of the nanoparticles with copper isotopes, for example less than 17%, such as less than 14%, for example less than 11%, such as less than 8%, for example less than 5%, such as less than 2%, for example less than 1%.

In one embodiment of the disclosed method, the size of the nanoparticle compositions remains essentially unaltered following loading of said nanoparticles with a radionuclide. In another embodiment of the disclosed method, the size of the nanoparticle compositions is altered less than 20% following loading of the nanoparticles with a radionuclide, for example less than 17%, such as less than 14%, for example less than 11%, such as less than 8%, for example less than 5%, such as less than 2%, for example less than 1%.

In one embodiment of the disclosed method, the zeta potential is altered less than 20% following loading of the nanoparticles with copper isotopes. In another embodiment of the disclosed method, the zeta potential is altered less than 18% following loading of the nanoparticles with copper isotopes, for example less than 16%, such as less than 14%, for example less than 12%, such as less than 10%.

In one embodiment of the disclosed method, the zeta potential is altered less than 20% following loading of the nanoparticles with a radionuclide. In another embodiment of the disclosed method, the zeta potential is altered less than 18% following loading of the nanoparticles with a radionuclide, for example less than 16%, such as less than 14%, for example less than 12%, such as less than 10%.

One embodiment of the present invention or the method of the present invention further comprises using the nanoparticles generated according to the disclosed method for diagnosis or treatment.

One embodiment of the present invention or the method of the present invention further comprises intravenous administration of the nanoparticles generated according to the disclosed method.

One embodiment of the present invention or the method of the present invention further comprises oral administration of the nanoparticles generated according to the disclosed method.

Kit of Parts

In a further aspect, the present invention relates to a kit of parts comprising:
a. a nanoparticle composition comprising i) a vesicle forming component, and ii) an agent-entrapping component enclosed by the vesicle forming component; and
b. a composition containing an ionophore, and
c. a composition containing a copper isotope which may or may not be a radionuclide,
wherein all the components are those which have been described in the preceding brief description of the present invention or the preceding detailed description of the present invention.

In one embodiment of said kit of parts, the copper isotope which may or may not be a radionuclide is a constituent part b and therefore said it of parts comprises:
a. a nanoparticle composition comprising i) a vesicle forming component, and ii) an agent-entrapping component enclosed by the vesicle forming component; and
b. a composition containing iii) an ionophore and iv) a copper isotope
wherein all the components are those which have been described in the preceding brief description of the present invention or the preceding detailed description of the present invention.

In yet another embodiment of said kit of parts, the copper isotope which may or may not be a radionuclide is a constituent of part a and therefore said kit of part comprises:
a. a nanoparticle composition comprising i) a vesicle forming component, ii) an agent-entrapping component enclosed by the vesicle forming component, and iii) a copper isotope; and
b. a composition containing an ionophore
wherein all the components are those which have been described in the preceding brief description of the present invention or the preceding detailed description of the present invention.

In another embodiment of said kit of parts, part a contains the ionophore in addition to the vesicle forming component and the agent-entrapping component, and therefore said kit of part comprises:
a. a nanoparticle composition comprising i) a vesicle forming component, ii) an agent-entrapping component enclosed by the vesicle forming component, and iii) an ionophore; and
b. a composition containing a copper isotope
wherein all the components are those which have been described in the preceding brief description of the present invention or the preceding detailed description of the present invention.

In yet another embodiment of said kit of parts, said kit of parts is for preparation of nanoparticles comprising isotopes, and said isotopes are provided separately from the kit of parts. Therefore said kit of parts comprises:

a. a nanoparticle composition comprising i) a vesicle forming component, ii) an agent-entrapping component enclosed by the vesicle forming component, and
b. an ionophore composition;
wherein all the components are those which have been described in the preceding brief description of the present invention or the preceding detailed description of the present invention.

In one embodiment, the composition containing the radionuclide is either in storage or delivered from the manufacturer depending on the characteristics of the particular radionuclide. If the radionuclide is e.g. the positron emitter $^{64}Cu$, said radionuclide is delivered directly from a cyclotron facility to the venue of treatment or diagnosis immediately prior to use, in the form of a (lyophilized) salt or an aqueous solution. Before administration of the radionuclide-containing nanoparticles, parts a, b, and c of the kit are mixed and the efficiency of encapsulation is tested, preferably using the simple test procedure supplied with the kit. Following administration the patient may receive a PET- or a SPECT scan. Optimal visualization may be achieved 4-24 hours after administration.

The group of copper isotopes comprised in the kits of the present invention comprises $^{61}Cu$, $^{64}Cu$, and $^{67}Cu$.

In one embodiment of the disclosed kit of parts described herein above, said ionophore is as defined in formula A, the kit of parts comprise a combination of radionuclides selected from the group consisting of Copper ($^{61}Cu$, $^{64}Cu$, and $^{67}Cu$), Indium ($^{111}In$), Technetium ($^{99m}Tc$), Rhenium ($^{186}Re$, $^{188}Re$), Gallium ($^{67}Ga$, $^{68}Ga$), Strontium ($^{89}Sr$), Samarium ($^{153}Sm$), Ytterbium ($^{169}Yb$), Thallium ($^{201}Tl$), Astatine ($^{211}At$), Lutetium ($^{177}Lu$), Actinium ($^{225}Ac$), Yttrium ($^{90}Y$), Antimony ($^{119}Sb$), Tin ($^{117}Sn$, $^{113}Sn$), Dysprosium ($^{159}Dy$), Cobalt ($^{56}Co$), Iron ($^{59}Fe$), Ruthenium ($^{97}Ru$, $^{103}Ru$), Palladium ($^{103}Pd$), Cadmium ($^{115}Cd$), Tellurium ($^{118}Te$, $^{123}Te$), Barium ($^{131}Ba$, $^{140}Ba$), Gadolinium ($^{149}Gd$, $^{151}Gd$), Terbium ($^{160}Tb$), Gold ($^{198}Au$, $^{199}Au$), Lanthanum ($^{140}La$), and Radium ($^{223}Ra$, $^{224}Ra$).

In another aspect of the disclosed kit of parts described herein above, wherein said ionophore is as defined in formula A, including any preferred embodiments of A, a radionuclide different from copper is used, said radionuclide being selected from the group consisting of Indium ($^{111}In$), Technetium ($^{99m}Tc$), Rhenium ($^{188}Re$), Gallium ($^{67}Ga$, $^{68}Ga$), and Lutetium ($^{177}Lu$), Actinium ($^{225}Ac$), Yttrium ($^{90}Y$), Antimony ($^{119}Sb$), Tin ($^{117}Sn$, $^{113}Sn$), Dysprosium ($^{159}Dy$), Cobalt ($^{56}Co$), Iron ($^{59}Fe$), Ruthenium ($^{97}Ru$, $^{103}Ru$), Palladium ($^{103}Pd$), Cadmium ($^{115}Cd$), Tellurium ($^{118}Te$, $^{123}Te$), Barium ($^{131}Ba$, $^{140}Ba$), Gadolinium ($^{149}Gd$, $^{151}G$), Terbium ($^{160}Tb$), Gold ($^{198}Au$, $^{199}Au$), Lanthanum ($^{140}La$), and Radium ($^{223}Ra$, $^{224}Ra$). The radionuclide may be delivered in the form of a (lyophilized) salt or an aqueous solution or may be synthesized on the premises using existing production facilities and starting materials. Before administration of the radionuclide-containing nanoparticles, parts a, b, and c of the kit are mixed and the efficiency of encapsulation is tested, preferably using the simple test procedure supplied with the kit. Following test of encapsulation, the drug is administered to the patient.

In another embodiment of the disclosed kit of parts described herein above, wherein said ionophore is as defined in formula A, a radionuclide different from copper is used, said radionuclide being selected from the group consisting of Indium ($^{111}In$), Technetium ($^{99m}Tc$), Rhenium ($^{188}Re$), Gallium ($^{67}Ga$, $^{68}Ga$), Actinium ($^{225}Ac$), Yttrium ($^{90}Y$), Antimony ($^{119}Sb$) and Lutetium ($^{177}Lu$). The radionuclide may be delivered in the form of a (lyophilized) salt or an aqueous solution or may be synthesized on the premises using existing production facilities and starting materials. Before administration of the radionuclide-containing nanoparticles, parts a, b, and c of the kit are mixed and the efficiency of encapsulation is tested, preferably using the simple test procedure supplied with the kit. Following test of encapsulation, the drug is administered to the patient.

In a preferred embodiment of the disclosed kit of parts described herein above, wherein said ionophore is as defined in formula A, the kit of parts comprise a combination of radionuclides useful for combined positron emission tomography (PET) imaging and radiation therapy, such as $^{64}$Cu and $^{177}$Lu, or such as $^{64}$Cu and $^{67}$Cu, or such as $^{61}$Cu and $^{67}$Cu, or such as $^{64}$Cu and $^{90}$Y, or such as $^{64}$Cu and $^{119}$Sb, or such as $^{64}$C and $^{225}$Ac, or such as $^{64}$Cu and $^{188}$Re, or such as $^{64}$Cu and $^{186}$Re, or such as $^{64}$Cu and $^{211}$At.

In an even more preferred embodiment of the disclosed kit of parts described herein above, wherein said ionophore is as defined in formula A, the kit of parts comprise a combination of radionuclides useful for combined positron emission tomography (PET) imaging and radiation therapy, such as $^{64}$Cu and $^{177}$Lu.

In one embodiment of the disclosed kit of parts described herein above, said ionophore is carbostyril (2HQ), and said kit of parts is for preparation of nanoparticles comprising isotopes selected from the group consisting of Copper ($^{61}$Cu, $^{64}$Cu, and $^{67}$Cu), Indium ($^{111}$In), Technetium ($^{99m}$Tc), Rhenium, ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl) Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb) Gold ($^{198}$Au, $^{199}$Au), Lanthanum ($^{140}$La), and Radium ($^{223}$Ra, $^{224}$Ra) wherein said isotopes may or may not be part of the kit of parts.

In one embodiment of the disclosed kit of parts described herein above, said ionophore is any ionophore according to the present invention, and said kit of parts is for preparation of nanoparticles comprising isotopes of Copper ($^{61}$Cu, $^{64}$Cu, and $^{67}$Cu), wherein said isotopes may or may not be part of the kit of parts.

In a preferred embodiment, any of the kit of parts further comprises a test procedure to assess the efficiency of encapsulation.

Nanoparticle Compositions

In one aspect, this invention relates to a radiolabeled nanoparticle composition consisting of a vesicle forming component, an agent-entrapping component enclosed by the vesicle-forming component, and a radiolabeled agent entrapped within the nanoparticle composition, wherein the radiolabeled agent comprises a copper isotope.

The radiolabeled nanoparticle composition mentioned above may further comprise a targeting moiety enabling the nanoparticle to specifically bind to target cells bearing the target molecule, or a moiety specifically binding to diseased target. The targeting moiety may be attached to the surface of the nanoparticle composition via a lipid-anchoring molecule or a PEG-conjugated lipid component.

In envisioned embodiments of the invention, the targeting moiety attached to the surface of the radiolabeled nanoparticle composition may be an antibody, an affibody or a peptide component which may be selected from the group consisting of, but not limited to, antibodies: Rituximab, Trastuzumab, Cetuximab, LymphoCide, Vitaxin, Lym-1 and Bevacizumab; affibodies: for example, but not limited to, anti-ErbB2 affibody molecule and anti-Fibrinogen affibody molecule; and peptides: for example but not limited to RGD, somatostatin and analogs thereof, and cell-penetrating peptides. In a preferred embodiment, the targeting moiety is selected from the group consisting of: Rituximab, Trastuzumab, Cetuximab, LymphoCide, Vitaxin, Lym-1 and Bevacizumab; affibodies: anti-ErbB2 affibody molecule and anti-Fibrinogen affibody molecule; and peptides: RGD, somatostatin and analogs thereof, and cell-penetrating peptides. In one embodiment of the present invention, said somatostatin is octreotate (TATE).

The vesicle-forming component of the described radiolabeled nanoparticle composition comprises an amphiphatic component or a derivative thereof, and polyethylene glycol (PEG) or a derivative thereof, or a polysaccharide. In addition, the radio-labeled nanoparticle composition comprises an agent-entrapping component comprising a chelator selected from the group consisting of, but not limited to, 1,4,7,10-tetraazacyclododecane-1,4,7,10-tetraacetic acid (DOTA) and derivatives thereof; 1,4,8,11-tetraazacyclotetradecane (cyclam) and derivatives thereof; 1,4,7,10-tetraazacyclododecane (cyclen) and derivatives thereof; 1,4-ethano-1,4,8,11-tetraazacyclotetradecane (et-cyclam) and derivatives thereof; 1,4,7,11-tetraazacyclotetradecane (isocyclam) and derivatives thereof; 1,4,7,10-tetraazacyclotridecane ([13]aneN$_4$) and derivatives thereof; 1,4,7,10-tetraazacyclododecane-1,7-diacetic acid (DO2A) and derivatives thereof; 1,4,7,10-tetraazacyclododecane-1,4,7-triacetic acid (DO3A) and derivatives thereof; 1,4,7,10-tetraazacyclododecane-1,7-di(methanephosphonic acid) (DO2P) and derivatives thereof; 1,4,7,10-tetraazacyclododecane-1,4,7-tri (methanephosphonic acid) (DO3P) and derivatives thereof; 1,4,7,10-tetraazacyclododecane-1,4,7,10-tetra(methanephosphonic acid) (DOTP) and derivatives thereof; ethylenediaminetetraacetic acid (EDTA) and derivatives thereof; diethylene triamine pentaacetic acid (DTPA) and derivatives thereof; 1,4,8,11-tetraazacyclotetradecane-1,4,8,11-tetraacetic acid (TETA) and derivatives thereof, or other adamanzanes and derivates thereof. In additional embodiments, the radiolabeled nanoparticle composition may comprise agent-entrapping components such as, but not limited to, ascorbic acid, glucose, fructose, glyceraldehyde, lactose, arabinose, maltose and acetol, or agents that form low solubility salts with copper ions such as, but not limited to, phosphate, oxalate and chloride.

Finally, the described radiolabeled nanoparticle composition may comprise a radio-labeled agent comprising a copper isotope selected from the group consisting of, but not limited to $^{61}$Cu, $^{64}$Cu and $^{67}$Cu.

In a preferred embodiment, the agent-entrapping component is selected from the group consisting of 1,4,7,10-tetraazacyclododecane-1,4,7,10-tetraacetic acid (DOTA) and derivatives thereof; 1,4,8,11-tetraazacyclotetradecane (cyclam) and derivatives thereof; 1,4,7,10-tetraazacyclododecane (cyclen) and derivatives thereof; 1,4-ethano-1,4,8,11-tetraazacyclotetradecane (et-cyclam) and derivatives thereof; 1,4,7,11-tetra-azacyclotetradecane (isocyclam) and derivatives thereof; 1,4,7,10-tetraazacyclotridecane ([13]aneN$_4$) and derivatives thereof; 1,4,7,10-tetraazacyclododecane-1,7-diacetic acid (DO2A) and derivatives thereof; 1,4,7,10-tetraazacyclododecane-1,4,7-triacetic acid (DO3A) and derivatives thereof; 1,4,7,10-tetraazacyclododecane-1,7-di (methanephosphonic acid) (DO2P) and derivatives thereof; 1,4,7,10-tetraazacyclododecane-1,4,7-tri(methanephosphonic acid) (DO3P) and derivatives thereof; 1,4,7,10-tetraazacyclododecane-1,4,7,10-tetra(methanephosphonic acid) (DOTP) and derivatives thereof; ethylenediaminetetraacetic acid (EDTA) and derivatives thereof; diethylene triamine pentaacetic acid (DTPA) and derivatives thereof; 1,4,8,11-tetraazacyclotetradecane-1,4,8,11-tetraacetic acid (TETA) and derivatives thereof, or other adamanzanes and derivatives thereof.

Finally, the described radiolabeled nanoparticle composition may comprise a radio-labeled agent comprising a copper isotope selected from the group consisting of $^{61}$Cu, $^{64}$Cu and $^{67}$Cu.

In a preferred embodiment of the present invention, the agent-entrapping component is a chelator selected from the group consisting of 1,4,7,10-tetraazacyclododecane-1,4,7, 10-tetraacetic acid (DOTA), 1,4,8,11-15 tetraazacyclotetradecane-1,4,8,11-tetraacetic acid (TETA), 1,4,7,10-tetraazacyclododecane-1,4,7,10-tetra(methanephosphonic acid) (DOTP), cyclam and cyclen.

The vesicle-forming component of the radiolabeled nanoparticle composition of this invention is a synthetic or naturally-occurring amphiphatic compound which comprises a hydrophilic component and a hydrophobic component. Vesicle forming components include, for example, fatty acids, neutral fats, phosphatides, glycolipids, aliphatic alcohols, and steroids. Examples of suitable vesicle forming lipids used in the present invention or the method of the present invention include, but are not limited to: phosphatidylcholines such as 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2-palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine; phosphatidylethanolamines such as 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoyl-phosphatidylethanolamine; phosphatidylserines such as 1,2-dioleoyl-phosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl-2-oleoyl-phosphatidylserine and 1-stearoyl-2-oleoyl-phosphatidylserine; phosphatidylglycerols such as 1,2-dioleoyl-phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl-2-oleoyl-phosphatidylglycerol and 1-stearoyl-2-oleoyl-phosphatidylglycerol; pegylated lipids; pegylated phosphoholipids such as phosphatidylethanolamine-N-[methoxy(polyethyleneglycol)-1000], phosphatidylethanolamine-N-[methoxy(polyethyleneglycol)-2000], phosphatidylethanolamine-N-[methoxy(polyethylene glycol)-3000], phosphatidylethanolamine-N-[methoxy(polyethyleneglycol)-5000]; pegylated ceramides such as N-octanoyl-sphingosine-1-{succinyl[methoxy(polyethyleneglycol)1000]}, N-octanoyl-sphingosine-1-{succinyl[methoxy(polyethylene glycol)2000]}, N-octanoyl-sphingosine-1-{succinyl[methoxy(polyethyleneglycol)3000]}, N-octanoyl-sphingosine-1-{succinyl[methoxy(polyethyleneglycol)5000]}; lyso-phosphatidylcholines, lyso-phosphatidylethanolamines, lyso-phosphatidylglycerols, lyso-phosphatidylserines, ceramides; sphingolipids; glycolipids such as ganglioside GMI; glucolipids; sulphatides; phosphatidic acid, such as di-palmitoyl-glycerophosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; polyoxyethylene fatty acids esters and polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; di-oleoyl-sn-glycerol; dipalmitoyl-succinylglycerol; 1,3-dipalmitoyl-2-succinylglycerol; 1-alkyl-2-acyl-phosphatidylcholines such as 1-hexadecyl-2-palmitoyl-phosphatidylcholine; 1-alkyl-2-acyl-phosphatidylethanolamines such as 1-hexadecyl-2-palmitoyl-phosphatidylethanolamine; 1-alkyl-2-acyl-phosphatidylserines such as 1-hexadecyl-2-palmitoyl-phosphatidylserine; 1-alkyl-2-acyl-phosphatidylglycerols such as 1-hexadecyl-2-palmitoyl-phosphatidylglycerol; 1-alkyl-2-alkyl-phosphatidylcholines such as 1-hexadecyl-2-hexadecyl-phosphatidylcholine; 1-alkyl-2-alkyl-phosphatidylethanolamines such as 1-hexadecyl-2-hexadecyl-phosphatidylethanolamine; 1-alkyl-2-alkyl-phosphatidylserines such as 1-hexadecyl-2-hexadecyl-phosphatidylserine; 1-alkyl-2-alkyl-phosphatidylglycerols such as 1-hexadecyl-2-hexadecyl-phosphatidylglycerol; N-Succinyl-dioctadecylamine; palmitoylhomocysteine; lauryltrimethylammonium bromide; cetyltrimethyl-ammonium bromide; myristyltrimethylammonium bromide; N-[1,2,3-dioleoyloxy)-propyl]-N,N,Ntrimethylammoniumchloride (DOTMA); 1,2-dioleoyloxy-3(trimethylammonium)propane(DOTAP); and 1,2-dioleoyl-c-(4'-trimethylammonium)-butanoyl-sn-glycerol (DOTB).

In one embodiment the vesicle forming component include compounds selected from the group of DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]), POPC (1-palmitoyl-2-oleoyl-sn-glycero-3-phosphocholine), DPPC (1,2-dipalmitoyl-sn-glycero-3-phosphocholine), DSPE-PEG$_{2000}$-TATE (1,2-distearoyl-sn-glycero-3-phosphoethanolamine-N-[methoxy (polyethylene glycol)-2000]-TATE).

In a preferred embodiment the vesicle forming component include DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]) in a molar ratio of 50:40:10.

In another preferred embodiment the vesicle forming component include DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]) in a molar ratio of 55:40:5.

In another embodiment of the disclosed method, the vesicle forming component consists of amphiphatic compounds selected from the group consisting of 1,2-distearoyl-sn-glycero-3-phosphocholine (DSPC) "A", cholesterol "B", and 1,2-distearoyl-sn-glycero-3-phosphoethanolamine-N-[methoxy (polyethylene glycol)-2000] (DSPE-PEG-2000) "C", and 1,2-distearoyl-sn-glycero-3-phosphoethanolamine-N-[methoxy (polyethylene glycol)-2000]-TATE (DSPE-PEG-2000-TATE) with the molar ratio A:B:C:D, wherein A is selected from the interval 45 to 65, B is selected from the interval 35 to 45, C is selected from the interval 5 to 13, D is selected from the interval 0 to 3, and wherein A+B+C+D=100.

In a preferred embodiment the vesicle forming component include DSPC (1,2-distearoyl-sn-glycero-3-phosphocholine), CHOL (Cholesterol), DSPE-PEG-2000 (1,2-distearoyl-sn-glycero-3-phosphoethanolamine-N-[methoxy (polyethylene glycol)-2000]) and 1,2-distearoyl-sn-glycero-3-phosphoethanolamine-N-[methoxy (polyethylene glycol)-2000]-TATE (DSPE-PEG-2000-TATE) in a molar ratio of 50:40:9:1.

In a further embodiment of the kit of parts according to the present invention, the ionophore is any ionophore defined as a compound capable of forming a complex with a radionuclide or a metal entity and hereafter transporting this complex across a bilayer, and said one or more radionuclide is selected from the group of copper isotopes consisting of, $^{61}$Cu, $^{64}$Cu, and $^{67}$Cu, wherein said radionuclides may be or may not be part of said kit of parts.

In a one embodiment of the invention the kit of parts comprises an ionophore selected from the group consisting of 8-hydroxyquinoline, 2-hydroxyquinoline, 2-hydroxyquinoline-4-carboxylic acid; 6-chloro-2-hydroxyquinoline; 8-chloro-2-hydroxyquinoline; carbostyril 124; carbostyril 165; 4,6-dimethyl-2-hydroxyquinoline; 4,8-dimethyl-2-hydroxyquinoline, A23187, hexamethylpropylene amine oxime (HMPAO) and diisopropyl iminodiacetic acid diisopropyl iminodiacetic acid (DISIDA), phthaldialdehyde and derivatives thereof, 2,4-dinitrophenol and derivatives thereof, beauvericin and derivatives thereof, di-benzo-18-crown-6 and derivatives thereof, o-xylylenebis(N,N-diisobutyldithiocarbamate) and derivatives thereof, N,N,N',N'-Tetracyclohexyl-2,2'-thiodiacetamide and derivates thereof, 2-(1,4,8,11-Tetrathiacyclotetradec-6-yloxy)hexanoic acid, 2-(3,6,10,13-Tetrathiacyclotetradec-1-oxy)hexanoic acid and derivates thereof, N,N-bis(2-mercaptoethyl)-N',N'-diethylethylenediamine and derivates thereof.

In a preferred embodiment of the present invention, the kit of parts comprises the ionophore carbostyril (2-hydroxyquinoline, 2HQ).

In one embodiment of the disclosed kit of parts described herein above, said ionophore is carbostyril (2HQ), and said kit of parts comprise a combination of radionuclides selected from the group consisting of Copper ($^{61}$Cu, $^{64}$Cu, and $^{67}$Cu).

In one embodiment, the radiolabeled nanoparticle composition of the present invention has a mean particle diameter of 30 nm to 300 nm.

In one embodiment of the invention, the pH of the interior of the described radio-labeled nanoparticle composition may be controlled via protonation or deprotonation of the agent-entrapping component, thereby inducing effective encapsulation of the radionuclide.

In addition to extracellular targeting, in one embodiment of the present invention the radiolabeled nanoparticle composition further comprises a compound with intracellular targeting properties, such as nuclear localization sequence peptide (NLS peptide), conjugated to the agent-entrapping component, thus entrapped within the nanoparticle composition.

Method of Preparation

In a second aspect of the present invention a method for preparing nanoparticle compositions loaded with radionuclides and/or metal entities is disclosed. The invented method provides a nanoparticle composition comprising a vesicle forming component and an agent-entrapping component enclosed by the vesicle forming component, and a component for transporting radionuclides and/or metal entities over membranes thus entrapping a radiolabeled agent within the nanoparticle composition.

In one embodiment of the present aspect of the invention, a method is disclosed for preparation of nanoparticle compositions comprising an amphiphatic component or a derivative thereof, and polyethylene glycol (PEG) or a derivative thereof, or a polysaccharide. In addition, the nanoparticle composition provided by the disclosed method may comprise an agent-entrapping component being a chelator selected form the group consisting of, but not limited to, 1,4,7,10-tetraazacyclododecane-1,4,7,10-tetraacetic acid (DOTA) and derivative thereof; 1,4,8,11-tetraazacyclotetradecane (cyclam) and derivative thereof; 1,4,7,10-tetraazacyclododecane (cyclen) and derivative thereof; 1,4-ethano-1,4,8,11-tetraazacyclotetradecane (et-cyclam) and derivative thereof; 1,4,7,11-tetraazacyclotetradecane (isocyclam) and derivative thereof; 1,4,7,10-tetraazacyclotridecane ([13]anaN$_4$) and derivative thereof; 1,4,7,10-tetraazacyclododecane-1,7-diacetic acid (DO2A) and derivative thereof; 1,4,7,10-tetraazacyclododecane-1,4,7-triacetic acid (DO3A) and derivative thereof; 1,4,7,10-tetraazacyclododecane-1,7-di(methanephosphonic acid) (DO2P) and derivative thereof; 1,4,7,10-tetraazacyclododecane-1,4,7-tri(methanephosphonic acid) (DO3P) and derivative thereof; 1,4,7,10-tetraazacyclododecane-1,4,7,10-tetra(methanephosphonic acid) (DOTP) and derivative thereof; ethylenediaminetetraacetic acid (EDTA) and derivative thereof; diethylene triamine pentaacetic acid (DTPA) and derivative thereof; 1,4,8,11-tetraazacyclotetradecane-1,4,8,11-tetraacetic acid (TETA) and derivative thereof, or other adamanzanes and derivates thereof. In a further embodiment of the invention, the nanoparticle composition may comprise a reducing component such as, but not limited to, ascorbic acid, glucose, fructose, glyceraldehyde, lactose, arabinose, maltose and acetol, or agents that form low solubility salts with copper ions such as, but not limited to, phosphate, oxalate and chloride. Finally, the disclosed method comprises a nanoparticle composition containing a radiolabeled agent which is a radionuclide complexed to an ionophoric compound capable of transporting the complex across a bilayer. In one embodiment, the agent-entrapping component is selected from the group consisting of 1,4,7,10-tetraazacyclododecane-1,4,7,10-tetraacetic acid (DOTA) and derivatives thereof; 1,4,8,11-tetraazacyclotetradecane (cyclam) and derivatives thereof; 1,4,7,10-tetraazacyclododecane (cyclen) and derivatives thereof; 1,4-ethano-1,4,8,11-tetraazacyclotetradecane (et-cyclam) and derivatives thereof; 1,4,7,11-tetraazacyclotetradecane (isocyclam) and derivatives thereof; 1,4,7,10-tetraazacyclotridecane ([13]aneN$_4$) and derivatives thereof; 1,4,7,10-tetraazacyclododecane-1,7-diacetic acid (DO2A) and derivatives thereof; 1,4,7,10-tetraazacyclododecane-1,4,7-triacetic acid (DO3A) and derivatives thereof; 1,4,7,10-tetraazacyclododecane-1,7-di(methanephosphonic acid) (DO2P) and derivatives thereof; 1,4,7,10-tetraazacyclododecane-1,4,7-tri(methanephosphonic acid) (DO3P) and derivatives thereof; 1,4,7,10-tetraazacyclododecane-1,4,7,10-tetra(methanephosphonic acid) (DOTP) and derivatives thereof; ethylenediaminetetraacetic acid (EDTA) and derivatives thereof; diethylene triamine pentaacetic acid (DTPA) and derivatives thereof; 1,4,8,11-tetraazacyclotetradecane-1,4,8,11-tetraacetic acid (TETA) and derivatives thereof, or other adamanzanes and derivates thereof.

In a preferred embodiment of the present invention, the agent-entrapping component is a chelator selected from the group consisting of 1,4,7,10-tetraazacyclododecane-1,4,7,10-tetraacetic acid (DOTA), 1,4,8,11-15 tetraazacyclotetradecane-1,4,8,11-tetraacetic acid (TETA), 1,4,7,10-tetraazacyclododecane-1,4,7,10-tetra(methanephosphonic acid) (DOTP), cyclam and cyclen.

In another embodiment of the described method for preparing nanoparticle compositions, the nanoparticle compositions are loaded with radionuclides and/or metal ions comprising an ionophoric compound capable of transporting metal ions across a bilayer. The ionophoric compound may be selected from the group: 2-hydroxyquinoline (carbostyril) 2-hydroxyquinoline-4-carboxylic acid; 6-chloro-2-hydroxyquinoline; 8-chloro-2-hydroxyquinoline; carbostyril 124; carbostyril 165; 4,6-dimethyl-2-hydroxyquinoline; 4,8-dimethyl-2-hydroxyquinoline; 1-cyano-1,2-dihydro-2-hydroxyquinoline or other 2-quinolinols compounds. (A and B) are ionophores of the invention that can be used to load radionuclides, in particularly copper isotopes, into nanoparticles. R can be, but is not limited to: H, F, Cl, Br, I, carbon chain ((C1-C24) saturated and unsaturated and with and without substituents other than H), OH, O—Z (where Z is a carbon chain (C1-C24) that can be saturated or unsaturated and with and without substituents other than H), S—H, S—Z, Se—H, Se—Z, NH2, NH—Z, N—Z2. X can be, but is not limited to: SH, SeH, O—Y (where Y is a carbon chain (C1-C8) that can be saturated or unsaturated and with and without substituents other than H), S—Y, Se—Y, NH2, NH—Y, N—Y2.

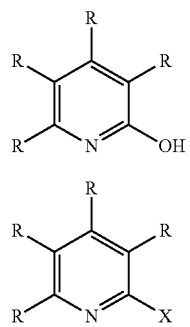

A

B

Using the disclosed method for preparing nanoparticle compositions, the nanoparticle compositions are loaded with a copper isotope utilizing an ionophoric compound capable of transporting metal entities, such as copper ions, across a bilayer, that is selected from the group, but not limited to: 8-hydroxyquinoline (oxine); 8-hydroxyquinoline β-D-galactopyranoside; 8-hydroxyquinoline β-D-glucopyranoside; 8-hydroxyquinoline glucuronide; 8-hydroxyquinoline-5-sulfonic acid; 8-hydroxyquinoline-β-D-glucuronide sodium salt; 8-quinolinol hemisulfate salt; 8-quinolinol N-oxide; 2-amino-8-quinolinol; 5,7-dibromo-8-hydroxyquinoline; 5,7-dichloro-8-hydroxyquinoline; 5,7-diiodo-8-hydroxyquinoline; 5,7-dimethyl-8-quinolinol; 5-amino-8-hydroxyquinoline dihydrochloride; 5-chloro-8-quinolinol; 5-nitro-8-hydroxyquinoline; 7-bromo-5-chloro-8-quinolinol; N-butyl-2,2'-imino-di(8-quinolinol); 8-hydroxyquinoline benzoate; 2-benzyl-8-hydroxyquinoline; 5-chloro-8-hydroxyquinoline hydrochloride; 2-methyl-8-quinolinol; 5-chloro-7-iodo-8-quinolinol; 8-hydroxy-5-nitroquinoline; 8-hydroxy-7-iodo-5-quinolinesulfonic acid; 5,7-dichloro-8-hydroxy-2-methylquinoline, and other quinolines (1-azanaphthalene, 1-benzazine) consisting chemical compounds and derivatives thereof. In a preferred embodiment the ionophoric compound is selected from the group consisting of: 8-hydroxyquinoline (oxine); 8-hydroxyquinoline β-D-galactopyranoside; 8-hydroxyquinoline β-D-glucopyranoside; 8-hydroxyquinoline glucuronide; 8-hydroxyquinoline-5-sulfonic acid; 8-hydroxyquinoline-β-D-glucuronide sodium salt; 8-quinolinol hemisulfate salt; 8-quinolinol N-oxide; 2-amino-8-quinolinol; 5,7-dibromo-8-hydroxyquinoline; 5,7-dichloro-8-hydroxyquinoline; 5,7-diiodo-8-hydroxyquinoline; 5,7-dimethyl-8-quinolinol; 5-amino-8-hydroxyquinoline dihydro-chloride; 5-chloro-8-quinolinol; 5-nitro-8-hydroxyquinoline; 7-bromo-5-chloro-8-quinolinol; N-butyl-2,2'-imino-di(8-quinolinol); 8-hydroxyquinoline benzoate; 2-benzyl-8-hydroxyquinoline; 5-chloro-8-hydroxyquinoline hydrochloride; 2-methyl-8-quinolinol; 5-chloro-7-iodo-8-quinolinol; 8-hydroxy-5-nitroquinoline; 8-hydroxy-7-iodo-5-quinolinesulfonic acid; 5,7-dichloro-8-hydroxy-2-methylquinoline, and other quinolines (1-azanaphthalene, 1-benzazine) consisting chemical compounds and derivatives thereof.

Structures A and B are ionophores of the invention that can be used to load copper radionuclides into nanoparticles. R can be, but is not limited to: H, F, Cl, Br, I, carbon chain (C1-C24) saturated and unsaturated and with and without substituents other than H, OH, O—Z (where Z is a carbon chain (C1-C24) that can be saturated or unsaturated and with and without substituents other than H), S—H, S—Z, Se—H, Se—Z, NH$_2$, NH—Z, N—Z2. X can be, but is not limited to: SH, SeH, O—Y (where Y is a carbon chain (C1-C8) that can be saturated or unsaturated and with and without substituents other than H), S—Y, Se—Y, NH2, NH—Y, N—Y2.

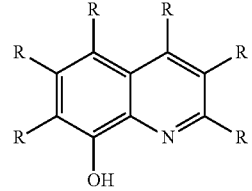

A

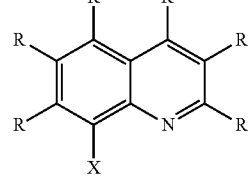

B

In a preferred embodiment of the present invention, the ionophoric compound capable of transporting metal ions across a bilayer is carbostyril (2-hydroxyquinoline, 2HQ). Thus, according to a preferred embodiment of the present invention, carbostyril is used as an ionophore for transportation of radionuclide being selected from the group consisting of Copper ($^{61}$Cu, $^{64}$Cu and $^{67}$Cu), Indium ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At) Lutetium ($^{177}$Lu), Actinium ($^{225}$Ac), Yttrium ($^{90}$Y), Antimony ($^{119}$Sb), Tin (117Sn, 113Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), and Radium ($^{223}$Ra, $^{224}$Ra).

In another preferred embodiment of the present invention, the ionophoric compound capable of transporting metal ions across a bilayer is oxine (8-hydroxyquinoline, 8HQ). Thus, according to a preferred embodiment of the present invention, oxine is used as an ionophore for transportation of copper isotopes.

Employing the disclosed method for preparing nanoparticle compositions, the result is entrapment of a radiolabeled agent within the nanoparticle composition, wherein the radiolabeled agent comprises a radionuclide selected from the group consisting of, but not limited to, $^{61}$Cu, $^{64}$Cu, and $^{67}$Cu. In one embodiment, the entrapped radionuclide is selected from the group consisting of, $^{61}$Cu, $^{64}$Cu and $^{67}$Cu.

In a further embodiment of the method according to the present invention, the radionuclide is a copper isotope selected from the group consisting of $^{61}$Cu, $^{64}$Cu, and $^{67}$Cu, and the ionophore is any ionophore defined as a compound capable of forming a complex with a radionuclide or a metal entity, and hereafter transporting this complex across a bilayer.

In one embodiment of the present invention, ionophoric compounds capable of transporting metal ions across a bilayer are A23187, hexamethylpropylene amine oxime (HMPAO) and derivatives thereof, diisopropyl iminodiacetic acid diisopropyl iminodiacetic acid (DISIDA) and derivatives thereof and other ionophoric compounds. Thus, according to a preferred embodiment of the present invention any ionophoric compound, such as, A23187, hexamethylpropylene amine oxime (HMPAO) and diisopropyl iminodiacetic acid diisopropyl iminodiacetic acid (DISIDA) are used for transportation of copper isotopes.

The method described here for preparing nanoparticle compositions loaded with radionuclides and/or metal entities is useful for diagnosing and/or treating a cancer or another in vivo abnormality in a subject such as a pathological condition associated with leaky blood vessels comprising: a) a nanoparticle composition having a vesicle forming component, an agent-entrapping component and a radiolabeled agent, wherein the agent-entrapping component and the radiolabeled agent are enclosed by the vesicle forming component, and the radiolabeled agent comprises a radionuclide; and b) administering the nanoparticle composition to the subject.

In one embodiment of the presented method for preparing radionuclide-containing nanoparticle compositions will produce nanoparticles which may be administered intravenously.

In a further embodiment the method for preparing nanoparticle compositions encompass controlling the liposome interior pH in the form of protonating or deprotonating the agent-entrapping component or the ionophore, thereby inducing effective loading of the radionuclide.

The described method for preparing nanoparticle compositions may further comprise a moiety attached to the external layer of the nanoparticle which is targeted for a cancerous disease, and in general, pathological conditions associated with leaky blood vessels.

In addition, the presently disclosed method for preparing nanoparticle compositions further comprises a compound with intracellular targeting properties, such as nuclear localization sequence peptide (NLS peptide), conjugated to the agent-entrapping component, thus entrapped within the nanoparticle composition.

Finally, the method providing the disclosed nanoparticle composition may further comprise measuring and detecting the amount of radiation emitted from the radionuclide entrapped within the nanoparticle composition.

In the following text, the invention is described as numbered items:

1. A nanoparticle composition comprising: a) a vesicle forming component; b) an agent-entrapping component enclosed by the vesicle forming component; and c) a copper isotope entrapped within the nanoparticle composition.
2. The nanoparticle composition of item 1, wherein said nanoparticle composition is radiolabeled.
3. The nanoparticle composition of any of the preceding items, wherein said copper isotope is a radionuclide.
4. The nanoparticle composition of item 3, wherein said entrapped radionuclide is selected from the group consisting of 61 Cu, 64Cu, and 67Cu.
5. The nanoparticle of any of the preceding items, wherein the entrapped copper isotope is an ion.
6. The nanoparticle of item 5, wherein said ion is selected from the group consisting of Cu(I) and Cu(II).
7. The nanoparticle composition of any of the preceding items, further comprising one or more isotopes different from copper.
8. The nanoparticle composition of any of the preceding items, further comprising one or more radionuclides different from copper.
9. The nanoparticle composition of any of the preceding items, wherein said vesicle forming component comprises one or more compounds selected from the group consisting of amphiphatic compounds.
10. The nanoparticle composition of item 9, wherein said amphiphatic compounds are selected from the group consisting of underivatized amphiphatic compounds, amphiphatic compounds derivatized with polyethylene glycol (PEG) and amphiphatic compounds derivatized with one or more polysaccharides.
11. The nanoparticle composition of any of the preceding items, wherein the vesicle forming component comprises both non-pegylated and pegylated versions of the same compound.
12. The nanoparticle composition of any of the items 9 or 10, wherein said amphiphatic compounds are selected from the group consisting of synthetic or naturally-occurring amphiphatic compounds which comprise a hydrophilic part and a hydrophobic part.
13. The nanoparticle composition of item 12, wherein said synthetic or naturally-occurring amphiphatic compound is selected from the group consisting of fatty acids, neutral fats, phosphatides, glycolipids, aliphatic alcohols, and steroids.
14. The nanoparticle composition of item 12, wherein said synthetic or naturally-occurring amphiphatic compound is selected from the group consisting of phosphatidylcholines such as 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2-palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine; phosphatidylethanolamines such as 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoyl-phosphatidylethanolamine; phosphatidylserines such as 1,2-dioleoyl-phosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl-2-oleoylphosphatidylserine and 1-stearoyl-2-oleoyl-phosphatidylserine; phosphatidylglycerols such as 1,2-dioleoyl-phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl-2-oleoyl-phosphatidylglycerol and 1-stearoyl-2-oleoyl-phosphatidylglycerol; pegylated lipids; pegylated phosphoholipids such as phosphatidyletha-nolamine-N-[methoxy(polyethyleneglycol)-1000], phosphatidyletha-nolamine-N-[methoxy(polyethyleneglycol)-2000], phosphatidylethanolamine-N-[methoxy(polyethylene glycol)-3000], phosphatidylethanolamine-N-[methoxy (polyethyleneglycol)-5000]; pegylated ceramides such as N-octanoyl-sphingosine-1-{succinyl[methoxy(polyethyleneglycol)1000]}, N-octanoyl-sphingosine-1-{succinyl [methoxy(polyethylene glycol)2000]}, N-octanoyl-sphingosine-1-{succinyl[methoxy(polyethyleneglycol)3000]}, N-octanoyl-sphingosine-1-{succinyl[methoxy(polyethyleneglycol)5000]}; lyso-phosphatidylcholines, lyso-phosphatidylethanolamines, lyso-phosphatidylglycerols, lyso-phosphatidylserines, cera-mides; sphingolipids; glycolipids such as ganglioside GMI; glucolipids; sul-phatides; phosphatidic acid, such as di-palmitoyl-glycero-phosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; polyoxyethylene fatty acids esters and polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; di-oleoyl-sn-glycerol; dipalmitoyl-succinylglycerol; 1,3-dipalmitoyl-2-succinylglycerol; 1-alkyl-2-acyl-phosphatidylcholines such as 1-hexadecyl-2-palmitoyl-phosphatidylcholine; 1-alkyl-2-acyl-phosphatidylethanolamines such as 1-hexadecyl-2-palmitoyl-phosphatidylethanolamine; 1-alkyl-2-acyl-phosphatidylserines such as 1-hexadecyl-2-palmitoyl-phosphatidylserine; 1-alkyl-2-acyl-phosphatidylglycerols such as 1-hexadecyl-2-palmitoyl-phosphatidylglycerol; 1-alkyl-2-alkyl-phosphatidylcholines such as 1-hexadecyl-2-hexadecyl-phosphatidylcholine; 1-alkyl-2-alkyl-phosphatidylethanolamines such as 1-hexadecyl-2-hexadecyl-phosphatidylethanolamine; 1-alkyl-2-alkyl-phosphatidylserines such as 1-hexadecyl-2-hexadecyl-phosphatidylserine; 1-alkyl-2-alkyl-phosphatidylglycerols such as 1-hexadecyl-2-hexadecyl-phosphatidylglycerol; N-Succinyl-dioctadecylamine; palmitoylhomocysteine; lauryltrimethylammonium bromide; cetyltrimethyl-ammonium bromide; myristyltrimethylammonium bromide; N-[1,2,3-dioleoyloxy)-propyl]-N,N,Ntrimethylammoniumchloride(DOTMA); 1,2-dioleoyloxy-3(trimethylammonium)propane (DOTAP); and 1,2-dioleoyl-c-(4'-trimethylammonium)-butanoyl-sn-glycerol (DOTB).

15. The nanoparticle composition of item 12, wherein said synthetic or naturally-occurring amphiphatic compound is selected from the group consisting of phospholipids, pegylated phospholipids and cholesterol.

16. The nanoparticle composition of item 12, wherein said synthetic or naturally-occurring amphiphatic compound is selected from the group consisting of 1,2-distearoyl-sn-glycero-3-phosphocholine (DSPC), cholesterol, and 1,2-distearoyl-sn-glycero-3-phosphoethanolamine-N-[methoxy (polyethylene glycol)-2000] (DSPE-PEG-2000).

17. The nanoparticle composition of item 16, wherein the molar ratio of 1,2-distearoyl-sn-glycero-3-phosphocholine (DSPC), cholesterol, and 1,2-distearoyl-sn-glycero-3-phosphoethanolamine-N-[methoxy (polyethylene glycol)-2000] (DSPE-PEG-2000) is 55:40:5.

18. The nanoparticle composition of any of the preceding items, wherein said agent-entrapping component comprises a compound selected from the group consisting of chelators, reducing agents and agents that form low solubility salts with copper ions.

19. The nanoparticle composition of any of the preceding items, wherein said agent-entrapping component comprises two different compounds selected from the group consisting of chelators, reducing agents and agents that form low solubility salts with copper ions.

20. The nanoparticle composition of any of the items 18 or 19, wherein said agent-entrapping component is a chelator selected from the group consisting of 1,4,7,10-tetraazacyclododecane ([12]aneN4); 1,4,7,10-tetraazacyclotridecane ([13]aneN4); 1,4,8,11-tetraazacyclotetradecane ([14]aneN4); 1,4,8,12-tetraazacyclopentadecane ([15]aneN4); 1,5,9,13-tetraazacyclohexadecane ([16]aneN4); ethylenediamine-tetraacetic-acid (EDTA), and diethylene-triamine-penta-acetic acid (DTPA).

21. The nanoparticle composition of any of the items 18 or 19, wherein said agent-entrapping component is a chelator selected from the group consisting of 1,4-ethano-1,4,8,11-tetraazacyclotetradecane (et-cyclam); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl) diacetic acid (DO2A); 2,2',2''-(1,4,7,10-tetraazacyclododecane-1,4,7-triyl) triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphonic acid) (DO2P); 1,4,7,10-tetraazacyclododecane-1,4,7-tri(methanephosphonic acid) (DO3P); 1,4,8,11-15 tetraazacyclotetradecane-1,4,8,11-tetraacetic acid (TETA); 2-(1,4,8,11-tetraazacyclotetradecane-1-yl)acetic acid (TE1A); 2,2'-(1,4,8,11-tetraazacyclotetradecane-1,8-diyl) diacetic acid (TE2A).

22. The nanoparticle composition of item 21, wherein said agent-entrapping component is selected from the group consisting of 1,4,7,10-tetraazacyclododecane-1,4,7,10-tetraacetic acid (DOTA); 1,4,8,11-15 tetraazacyclotetradecane-1,4,8,11-tetraacetic acid (TETA); 1,4,7,10-tetraazacyclododecane-1,4,7,10-tetra(methanephosphonic acid) (DOTP); cyclam, and cyclen.

23. The nanoparticle composition of item 22, wherein said agent-entrapping component is 1,4,7,10-tetraazacyclododecane-1,4,7,10-tetraacetic acid (DOTA).

24. The nanoparticle composition of item 18, wherein said agent-entrapping component is a reducing agent.

25. The nanoparticle composition of item 24, wherein said reducing agent is selected from the group consisting of ascorbic acid, glucose, fructose, glyceraldehyde, lactose, arabinose, maltose and acetol.

26. The nanoparticle composition of item 18, wherein said agent-entrapping component is a compound which forms a low solubility salt with copper.
27. The nanoparticle composition of item 26, wherein said compound which forms a low solubility salt with copper is selected from the group consisting of phosphate, oxalate and chloride.
28. The nanoparticle composition of any of the preceding items, further comprising a targeting moiety.
29. The nanoparticle composition of item 28, wherein said targeting moiety is attached to the surface of the nanoparticle composition via a lipid-anchoring molecule or PEG-conjugated lipid component.
30. The nanoparticle composition of item 28 or 29, wherein said targeting moiety attached to the surface of the nanoparticle composition is selected from the group consisting of antibodies, affibodies, and peptide components.
31. The nanoparticle composition of item 30, wherein said targeting moiety is an antibody selected from the group consisting of Rituximab, Trastuzumab, Cetuximab, LymphoCide, Vitaxin, Lym-1 and Bevacizumab.
32. The nanoparticle composition of item 30, wherein said targeting moiety is an affibody selected from the group consisting of anti-ErbB2 affibody, and anti-Fibrinogen affibody molecule.
33. The nanoparticle composition of item 30, wherein said targeting moiety is a peptide component selected from the group consisting of RGD, somatostatin and analogs thereof, and cell-penetrating peptides.
34. The nanoparticle composition of item 33, wherein said somatostatin analog is octreotate (TATE).
35. The nanoparticle composition of any of the preceding items, further comprising a controlled interior pH, thereby inducing effective encapsulation of the entrapped agent.
36. The nanoparticle composition of any of the preceding items, wherein the interior pH of the nanoparticle is within the range of 1 to 10, such as 1-2, for example 2-3, such as 3-4, for example 4-5, such as 5-6, for example 6-7, such as 7-8, for example 8-9, such as 9-10.
37. The nanoparticle composition of any of the preceding items, wherein the interior pH of the nanoparticle is within the range of the interior pH of the nanoparticle is within the range of 3 to 6, such as 3.0 to 3.5, for example 3.5 to 4.0, such as 4.0 to 4.5, for example 4.5 to 5.0, such as 5.0 to 5.5 for example 5.5 to 6.0.
38. The nanoparticle composition of any of the preceding items, further comprising a compound with intracellular targeting properties entrapped within the nanoparticle composition.
39. The nanoparticle composition of item 38, wherein the compound with intracellular targeting properties is a nuclear localization sequence peptide (NLS peptide) which is conjugated to the agent-entrapping component.
40. The nanoparticle composition of any of the preceding items, wherein the diameter of the nanoparticle is in the range of 30 nm to 300 nm; such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm.
41. The nanoparticle composition of any of the preceding items, wherein the diameter of the nanoparticle is less than 120 nm.
42. The nanoparticle composition of any of the preceding items, wherein the diameter of the nanoparticle is larger than 80 nm.
43. The nanoparticle composition of any of the preceding items, wherein the entrapped agent has been loaded into the nanoparticle composition using an ionophore.
44. The nanoparticle composition of any of the preceding items, further comprising an ionophore.
45. The nanoparticle composition of any of the preceding items, further comprising trace amounts of an ionophore.
46. The nanoparticle composition of any of the items 43-45, wherein said agent-entrapping component is a chelator (e.g. DOTA) and the reaction of transfer of copper from the ionophore to the chelating agent is spontaneous either inherently or as a result of a high concentration of chelating agent within the nanoparticle composition.
47. The nanoparticle composition of any of the items 43-46, wherein said agent-entrapping component is a chelator (e.g. DOTA) and the reaction of transfer of copper from the ionophore to the chelating agent is spontaneous as a result of a high concentration of chelating agent within the nanoparticle composition.
48. The nanoparticle composition of any of the preceding items, wherein the stability of the radiolabeled nanoparticles is such that less than 20% leakage of radioactivity is observed following 24 hours incubation in human serum at 37° C. followed by a purification step such as size exclusion chromatography (SEC), ion-exchange chromatography or dialysis to separate the radiolabeled nanoparticles from leaked radionuclide, for example less than 15% leakage, such as less than 12% leakage, for example less than 10% leakage, such as less than 8% leakage, for example less than 6% leakage, such as less than 4% leakage, for example less than 3% leakage, such as less than 2% leakage, for example less than 1% leakage.
49. The nanoparticle composition of any of the preceding items for use in diagnosing pathological conditions associated with leaky blood vessels.
50. The nanoparticle composition of any of the preceding items for use in diagnosing cancer.
51. The nanoparticle composition of any of the preceding items for use in positron emission tomography (PET) scanning or single photon emission computed tomography (SPECT) scanning.
52. The nanoparticle composition of any of the preceding items for use a medicament.
53. The nanoparticle composition of any of the preceding items for use in cancer therapy.
54. A method for preparing nanoparticle compositions loaded with copper isotopes comprising: a) providing a nanoparticle composition comprising a vesicle forming component and an agent-entrapping component enclosed by said vesicle forming component; b) providing a component for transporting the copper isotopes over the vesicle membranes; and c) entrapping the copper isotopes within the interior of the nanoparticle composition.
55. The method of item 54, wherein said nanoparticle composition is radio-labeled.
56. The method of any of the items 54 or 55, wherein said copper isotope is a radionuclide.
57. The method of item 56, wherein said radionuclide is selected from the group consisting of 61 Cu, 64Cu, and 67Cu.
58. The method of any of the items 54-57, wherein said copper isotope is an ion.
59. The method of item 58, wherein said ion is selected from the group consisting of Cu(I) and Cu(II).
60. The method of any of the items 54-59, wherein said component for transporting copper isotopes over said vesicle membranes is an ionophore.

61. The method of item 60, wherein said ionophore is selected from the group consisting of quinoline derivatives of formula A

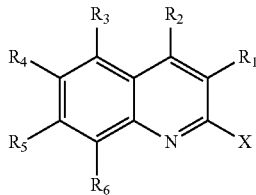

a stereoisomer thereof or a mixture of its stereoisomers, or a pharmaceutically acceptable salt thereof, wherein
X represents hydroxy (OH), amino (NH2) or sulphydryl (SH) and wherein R1, R2, R3, R4, R5, and R6 independently of each other, represent substituents selected from the group consisting of hydrogen (H), halo (Cl, Br, I), methyl (CH3), ethyl (C2H5), propyl (C3H8), butyl (C4H11), amino (NH2), dimethylamino (N(CH3)2), hydroxy (OH), cyano (CN), sulphydryl (SH), carboxy (COOH), β-D-galactopyranoside (C6O6H11), glucoronide (C6H9O7), sulphonyl (SO3H), benzoyl (C6H4COOH), and benzyl (C6H5(CH2)), and wherein R1 and R2, R2 and R3, R3 and R4, R4 and R5, or R5 and R6—together with the aromatic ring to which they are attached—may form a benzo-fused carbocyclic aromatic ring or an aliphatic ring.

62. The method of item 61, wherein said ionophore is selected from the group consisting of derivatives of A, a stereoisomer thereof or a mixture of its stereoisomers, or a pharmaceutically acceptable salt thereof, wherein X represents hydroxy (OH).

63. The method of any of the items 61 or 62, wherein R1 represents hydrogen (H).

64. The method of any of the items 61 or 62, wherein R1 and R3 represent hydrogen (H).

65. The method of any of the items 61 or 62, wherein R1, R3 and R5 represent hydrogen (H).

66. The method of any of the items 61 or 62, wherein R1, R3, R4 and R5 represent hydrogen (H).

67. The method of any of the items 61 or 62, wherein R1, R3, R4, R5 and R6 represent hydrogen (H).

68. The method of any of the items 61 or 62, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl (CH3), ethyl (C2H5), propyl (C3H8), butyl (C4H11), amino (NH2), dimethylamino (N(CH3)2), hydroxy (OH), cyano (CN), sulphydryl (SH), carboxy (COOH), β-D-glucopyranoside (C6O6H11), and sulphonyl (SO3H).

69. The method of any of the items 61 or 62, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl (CH3), ethyl (C2H5), propyl (C3H8), amino (NH2), dimethylamino (N(CH3)2), hydroxy (OH), cyano (CN), sulphydryl (SH), carboxy (COOH), and sulphonyl (SO3H).

70. The method of any of the items 61 or 62, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl (CH3), ethyl (C2H5), propyl (C3H8), amino (NH2), hydroxy (OH), sulphydryl (SH), and carboxy (COOH).

71. The method of any of the items 61 or 62, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl (CH3), ethyl (C2H5), amino (NH2), hydroxy (OH), sulphydryl (SH).

72. The method of any of the items 61 or 62, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), ethyl (C2H5), amino (NH2), and hydroxy (OH).

73. The method of any of the items 61 or 62, wherein said ionophore is selected from the group consisting of 2-hydroxyquinoline-4-carboxylic acid, 6-chloro-2-hydroxyquinoline, 8-chloro-2-hydroxyquinoline, 7-amino-4-methyl-2-hydroxyquinoline (carbostyril 124), 7-dimethylamino-4-methyl-2-hydroxyquinoline (carbostyril 165), 4,6-dimethyl-2-hydroxyquinoline, 4,8-dimethyl-2-hydroxyquinoline, or other 2-quinolinols compounds or stereoisomer thereof or a mixture of its stereoisomers, or a pharmaceutically acceptable salt thereof.

74. The method of any of the items 61 or 62, wherein said ionophore is 2-hydroxyquinoline (carbostyril).

75. The method of item 60, wherein said ionophore is selected from the group consisting of quinoline derivatives of formula B

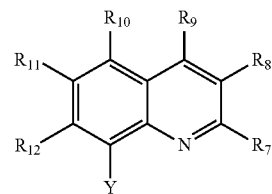

a stereoisomer thereof or a mixture of its stereoisomers, or a pharmaceutically acceptable salt thereof, wherein
Y represents hydroxy (OH), amino (NH2), or sulphydryl (SH) and wherein R7, R8, R9, R10, R11, and R12 independently of each other, represent substituents selected from the group consisting of hydrogen (H), halo (Cl, Br, I), methyl (CH3), ethyl (C2H5), propyl (C3H8), butyl (C4H11), amino (NH2), nitro (NO2), dimethylamino (N(CH3)2), hydroxy (OH), cyano (CN), carboxy (COOH), β-D-glucopyranoside (C6O6H11), sulphydryl (SH), glucoronide (C6H9O7), sulphonyl (SO3H), benzoyl (C6H4COOH), and benzyl (C6H5 (CH2)), and wherein R7 and R8, R8 and R9, R9 and R10, R10 and R11, or R11 and R12—together with the aromatic ring to which they are attached—may form a benzo-fused carbocyclic aromatic ring or an aliphatic ring.

76. The method of item 75, wherein said ionophore is selected from the group consisting of derivatives of B, a stereoisomer thereof or a mixture of its stereoisomers, or a pharmaceutically acceptable salt thereof, wherein Y represents hydroxy (OH).

77. The method of any of the items 75 or 76, wherein R8 represents hydrogen (H).

78. The method of any of the items 75 or 76, wherein R8 and R9 represent hydrogen (H).

79. The method of any of the items 75 or 76, wherein R8, R9 and R11 represent hydrogen (H).

80. The method of any of the items 75 or 76, wherein R7, R8, R9 and R11 represent hydrogen (H).

81. The method of any of the items 75 or 76, wherein R7, R8, R9, R11 and R12 represent hydrogen (H).

82. The method of any of the items 75 or 76, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), propyl (C3H8), butyl (C4H11), amino (NH2), dimethylamino (N(CH3)2), hydroxy (OH), cyano (CN), carboxy (COOH), β-D-glucopyranoside (C6O6H11), sulphydryl (SH), and sulphonyl (SO3H).

83. The method of any of the items 75 or 76, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), propyl (C3H8), amino (NH2), dimethylamino (N(CH3)2), hydroxy (OH), cyano (CN), carboxy (COOH), sulphydryl (SH), and sulphonyl (SO3H).

84. The method of any of the items 75 or 76, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), propyl (C3H8), amino (NH2), hydroxy (OH), sulphydryl (SH), and carboxy (COOH).

85. The method of any of the items 75 or 76, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), hydroxy (OH), carboxy (COOH), and sulphydryl (SH).

86. The method of any of the items 75 or 76, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), ethyl (C2H5), amino (NH2), and hydroxy (OH).

87. The method of any of the items 75 or 76, wherein said ionophore is selected from the group consisting of 8-hydroxyquinoline (oxine), 8-hydroxyquinoline β-D-galactopyranoside, 8-hydroxyquinoline β-D-glucopyranoside, 8-hydroxyquinoline glucuronide, 8-hydroxyquinoline-5-sulfonic acid, 2-amino-8-quinolinol, 5,7-dibromo-8-hydroxyquinoline, 5,7-dichloro-8-hydroxyquinoline, 5,7-di-iodo-8-hydroxyquinoline, 5,7-dimethyl-8-quinolinol, 5-chloro-8-quinolinol, 5-nitro-8-hydroxyquinoline, 7-bromo-5-chloro-8-quinolinol, 8-hydroxyquinoline benzoate, 2-benzyl-8-hydroxyquinoline, 2-methyl-8-quinolinol, 5-chloro-7-iodo-8-quinolinol, 8-hydroxy-5-nitroquinoline, 8-hydroxy-7-iodo-5-quinolinesulfonic acid, 5,7-dichloro-8-hydroxy-2-methylquinoline.

88. The method of any of the items 75 or 76, wherein said ionophore is 8-hydroxyquinoline (oxine).

89. The method of any of the items 54-88, wherein the nanoparticle composition is a nanoparticle composition according to any of the items 1-48.

90. The method of any of the items 54-89, wherein said agent-entrapping component is a chelator and where the molar ratio of ionophore to chelator is in the range of 1:1 to 1:10000000, for example 1:5, such as 1:10, for example 1:50, such as 1:100, for example 1:250, such as 1:500, for example 1:1000, such as 1:5000, for example 1:10000, such as 1:50000, for example 1:100000, such as 1:500000, for example 1:1000000, such as 1:5000000, for example 1:10000000.

91. The method of any of the items 54-90, wherein the interior pH of the nanoparticle is within the range of 1 to 10, such as 1-2, for example 2-3, such as 3-4, for example 4-5, such as 5-6, for example 6-7, such as 7-8, for example 8-9, such as 9-10.

92. The method of any of the items 54-91, wherein the interior pH of the nanoparticle is within the range of the interior pH of the nanoparticle is within the range of 3 to 6, such as 3.0 to 3.5, for example 3.5 to 4.0, such as 4.0 to 4.5, for example 4.5 to 5.0, such as 5.0 to 5.5 for example 5.5 to 6.0.

93. The method of any of the items 54-90, wherein the purity of the generated radiolabeled nanoparticles is verified using size exclusion chromatography (SEC), ion-exchange chromatography or dialysis.

94. The method of any of the items 54-93, wherein the generated radio-labeled nanoparticles are purified using size exclusion chromatography (SEC), ion-exchange chromatography or dialysis.

95. The method of any of the items 54-94, wherein entrapment of copper is in the range of 30% to 95% as assayed using size exclusion chromatography (SEC), ion-exchange chromatography or dialysis.

96. The method of any of the items 54-94, wherein entrapment of copper is greater than 35% as assayed using size exclusion chromatography (SEC), ion-exchange chromatography or dialysis, for example higher than 40%, such as higher than 50%, for example higher than 60%, such as higher than 65%, for example higher than 70%, such as higher than 75%, for example higher than 80%, such as higher than 85%, for example higher than 90%, such as higher than 95%.

97. The method of any of the items 54-96, wherein the stability of the radiolabeled nanoparticles is such that less than 20% leakage of radioactivity is observed following 24 hours incubation in human serum at 37° C. followed by a purification step such as size exclusion chromatography (SEC), ion-exchange chromatography or dialysis to separate the radiolabeled nanoparticles from leaked radionuclide, for example less than 15% leakage, such as less than 12% leakage, for example less than 10% leakage, such as less than 8% leakage, for example less than 6% leakage, such as less than 4% leakage, for example less than 3% leakage, such as less than 2% leakage, for example less than 1% leakage.

98. The method of any of the items 54-97, wherein the size of the nanoparticle remains essentially unaltered following loading of the nanoparticles with copper.

99. The method of any of the items 54-97, wherein the size of the nanoparticle compositions is altered less than 20% following loading of the nanoparticles with copper isotopes, for example less than 17%, such as less than 14%, for example less than 11%, such as less than 8%, for example less than 5%, such as less than 2%.

100. The method of any of the items 54-98, wherein the zeta potential is altered less than 20% following loading of the nanoparticles with copper, such as 18%, for example less than 16%, such as less than 14%, for example less than 12%, such as less than 10%.

101. The method of any of the items 54-100, further comprising measuring and detecting the amount of radiation emitted from the radionuclide within the nanoparticle composition.

102. The method of any of the items 54-101, further comprising use of the nanoparticle composition for diagnosis or treatment.

103. The method of item 102, wherein the nanoparticle composition is administered orally.

104. The method of item 102, wherein the nanoparticle composition is administered intravenously.

105. The method of any of the items 102-104, wherein said method is used in diagnosing pathological conditions associated with leaky blood vessels.

106. The method of any of the items 102-104, wherein said method is used in diagnosing cancer.

107. A kit of parts for preparing a nanoparticle composition according to any of the items 1-48, said kit comprising
    a. a nanoparticle composition comprising
        i. a vesicle forming component, and
        ii. an agent-entrapping component enclosed by the vesicle forming component; and
    b. a composition containing an ionophore,
    wherein part a or part b further comprises a copper isotope.

108. A kit of parts for preparing a nanoparticle composition according to any of the items 1-48, said kit comprising
    a. a nanoparticle composition comprising
        i. a vesicle forming component, and
        ii. an agent-entrapping component enclosed by the vesicle forming component; and
    b. a composition containing an ionophore,
    c. a composition containing a copper isotope.

109. A kit of parts for preparing a nanoparticle composition according to any of the items 1-48, said kit comprising
a. a nanoparticle composition comprising
i. a vesicle forming component, and
ii. an agent-entrapping component enclosed by the vesicle forming component; and
iii. an ionophore,
b. a composition containing a copper isotope.

110. The kit of parts of any of the items 107-109, wherein the copper isotope is a radionuclide.

111. The kit of parts of any of the items 107-110, wherein said ionophore is selected from the group consisting of quinoline derivatives of formula A

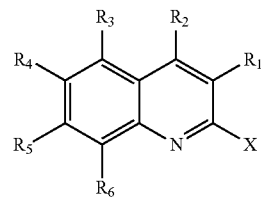

a stereoisomer thereof or a mixture of its stereoisomers, or a pharmaceutically acceptable salt thereof, wherein
X represents hydroxy (OH), sulphydryl (SH) or amino (NH2) and wherein R1, R2, R3, R4, R5, and R6 independently of each other, represent substituents selected from the group consisting of hydrogen (H), halo (Cl, Br, I), methyl (CH3), ethyl (C2H5), propyl (C3H8), butyl (C4H11), amino (NH2), dimethylamino (N(CH3)2), hydroxy (OH), cyano (CN), sulphydryl (SH), carboxy (COOH), β-D-galactopyranoside (C6O6H11), glucoronide (C6H9O7), sulphonyl (SO3H), benzoyl (C6H4COOH), and benzyl (C6H5(CH2)), and wherein R1 and R2, R2 and R3, R3 and R4, R4 and R5, or R5 and R6—together with the aromatic ring to which they are attached—may form a benzo-fused carbocyclic aromatic ring or an aliphatic ring.

112. The kit of parts of item 111, wherein said ionophore is selected from the group consisting of derivatives of A, a stereoisomer thereof or a mixture of its stereoisomers, or a pharmaceutically acceptable salt thereof, wherein X represents hydroxy (OH).

113. The kit of parts of any of the items 111 or 112, wherein R1 represents hydrogen (H).

114. The kit of parts of any of the items 111 or 112, wherein R1 and R3 represent hydrogen (H).

115. The kit of parts of any of the items 111 or 112, wherein R1, R3 and R5 represent hydrogen (H).

116. The kit of parts of any of the items 111 or 112, wherein R1, R3, R4 and R5 represent hydrogen (H).

117. The kit of parts of any of the items 111 or 112, wherein R1, R3, R4, R5 and R6 represent hydrogen (H).

118. The kit of parts of any of the items 111 or 112, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl (CH3), ethyl (C2H5), propyl (C3H8), butyl (C4H11), amino (NH2), dimethylamino (N(CH3)2), hydroxy (OH), cyano (CN), sulphydryl (SH), carboxy (COOH), β-D-glucopyranoside (C6O6H11), and sulphonyl (SO3H).

119. The kit of parts of any of the items 111 or 112, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl (CH3), ethyl (C2H5), propyl (C3H8), amino (NH2), dimethylamino (N(CH3)2), hydroxy (OH), cyano (CN), sulphydryl (SH), carboxy (COOH), and sulphonyl (SO3H).

120. The kit of parts of any of the items 111 or 112, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl (CH3), ethyl (C2H5), propyl (C3H8), amino (NH2), hydroxy (OH), sulphydryl (SH), and carboxy (COOH).

121. The kit of parts of any of the items 111 or 112, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), halo (Cl, Br, I), methyl ($CH_3$), ethyl ($C_2H_5$), amino ($NH_2$), hydroxy (OH), sulphydryl (SH).

122. The kit of parts of any of the items 111 or 112, wherein said ionophore is selected from the group consisting of derivatives of A, a stereoisomer thereof or a mixture of its stereoisomers, or a pharmaceutically acceptable salt thereof, wherein R1, R2, R3, R4, R5, and R6 independently of each other, represent substituents selected from the group consisting of hydrogen (H), ethyl ($C_2H_5$), amino ($NH_2$), and hydroxy (OH).

123. The kit of parts of any of the items 111 or 112, wherein said ionophore is selected from the group consisting of 2-hydroxyquinoline-4-carboxylic acid, 6-chloro-2-hydroxyquinoline, 8-chloro-2-hydroxyquinoline, 7-amino-4-methyl-2-hydroxyquinoline (carbostyril 124), 7-dimethylamino-4-methyl-2-hydroxyquinoline (carbostyril 165), 4,6-dimethyl-2-hydroxyquinoline, 4,8-dimethyl-2-hydroxyquinoline, or other 2-quinolinols compounds or stereoisomer thereof or a mixture of its stereo-isomers, or a pharmaceutically acceptable salt thereof.

124. The kit of parts of any of the items 111 or 112, wherein said ionophore is 2-hydroxyquinoline (carbostyril).

125. The kit of parts of item 111, wherein said ionophore is selected from the group consisting of quinoline derivatives of formula B

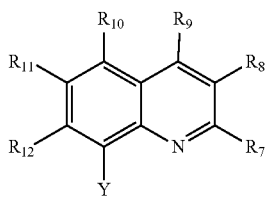

B a stereoisomer thereof or a mixture of its stereoisomers, or a pharmaceutically acceptable salt thereof, wherein
Y represents hydroxy (OH), sulphydryl (SH), or amino (NH2) and wherein R7, R8, R9, R10, R11, and R12 independently of each other, represent substituents selected from the group consisting of hydrogen (H), halo (Cl, Br, I), methyl (CH3), ethyl (C2H5), propyl (C3H8), butyl (C4H11), amino (NH2), nitro (NO2), dimethylamino (N(CH3)2), hydroxy (OH), cyano (CN), carboxy (COOH), β-D-glucopyranoside (C6O6H11), glucoronide (C6H9O7), sulphonyl (SO3H), benzoyl (C6H5COO), and benzyl (C6H5(CH2)), and wherein R7 and R8, R8 and R9, R9 and R10, R10 and R11, or R11 and R12—together with the aromatic ring to which they are attached—may form a benzo-fused carbocyclic aromatic ring or an aliphatic ring.

126. The kit of parts of item 125, wherein said ionophore is selected from the group consisting of derivatives of B, a stereoisomer thereof or a mixture of its stereoisomers, or a pharmaceutically acceptable salt thereof, wherein Y represents hydroxy (OH).

127. The kit of parts of any of the items 125 or 126, wherein R8 represents hydrogen (H).

128. The kit of parts of any of the items 125 or 126, wherein R8 and R9 represent hydrogen (H).

129. The kit of parts of any of the items 125 or 126, wherein R8, R9 and R11 represent hydrogen (H).

130. The kit of parts of any of the items 125 or 126, wherein R7, R8, R9 and R11 represent hydrogen (H).

131. The kit of parts of any of the items 125 or 126, wherein R7, R8, R9, R11 and R12 represent hydrogen (H).

132. The kit of parts of any of the items 125 or 126, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), propyl (C3H8), butyl (C4H11), amino (NH2), dimethylamino (N(CH3)2), hydroxy (OH), cyano (CN), carboxy (COOH), β-D-glucopyranoside (C6O6H11), sulphydryl (SH), and sulphonyl (SO3H).

133. The kit of parts of any of the items 125 or 126, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), propyl (C3H8), amino (NH2), dimethylamino (N(CH3)2), hydroxy (OH), cyano (CN), carboxy (COOH), sulphydryl (SH), and sulphonyl (SO3H).

134. The kit of parts of any of the items 125 or 126, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), propyl (C3H8), amino (NH2), hydroxy (OH), sulphydryl (SH), and carboxy (COOH).

135. The kit of parts of any of the items 125 or 126, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), halo (Cl, Br, I), methyl (CH3), ethyl (C2H5), hydroxy (OH), carboxy (COOH), and sulphydryl (SH).

136. The kit of parts of any of the items 125 or 126, wherein said ionophore is selected from the group consisting of derivatives of B, a stereoisomer thereof or a mixture of its stereoisomers, or a pharmaceutically acceptable salt thereof, wherein R7, R8, R9, R10, R11, and R12 independently of each other, represent substituents selected from the group consisting of hydrogen (H), ethyl ($C_2H_5$), amino ($NH_2$), and hydroxy (OH).

137. The kit of parts of any of the items 125 or 126, wherein said ionophore is selected from the group consisting of 8-hydroxyquinoline (oxine), 8-hydroxyquinoline β-D-galactopyranoside, 8-hydroxyquinoline β-D-glucopyranoside, 8-hydroxyquinoline glucuronide, 8-hydroxyquinoline-5-sulfonic acid, 2-amino-8-quinolinol, 5,7-dibromo-8-hydroxyquinoline, 5,7-dichloro-8-hydroxyquinoline, 5,7-diiodo-8-hydroxyquinoline, 5,7-dimethyl-8-quinolinol, 5-chloro-8-quinolinol, 5-nitro-8-hydroxyquinoline, 7-bromo-5-chloro-8-quinolinol, 8-hydroxyquinoline benzoate, 2-benzyl-8-hydroxyquinoline, 2-methyl-8-quinolinol, 5-chloro-7-iodo-8-quinolinol, 8-hydroxy-5-nitroquinoline, 8-hydroxy-7-iodo-5-quinolinesulfonic acid, 5,7-dichloro-8-hydroxy-2-methylquinoline.

138. The kit of parts of any of the items 125 or 126, wherein said ionophore is 8-hydroxyquinoline (oxine).

139. The kit of parts of any of the items 107-138, wherein said agent-entrapping component is a chelator (e.g. DOTA) and the reaction of transfer of copper from the ionophore to the chelating agent is spontaneous, either inherently or as a result of a high concentration of chelating agent within the nanoparticle composition.

140. The kit of parts of any of the items 107-138, wherein said agent-entrapping component is a chelator (e.g. DOTA) and the reaction of transfer of copper from the ionophore to the chelating agent is spontaneous as a result of a high concentration of chelating agent within the nanoparticle composition.

141. The kit of parts of any of the items 107-140, wherein said agent-entrapping component is a chelator and where the molar ratio of ionophore to chelator is in the range of 1:1 to 1:10000000, for example 1:5, such as 1:10, for example 1:50, such as 1:100, for example 1:250, such as 1:500, for example 1:1000, such as 1:5000, for example 1:10000, such as 1:50000, for example 1:100000, such as 1:500000, for example 1:1000000, such as 1:5000000, for example 1:10000000.

142. The kit of parts of any of the items 107-141, wherein the copper isotope is delivered in the form of a salt.

143. The kit of parts of any of the items 107-142, wherein the copper isotope is delivered in the form of a lyophilized salt.

144. The kit of parts of any of the items 107-141, wherein the copper isotope is delivered as an aqueous solution of ions.

145. The kit of parts of any of the items 107-144, further comprising a test for determining efficiency of encapsulation.

146. The kit of parts of any of the items 107-145, wherein said parts can be mixed 0-5 hours before use; such as 0-4 hours before use, for example 0-3 hours before use, such as 0-2 hours before use, for example 0-1 hour before use, such as immediately before use.

147. The kit of parts according to any of the items 107-146, for preparing a nanoparticle composition of any of the items 1 to 53.

148. The kit of parts of any of the items 107-147, for use in diagnosing pathological conditions associated with leaky blood vessels.

149. The kit of parts of any of the items 107-147, for use as a medicament.

150. The kit of parts of any of the items 107-147, for use in diagnosing cancer.

151. The kit of parts of any of the items 107-147, for use in positron emission tomography (PET) scanning or single photon emission computed tomography (SPECT) scanning.

152. A method for preparing nanoparticle compositions loaded with radionuclides comprising: a) providing a nanoparticle composition comprising a vesicle forming component and an agent-entrapping component enclosed by said vesicle forming component; b) providing a component for transporting the radionuclides over the vesicle membranes, said component being an ionophore according to any of the items 61-74 (formula A); and c) entrapping the radionuclides within the interior of the nanoparticle composition.

153. The method of item 152, wherein said radionuclide is selected from the group consisting of Copper (61 Cu, 64Cu, and 67Cu), Indium (111 In), Technetium (99 mTc), Rhenium (188Re), Gallium (67Ga, 68Ga), and Lutetium (177Lu), Actinium (225Ac), Yttrium (90Y), Antimony (119Sb), Tin (117Sn, 113Sn), Dysprosium (159Dy), Cobalt (56Co), Iron (59Fe), Ruthenium (97Ru, 103Ru), Palladium (103Pd), Cadmium (115Cd), Tellurium (118Te, 123Te), Barium (131 Ba, 140Ba), Gadolinium (149Gd, 151Gd), Terbium (160Tb), Gold (198Au, 199Au), Lanthanum (140La), and Radium (223Ra, 224Ra).

154. The method of item 152, wherein said radionuclide is selected from the group consisting of Copper (61 Cu, 64Cu, and 67Cu), Indium (111 In), Technetium (99 mTc), Rhenium (188Re), Gallium (67Ga, 68Ga), Actinium (225Ac), Yttrium (90Y), Antimony (119Sb), and Lutetium (177Lu).

155. The method of any of the items 152-154, wherein said radionuclide appears in the form of ions such as monovalent cations, for example divalent cations, such as trivalent cations, for example tetravalent cations, such as pentavalent cations, for example hexavalent cations such as heptavalent cations.

156. The method of any of the items 152-155, wherein said vesicle forming component comprises one or more of the compounds selected from the group consisting of amphiphatic compounds.

157. The method of item 156, wherein said amphiphatic compounds are selected from the group consisting of underivatized amphiphatic compounds, amphiphatic compounds derivatized with polyethylene glycol (PEG) and amphiphatic compounds derivatized with one or more polysaccharides.

158. The method of any of the items 156 or 157, wherein the vesicle forming component comprises both non-pegylated and pegylated versions of the same vesicle forming compound.

159. The method of any of the items 156 or 157, wherein said amphiphatic compounds are selected from the group consisting of synthetic or naturally-occurring amphiphatic compounds which comprise a hydrophilic part and a hydrophobic part.

160. The method of item 159, wherein said synthetic or naturally-occurring amphiphatic compound is selected from the group consisting of fatty acids, neutral fats, phosphatides, glycolipids, aliphatic alcohols, and steroids.

161. The method of item 159, wherein said synthetic or naturally-occurring amphiphatic compound is selected from the group consisting of phosphatidylcholines such as 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2-palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine; phosphatidylethanolamines such as 1,2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoyl-phosphatidylethanolamine; phosphatidylserines such as 1,2-dioleoyl-phosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl-2-oleoyl-phosphatidylserine and 1-stearoyl-2-oleoyl-phosphatidylserine; phosphatidylglycerols such as 1,2-dioleoyl-phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl-2-oleoyl-phosphatidylglycerol and 1-stearoyl-2-oleoyl-phosphatidylglycerol; pegylated lipids; pegylated phosphoholipids such as phosphatidyletha-nolamine-N-[methoxy(polyethyleneglycol)-1000], phosphatidylethanolamine-N-[methoxy(polyethyleneglycol)-2000], phosphatidylethanolamine-N-[methoxy(polyethylene glycol)-3000], phosphatidylethanolamine-N-[methoxy(polyethyleneglycol)-5000]; pegylated ceramides such as N-octanoyl-sphingosine-1-{succinyl[methoxy(polyethyleneglycol) 1000]}, N-octanoyl-sphingosine-1-{succinyl[methoxy (polyethylene glycol)2000]}, N-octanoyl-sphingosine-1-{succinyl[methoxy(polyethyleneglycol)3000]}, N-octanoyl-sphingosine-1-{succinyl[methoxy (polyethyleneglycol)5000]}; lyso-phosphatidylcholines, lyso-phosphatidylethanolamines, lyso-phosphatidylglycerols, lyso-phosphatidylserines, cera-mides; sphingolipids; glycolipids such as ganglioside GMI; glucolipids; sulphatides; phosphatidic acid, such as di-palmitoyl-glycerophosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; polyoxyethylene fatty acids esters and polyoxyethylene fatty acids alcohols; polyoxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropylene fatty acid polymers; polyoxyethylene fatty acid stearates; di-oleoyl-sn-glycerol; dipalmitoyl-succinyl glycerol; 1,3-dipalmitoyl-2-succinylglycerol; 1-alkyl-2-acyl-phosphatidylcholines such as 1-hexadecyl-2-palmitoyl-phosphatidylcholine; 1-alkyl-2-acyl-phosphatidylethanolamines such as 1-hexadecyl-2-palmitoyl-phosphatidylethanolamine; 1-alkyl-2-acyl-phosphatidylserines such as 1-hexadecyl-2-palmitoyl-phosphatidylserine; 1-alkyl-2-acyl-phosphatidylglycerols such as 1-hexadecyl-2-palmitoyl-phosphatidylglycerol; 1-alkyl-2-alkyl-phosphatidylcholines such as 1-hexadecyl-2-hexadecyl-phosphatidylcholine; 1-alkyl-2-alkyl-phosphatidylethanolamines such as 1-hexadecyl-2-hexadecyl-phosphatidylethanolamine; 1-alkyl-2-alkyl-phosphatidylserines such as 1-hexadecyl-2-hexadecyl-phosphatidylserine; 1-alkyl-2-alkyl-phosphatidylglycerols such as 1-hexadecyl-2-hexadecyl-phosphatidylglycerol; N-Succinyl-dioctadecylamine; palmitoylhomocysteine; lauryltrimethylammonium bromide; cetyltrimethyl-ammonium bromide; myristyltrimethylammonium bromide; N-[1,2,3-dioleoyloxy)-propyl]-N,N,N-trimethylammoniumchloride (DOTMA); 1,2-dioleoyloxy-3 (trimethylammonium)propane (DOTAP); and 1,2-dioleoyl-c-(4'-trimethylammonium)-butanoyl-sn-glycerol (DOTB).

162. The method of item 159, wherein said synthetic or naturally-occurring amphiphatic compound is selected from the group consisting of phospholipids, pegylated phospholipids and cholesterol.

163. The method of item 162, wherein said synthetic or naturally-occurring amphiphatic compound is selected from the group consisting of 1,2-distearoyl-sn-glycero-3-phosphocholine (DSPC), cholesterol, and 1,2-distearoyl-sn-glycero-3-phosphoethanolamine-N-[methoxy (polyethylene glycol)-2000] (DSPE-PEG-2000).

164. The method of item 163, wherein the molar ratio of 1,2-distearoyl-sn-glycero-3-phosphocholine (DSPC), cholesterol, and 1,2-distearoyl-sn-glycero-3-phosphoethanolamine-N-[methoxy (polyethylene glycol)-2000] (DSPE-PEG-2000) is 55:40:5.

165. The method of any of the items 152-164, wherein said agent-entrapping component is selected from the group consisting of chelators, reducing agents and agents that form low solubility salts with said radionuclides.

166. The method of any of the items 152-165, wherein said agent-entrapping component comprises two different compounds selected from the group consisting of chelators, reducing agents and agents that form low solubility salts said radionuclides.

167. The method of any of the items 152-166, wherein said agent-entrapping component is a chelator selected from the group consisting of 1,4,7,10-tetraazacyclododecane ([12]aneN4); 1,4,7,10-tetraazacyclotridecane ([13]aneN4); 1,4,8,11-tetraazacyclotetradecane ([14]aneN4); 1,4,8,12-tetraazacyclopentadecane ([15]aneN4); 1,5,9,13-tetraazacyclohexadecane ([16]aneN4); ethylene-diamine-tetraacetic-acid (EDTA); and diethylene-triamine-penta-acetic acid (DTPA).

168. The method of the items 152-166, wherein said agent-entrapping component is a chelator selected from the group consisting of 1,4-ethano-1,4,8,11-tetraazacyclotetradecane (et-cyclam); 1,4,7,11-tetraazacyclotetradecane (isocyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl)diacetic acid (DO2A); 2,2', 2''-(1,4,7,10-tetraazacyclododecane-1,4,7-triyl) triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphonic acid) (DO2P); 1,4,7,10-tetraazacyclododecane-1,4,7-tri(methanephosphonic acid) (DO3P); 1,4,8,11-15 tetraazacyclotetradecane-1,4,8,11-tetraacetic acid (TETA); 2-(1,4,8,11-tetraazacyclotetradecane-1-yl)acetic acid (TE1A); 2,2'-(1,4,8,11-tetraazacyclotetradecane-1,8-diyl) diacetic acid (TE2A); ethylene-diamine-tetraacetic-acid (EDTA), and diethylene-triamine-penta-acetic acid (DTPA).

169. The method of item 168, wherein said agent-entrapping component is selected from the group consisting of 1,4,7,10-tetraazacyclododecane-1,4,7,10-tetraacetic acid (DOTA); 1,4,8,11-15 tetraazacyclotetradecane-1,4,8,11-tetraacetic acid (TETA); 1,4,7,10-tetraazacyclododecane-1,4,7,10-tetra(methanephosphonic acid) (DOTP), cyclam, and cyclen.

170. The method of item 169, wherein said agent-entrapping component is selected from the group consisting of 1,4,7,10-tetraazacyclododecane-1,4,7,10-tetraacetic acid (DOTA), 1,4,8,11-15 tetraazacyclotetradecane-1,4,8,11- tetraacetic acid (TETA), 1,4,7,10-tetraazacyclododecane-1,4,7,10-tetra(methanephosphonic acid) (DOTP), cyclam and cyclen.

171. The method of item 170, wherein said agent-entrapping component is 1,4,7,10-tetraazacyclododecane-1,4,7,10-tetraacetic acid (DOTA).

172. The method of any of the items 152-166, wherein said agent-entrapping component is a reducing agent.

173. The method of item 172, wherein said reducing agent is ascorbic acid, glucose, fructose, glyceraldehyde, lactose, arabinose, maltose and acetol.

174. The method of any of the items 152-166, wherein said agent-entrapping component is a compound which forms a low solubility salt with said radionuclides.

175. The method of item 174, wherein said compound forming a low solubility salt with said radionuclides is selected from the group consisting of phosphate, oxalate and chloride.

176. The method of any of the items 152-175, wherein said agent-entrapping component is a chelator (e.g. DOTA) and the reaction of transfer of radionuclide from carbostyril (2-hydroxyquinoline) to the chelating agent is spontaneous either inherently or as a result of a high concentration of chelating agent within the nanoparticle composition.

177. The method of any of the items 152-175, wherein said agent-entrapping component is a chelator (e.g. DOTA) and the reaction of transfer of radionuclide from the ionophore to the chelating agent is spontaneous as a result of a high concentration of chelating agent within the nanoparticle composition.

178. The method of any of the items 152-177, wherein said agent-entrapping component is a chelator and where the molar ratio of ionophore to chelator is in the range of 1:1 to 1:10000000, for example 1:5, such as 1:10, for example 1:50, such as 1:100, for example 1:250, such as 1:500, for example 1:1000, such as 1:5000, for example 1:10000, such as 1:50000, for example 1:100000, such as 1:500000, for example 1:1000000, such as 1:5000000, for example 1:10000000.

179. The method of any of the items 152-178, wherein the nanoparticle composition further comprises a targeting moiety.

180. The method of item 179, wherein the targeting moiety is attached to the surface of the nanoparticle composition via a lipid-anchoring molecule or PEG-conjugated lipid component.

181. The method of any of the items 179 or 180, wherein the targeting moiety attached to the surface of the nanoparticle composition is selected from the group consisting of antibodies, affibodies, or peptide components.

182. The method of item 181, wherein the targeting moiety is an antibody selected from the group consisting of Rituximab, Trastuzumab, Cetuximab, LymphoCide, Vitaxin, Lym-1 and Bevacizumab.

183. The method of item 181, wherein the targeting moiety is an affibody selected from the group consisting of anti-ErbB2 affibody, and anti-Fibrinogen affibody molecule.

184. The method of item 181, wherein the targeting moiety is a peptide component selected from the group consisting of RGD, somatostatin and analogs thereof, and cell-penetrating peptides.

185. The method of item 184, wherein said somatostatin analog is octreotate (TATE).

186. The method of any of the items 152-185, further comprising controlling the interior pH, thereby inducing effective encapsulation of the entrapped agent.

187. The method of any of the items 152-186, wherein the interior pH of the nanoparticle composition is within the range of 1 to 10, such as 1-2, for example 2-3, such as 3-4, for example 4-5, such as 5-6, for example 6-7, such as 7-8, for example 8-9, such as 9-10.

188. The method of any of the items 152-187, wherein the interior pH of the nanoparticle is within the range of the interior pH of the nanoparticle is within the range of 3 to 6, such as 3.0 to 3.5, for example 3.5 to 4.0, such as 4.0 to 4.5, for example 4.5 to 5.0, such as 5.0 to 5.5 for example 5.5 to 6.0

189. The method of any of the items 152-187, further comprising a compound with intracellular targeting properties entrapped within the nanoparticle composition.

190. The method of item 189, wherein the compound with intracellular targeting properties is a nuclear localization sequence peptide (NLS peptide) which is conjugated to the agent-entrapping component.

191. The method of any of the items 152-190, wherein the diameter of the nanoparticle composition is between 30 nm and 300 nm; such as 30 nm to 60 nm, for example 60 nm to 80 nm, such as 80 nm to 100 nm, for example 100 nm to 120 nm, such as 120 nm to 150 nm, for example 150 nm to 180 nm, such as 180 nm to 210 nm, for example, 210 nm to 240 nm, such as 240 nm to 270 nm for example 270 nm to 300 nm.

192. The method of any of the items 152-191, wherein the diameter of the nanoparticle is less than 120 nm.

193. The method of any of the items 152-191, wherein the diameter of the nanoparticle is larger than 80 nm.

194. The method of any of the items 152-193, wherein the purity of the generated radiolabeled nanoparticles is verified using size exclusion chromatography (SEC), ion-exchange chromatography or dialysis.

195. The method of any of the items 54-194, wherein the generated radio-labeled nanoparticles are purified using size exclusion chromatography (SEC), ion-exchange chromatography or dialysis.

196. The method of any of the items 152-195, wherein entrapment of radionuclide is in the range of 30% to 95% as assayed using size exclusion chromatography (SEC), ion-exchange chromatography or dialysis.

197. The method of any of the items 152-196, wherein entrapment of radionuclide is greater than 35% as assayed using size exclusion chromatography (SEC), ion-exchange chromatography or dialysis, such as greater than 40%, for example greater than 50%, such as greater than 60%, for example greater than 70%, such as greater than 80% for example greater than 85%, such as greater than 90%, for example greater than 95%.

198. The method of any of the items 152-197, wherein the stability of the radiolabeled nanoparticles is such that less than 20% leakage of radioactivity is observed following 24 hours incubation in human serum at 37° C. followed by a purification step such as size exclusion chromatography (SEC), ion-exchange chromatography or dialysis to separate the radiolabeled nanoparticles from leaked radionuclide, for example less than 15% leakage, such as less than 12% leakage, for example less than 10% leakage, such as less than 8% leakage, for example less than 6% leakage, such as less than 4% leakage, for example less than 3% leakage, such as less than 2% leakage, for example less than 1% leakage.

199. The method of any of the items 152-198, wherein the size of the nanoparticle remains essentially unaltered following loading of the nanoparticles with radionuclide.

200. The method of any of the items 152-198, wherein the size of the nanoparticle compositions is altered less than 20% following loading of the nanoparticles with radionuclide, for example less than 17%, such as less than 14%, for example less than 11%, such as less than 8%, for example less than 5%, such as less than 2%.

201. The method of any of the items 152-200, wherein the zeta potential is altered less than 20% following loading of the nanoparticles with radionuclide, such as 18%, for example less than 16%, such as less than 14%, for example less than 12%, such as less than 10%.

202. The method of any of the items 152-201, further comprising measuring and detecting the amount of radiation emitted from the radionuclide within the nanoparticle composition.

203. The method of any of the items 152-202, further comprising use of the nanoparticle composition for diagnosis or treatment.

204. The method of item 203, wherein the nanoparticle composition is administered orally.

205. The method of item 203, wherein the nanoparticle composition is administered intravenously.

206. The method of any of the items 203-205, wherein said method is used in diagnosing pathological conditions associated with leaky blood vessels.

207. The method of any of the items 203-205, wherein said method is used in diagnosing cancer.

208. A kit of parts for preparing a nanoparticle composition as described in any of the items 152-202, said kit comprising
   a. a nanoparticle composition comprising
      i. a vesicle forming component, and
      ii. an agent-entrapping component enclosed by the vesicle forming component; and
   b. a composition containing an ionophore as described in any of the items 61-74 (formula A),
wherein part a or part b further comprises a radionuclide.

209. A kit of parts for preparing a nanoparticle composition as described in any of the items 152-202, said kit comprising
   a. a nanoparticle composition comprising
      i. a vesicle forming component, and
      ii. an agent-entrapping component enclosed by the vesicle forming component; and
   b. a composition containing an ionophore as described in any of the items 61-74 (formula A),
   c. a composition containing a radionuclide.

210. A kit of parts for preparing a nanoparticle composition as described in any of the items 152-202, said kit comprising
   a. a nanoparticle composition comprising
      i. a vesicle forming component, and
      ii. an agent-entrapping component enclosed by the vesicle forming component; and
      iii. an ionophore as described in any of the items 61-74 (formula A),
   b. a composition containing a radionuclide.

211. The kit of parts of any of the items 208-210, wherein said radionuclide is selected from the group consisting of Copper (61 Cu, 64Cu, and 67Cu), Indium (111In), Technetium (99 mTc), Rhenium (188Re), Gallium (67Ga, 68Ga), Lutetium (177Lu), Actinium (225Ac), Yttrium (90Y), Antimony (119Sb), Tin (117Sn, 113Sn), Dysprosium (159Dy), Cobalt (56Co), Iron (59Fe), Ruthenium (97Ru, 103Ru), Palladium (103Pd), Cadmium (115Cd), Tellurium (118Te, 123Te), Barium (131 Ba, 140Ba), Gadolinium (149Gd, 151 Gd), Terbium (160Tb), Gold (198Au, 199Au), Lanthanum (140La), and Radium (223Ra, 224Ra).

212. The kit of parts of any of the items 208-210, wherein said radionuclide is selected from the group consisting of Copper (61 Cu, 64Cu, and 67Cu), Indium (111In), Technetium (99 mTc), Rhenium (188Re), Gallium (67Ga, 68Ga), Actinium (225Ac), Yttrium (90Y), Antimony (119Sb), and Lutetium (177Lu).

213. The kit of parts of any of the items 208-211, wherein said radionuclide is in the form of ions such as monovalent cations, for example divalent cations, such as trivalent cations, for example tetravalent cations, such as pentavalent cations, for example hexavalent cations such as heptavalent cations.

214. The kit of parts of any of the items 208-213, wherein said agent-entrapping component is a chelator (e.g. DOTA) and the reaction of transfer of radionuclide from the ionophore to the chelating agent is spontaneous, either inherently or as a result of a high concentration of chelating agent within the nanoparticle composition.

215. The kit of parts of any of the items 208-213, wherein said agent-entrapping component is a chelator (e.g. DOTA) and the reaction of transfer of radionuclide from the ionophore to the chelating agent is spontaneous as a result of a high concentration of chelating agent within the nanoparticle composition.

216. The kit of parts of any of the items 208-215, wherein said agent-entrapping component is a chelator and where the molar ratio of ionophore to chelator is in the range of 1:1 to 1:10000000, for example 1:5, such as 1:10, for example 1:50, such as 1:100, for example 1:250, such as 1:500, for example 1:1000, such as 1:5000, for example 1:10000, such as 1:50000, for example 1:100000, such as 1:500000, for example 1:1000000, such as 1:5000000, for example 1:10000000.

217. The kit of parts of any of the items 208-216, wherein the radionuclide is delivered in the form of a salt.

218. The kit of parts of any of the items 208-217, wherein the radionuclide is delivered in the form of a lyophilized salt.

219. The kit of parts of any of the items 208-216, wherein the radionuclide is delivered as an aqueous solution of ions.

220. The kit of parts of any of the items 208-219, further comprising a test for determining efficiency of encapsulation.

221. The kit of parts of any of the items 208-220, wherein said parts can be mixed 0-5 hours before use; such as 0-4 hours before use, for example 0-3 hours before use, such as 0-2 hours before use, for example 0-1 hour before use, such as immediately before use.

222. The kit of parts according to any of the items 208-221, for preparing a nanoparticle composition of any of the items 1-53.

223. The kit of parts of any of the items 208-222, for use in diagnosing pathological conditions associated with leaky blood vessels.

224. The kit of parts of any of the items 208-222, for use as a medicament.

225. The kit of parts of any of the items 208-222, for use in diagnosing cancer.

226. The kit of parts of any of the items 208-222, for use in positron emission tomography (PET) scanning or single photon emission computed tomography (SPECT) scanning.

EXAMPLES I

The following examples illustrate a novel method for preparation of a liposome composition with entrapped radionuclides useful in delivering a radio-diagnostic and/or radiotherapeutic agent via the blood circulation to the target site, for example, a cancer tissue, or another pathological condition associated with leaky blood vessels, where the specificity and intensity of radioactivity signal localized in the target site are enhanced. The examples are in no way intended to limit the scope of the present invention. The radionuclide, $^{64}$Cu, is used as a model nuclide representing the chemical properties of all copper isotopes.

Isothermal titration calorimetry (ITC) measurements are designed to obtain primarily the enthalpy of each complex formation and their stoichiometries. The heats of each reaction are determined by integration of the peaks observed. After the contribution from the heat of dilution of each injection is subtracted, the heat is plotted against the molar ratio of the measured components. The binding constant ($K_a$, interchangeably referred to as the ligand exchange constant, K), enthalpy of binding) ($\Delta H^\circ$), and stoichiometry (n) of the formation of complex are determined by fitting the binding isotherm against the binding equation using an independent binding model.

ITC sample preparation and experiments: Solutions of $CuCl_2$, 2-hydroxyquinoline (carbostyril, 2HQ), (Sigma-Aldrich Co., Denmark) and DOTA for ITC experiments were made up in Milli-Q water (pH 7.4). The ITC measurements of the binding affinity of the metal ion, ionophore and chelator were carried out at 25° C. using isothermal titration calorimetry (Nano ITC, TA). The instrument was electrically calibrated by means of a standard electric pulse as recommended by the manufacturer. A 250 μL syringe was used for the titrant, mixing was effected by stirring the syringe at 400 rpm during equilibration and experiment. Typically 20 injections of 10 μL each were performed with a 600 s interval between injections in a single titration. The reference cell of the calorimeter filled with water, acts as a thermal reference to the sample cell. To correct for $CuCl_2$, DOTA and carbostyril heats of dilution, control experiments were also performed using similar conditions with buffer solution only. All solutions were degassed before titrations to reduce the noise.

ITC measurement of the extraction of Cu(II) from 2-hydroxyquinoline by DOTA performed within the present invention is shown in FIG. 6. The exchange of 2-hydroxyquinoline with DOTA are shown as heat spike plots (A) and integrated heat plots (B). Experimental conditions: 0.5 mM Cu(2-hydroxyquinoine)$_2$ is titrated with 10-μL injections of 5 mM DOTA. All solutions were prepared in Milli-Q water at pH=7.4.

Based on the ITC data (FIG. 6), DOTA is found to have a much higher binding affinity to Cu(II) than 2-hydroxyquinoline. 2-hydroxyquinoline-aided loading of Cu(II) into liposomes containing DOTA, is thus a thermodynamic favorable process.

Radiolabeling of $^{64}$Cu-carbostyril:

An example of the preparation of the $^{64}$Cu-carbostyril included in the method of preparing the liposome composition of the present invention follows. A total of 5-100 μL of 0.314 to 31.4 mM 2-hydroxyquinoline (carbostyril, 2HQ), (Sigma-Aldrich Co., Denmark) in an aqueous buffer, for example, a HEPES buffer (10 mM, 150 mM NaCl, pH 7.4) was added to dried radioactive $^{64}$CuCl$_2$.

Radiolabeling of $^{64}$Cu-oxine:

An example of the preparation of the $^{64}$Cu-oxine included in the method of preparing the liposome composition of the present invention follows. A total of 5-100 μL of 0.314 to 31.4 mM 8-hydroxyquinoline (oxine, 8HQ), (Sigma-Aldrich Co., Denmark) in an aqueous buffer, for example, a HEPES buffer (10 mM, 150 mM NaCl, pH 7.4) was added to dried radioactive $^{64}$CuCl$_2$.

Preparation of Liposomes:

Small unilamellar vesicles (SUV) (size 100 nm) were prepared using the standard thin-film hydration and repeated extrusions. 1,2-distearoyl-sn-glycero-3-phosphocholine (DSPC), cholesterol and 1,2-distearoyl-sn-glycero-3-phosphoethanolamine-N-[methoxy (polyethylene glycol)-2000 gl] (DSPE-PEG-2000) in the molar ratio 55:40:5 were dissolved and mixed in chloroform to a lipid-film under a gentle stream of argon. Organic solvent residues were removed under reduced pressure overnight. The lipid-film was dispersed by adding a suitable aqueous solution, for example, a HEPES buffer (10 mM, 150 mM NaCl, pH 7.4) and hydrated for 60 min at 65° C. The suspension was then extruded through polycarbonate membrane filters using a mini-extruder to obtain SUVs.

Preparation of Chelator-Containing Liposomes:

Chelating agent (for example DOTA) was trapped within the liposomes consisting of DSPC, cholesterol and DSPE-PEG-2000 in the molar ratio 55:40:5 using the standard thin-film hydration and repeated extrusions. Briefly, the lipids were mixed in chloroform and dried to a lipid-film under a gentle stream of nitrogen. Organic solvent residues were removed under reduced pressure overnight. The lipid-film was dispersed by adding an aqueous solution, for example, a HEPES buffer (10 mM, 150 mM NaCl, pH 7.4) containing the chelating-agent (DOTA) in the concentration range of 1-50 mM. The solution was then hydrated at 65° C. for 60 min. The multi lamellar vesicles (MLVs) were sized to small unilamellar vesicles (SUVs) by multiple extrusions through 100 nm polycarbonate filters using a mini-extruder. Unentrapped chelating-agent was removed by size exclusion chromatography (SEC) on a Sephadex G-50 packed 1×25 cm column eluted with an aqueous solution, for example, a HEPES buffer (10 mM, 150 mM NaCl, pH 7.4).

Liposome Loading with Radiolabeled $^{64}$Cu-carbostyril:

Liposomes were loaded by incubation of 0.1-1 GBq of 5-100 μL radiolabeled $^{64}$Cu-carbostyril with 0.5-2 mL chelate-containing liposomes at 37-50° C. for 60 min. The loaded $^{64}$Cu-liposomes were assayed by separating the unentrapped radionuclide, $^{64}$Cu, from $^{64}$Cu-liposomes by size exclusion chromatography (SEC) on a Sephadex G-50 column. The elution profile was monitored on an in line radioactivity detector. $^{64}$Cu entrapment was greater than 90%. FIG. 7A illustrates that carbostyril can load $^{64}$Cu into the interior of DOTA encapsulated liposomes. FIG. 7A further illustrates the encapsulation degree results of $^{64}$Cu when using carbostyril as ionophore.

Figure 7B:
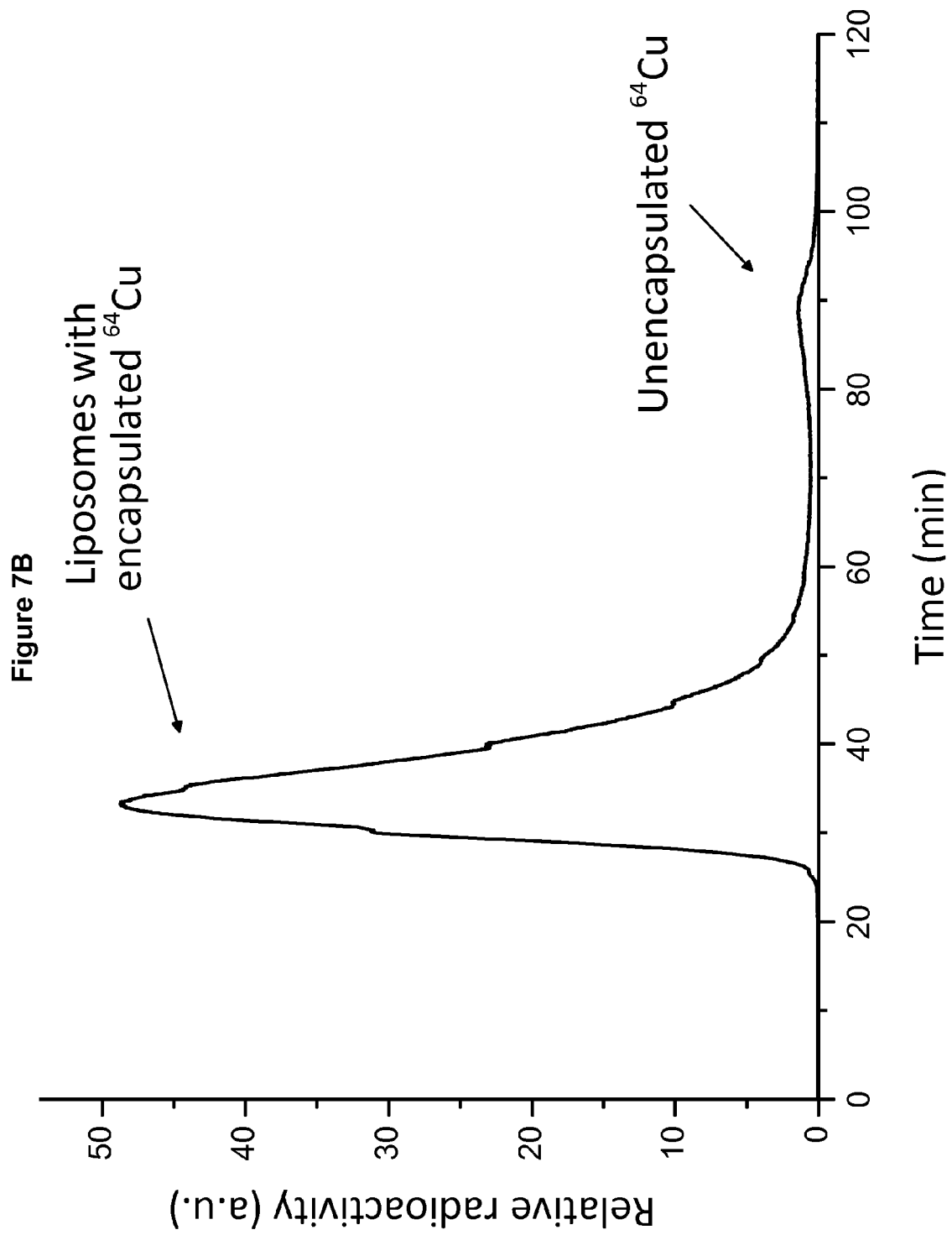

Liposome Loading with Radiolabeled $^{64}$Cu-oxine:

Liposomes was loaded by incubation of 0.1-1 GBq of 5-100 μL radiolabeled $^{64}$Cu-oxine with 0.5-2 mL chelate-containing liposomes at 37-50° C. for 60 min. The loaded $^{64}$Cu-liposomes were assayed by separating the unentrapped radionuclide, $^{64}$Cu, from $^{64}$Cu-liposomes by size exclusion chromatography (SEC) on a Sephadex G-50 column. The elution profile was monitored on an in line radioactivity detector. $^{64}$Cu entrapment was greater than 90%. FIG. 7B illustrates that oxine can load $^{64}$Cu into the interior of DOTA encapsulated liposomes. FIG. 7B further illustrates the encapsulation degree results of $^{64}$Cu when using oxine as ionophore.

Storage Stability at 37° C. for 24 h of $^{64}$Cu-Liposome Loaded with $^{64}$Cu Using Carbostyril:

A purified 500 uL $^{64}$Cu-Liposome solution was incubated at 37° C. for 24 h, and the stability of the $^{64}$Cu-Liposome were assayed by separating free $^{64}$Cu from $^{64}$Cu-Liposome by size exclusion chromatography (SEC) on a Sephadex G-50 column. The elution profile was monitored on an in line radioactivity detector. FIG. 8A illustrates results from the storage stability test where $^{64}$Cu-liposomes containing 10 mM DOTA retained more than 99% of the total radioactivity when the $^{64}$Cu was loaded by carbostyril. The radionuclide then binds preferably to DOTA encapsulated in the interior of the liposome, due to its stronger affinity thereto, allowing the release of free carbostyril, and the entrapment of the radionuclide.

Storage Stability at 37° C. for 24 h of $^{64}$Cu-Liposome Loaded with $^{64}$Cu Using Oxine:

A purified 500 uL $^{64}$Cu-Liposome solution was incubated at 37° C. for 24 h, and the stability of the $^{64}$Cu-Liposome were assayed by separating free $^{64}$Cu from $^{64}$Cu-Liposome by size exclusion chromatography (SEC) on a Sephadex G-50 column. The elution profile was monitored on an in line radioactivity detector. FIG. 8B illustrates results from the storage stability test where $^{64}$Cu-liposomes containing 10 mM DOTA only retained 79% (a leakage of 21% of the encapsulated $^{64}$Cu) of the total radioactivity encapsulated when the $^{64}$Cu was loaded by oxine.

Serum Stability of $^{64}$Cu-Liposomes Loaded with $^{64}$Cu Using Carbostyril:

A purified 250 uL $^{64}$Cu-Liposome solution was incubated at 37° C. for 24 h in 250 uL human serum, and the stability of the $^{64}$Cu-Liposome were assayed by separating free $^{64}$Cu from $^{64}$Cu-Liposome by size exclusion chromatography (SEC) on a Sephadex G-50 column. Results from the serum stability test where $^{64}$Cu-liposomes containing 10 mM DOTA showed that more than 99% of the total radioactivity remained in the liposomes when the $^{64}$Cu was loaded by carbostyril.

Additionally, the size and zeta potential of $^{64}$Cu-liposomes before and after loading of $^{64}$Cu using the ionophore, carbostyril, were measured. As shown in Table 1 immediately below, no significant differences in size before (97.9 nm) or after (96.07 nm) $^{64}$Cu-loading were observed, or in zeta potential before (−4.09 mV) or after (−3.78 mV) the $^{64}$Cu-loading, demonstrating high in vitro stability of the $^{64}$Cu-liposomes composition prepared in the present invention.

TABLE 1

Size (nm) and zeta potential (mV) of $^{64}$Cu-Liposome compositions loaded with $^{64}$Cu using carbostyril before and after (one week) $^{64}$Cu loading.

| Lipsosome composition | Size (nm) | | zeta potential (mV) | |
|---|---|---|---|---|
| | before loading | after loading | before loading | after loading |
| (DSPC/CHOL/ DSPE-PEG) in molar ratio 55:40:5 | 97.9 ± 0.5 (n = 3) | 96.07 ± 0.77 (n = 9) | −4.09 ± 0.54 (n = 10) | −3.78 ± 0.92 (n = 50) |

Due to the high storage and serum stability only $^{64}$Cu-liposomes loaded with $^{64}$Cu using the ionophore, carbostyril, were used for in vivo studies.

The results described above demonstrates that the present invention provides a radionuclide encapsulated in a liposome consisting of a liposome composition having vesicle forming components, an agent-entrapping component enclosed by the vesicle forming component, and a radiolabeled agent entrapped within the liposome composition, wherein the radiolabeled agent comprises a copper isotope.

Furthermore the results described above demonstrate that the present invention provides a new method for loading liposome compositions with copper isotopes or other radionuclides by using a new ionophore, the chemical compound, carbostyril (2-hydroxyquinoline, 2HQ) or other derivates thereof as outlined in FIG. 1 or preferably FIG. 2.

The results described above also demonstrate that liposome compositions according to embodiments of the present invention can be used successfully for in vivo studies. Additionally, the results demonstrated liposome compositions preparation included a desired entity, for example a copper isotope selected from the group consisting of, but not limited to, $^{61}$Cu, $^{64}$Cu and $^{67}$Cu, with high loading efficiency (>90%) in a stable form with minimal release (i.e. leakage) of the encapsulated entity upon storage and in human serum incubation for 24 h at 37° C. The liposome compositions prepared within this invention can thus be used in nuclear imaging, including PET imaging, for in vivo cancer diagnostic applications and for diagnosing other pathological conditions associated with leaky blood vessels in a subject. These novel radiolabeled liposome compositions are also useful in radiotherapeutic applications treating a cancer disease or another disease within a subject.

EXAMPLES II

The following additional examples further illustrate embodiments of the invention. The examples are in no way intended to limit the scope of the present invention and the radionuclide, $^{64}$Cu, remains the model nuclide representing the chemical properties of all copper isotopes.

Isothermal titration calorimetry (ITC) measurements were used to obtain the equilibrium constant (K, also referred to as the exchange constant) of the ligand exchange between the ionophore and the agent-entrapping compound, here a chelator. The ligand exchange of carbostyril (2-hydroxyquinoline, 2HQ) with DOTA when complexed to Cu(II) was investigated by titrating a buffered solution of Cu(2HQ)$_2$ with DOTA. The ligand exchange was monitored by the heat of reaction from each injection in the ITC experiment (FIG. 9A) as determined by peak integration. The ligand exchange constant (K) was determined by fitting the heat of reaction shown in FIG. 9B. The binding isotherm is defined by the equilibrium:

Cu(2HQ)$_2$+DOTA $\Leftrightarrow$ CuDOTA+2(2HQ)

The ligand exchange constant, K, is defined as:

$$K = \frac{\text{Cu}DOTA \cdot (2HQ)^2}{\text{Cu}(2HQ)_2 \cdot DOTA \cdot c_w}$$

wherein CuDOTA, Cu(2HQ)$_2$, 2HQ and DOTA are the concentrations of the Cu-DOTA complex and Cu(2HQ)$_2$ complex, and the free concentration of 2HQ and DOTA respectively. $c_w$ is the molarity of pure water (55.5 M).

ITC Sample Preparation and Experiments:

Solutions of CuCl$_2$, 2HQ and DOTA for ITC experiments were made in MES buffer (pH 5.9) and in acetate buffer (pH 4.0). The ITC measurements were carried out at 25° C. using isothermal titration calorimetry (iTC200, MicroCal, GE). The instrument was electrically calibrated by means of a standard electric pulse as recommended by the manufacturer. A 40 μL syringe was used for the titration, mixing was effected by stirring the syringe at 1000 rpm during equilibration and experiments. Typically, 20 injections of 2 μL each were performed with a 150 s interval between injections in a single titration. The reference cell of the calorimeter filled with water acts as a thermal reference to the sample cell. To correct for CuCl$_2$, 2-HQ and DOTA, heats of dilution control experiments were performed using similar conditions with buffer solution only. All solutions were degassed before titrations to reduce noise.

ITC measurement of the extraction of Cu(II) from 2HQ by DOTA in MES buffer (pH 5.9) performed within the present invention is shown in FIG. 9. The exchange of 2HQ with DOTA at pH 5.9 is shown as heat spike plots (A) and integrated heat plots (B). Experimental conditions: 0.05 mM Cu(2HQ)$_2$ was titrated with 2-µL injections of 0.5mM DOTA. All solutions were prepared in MES buffer at pH=5.9.

Based on the ITC data (FIG. 9), the exchange constant, K, is estimated to $(5.2\pm1.6)\cdot10^{-4}$ at pH 5.9 in MES buffer and to $(1.0\pm0.3)\cdot10^{-2}$ in acetate buffer at pH 4.0, showing that the exchange of Cu(II) from 2HQ to DOTA is more favourable at pH 4.0 than at pH 5.9. The liposomes for loading $^{64}$Cu were prepared with a high DOTA concentration inside the liposomes giving a ratio of CuDOTA/Cu(2HQ)$_2$≈$10^5$ during the loading. The high CuDOTA to Cu(2HQ)$_2$ concentration ratio inside the liposome is favorable for achieving high loading efficiency and encapsulation stability. The 2HQ mediated transport of $^{64}$Cu through the lipid bilayer membrane involves a rapid exchange of Cu(II) from 2HQ to DOTA, and 2HQ can aid loading of $^{64}$Cu into liposomes containing DOTA.

Radiolabeling of $^{64}$Cu-2HQ:

An example of the preparation of the $^{64}$Cu-2HQ included in the method of preparing the liposome compositions of the present invention follows. A total of 10 µL of 0.314 mM 2HQ in HEPES buffer (10 mM, 150 mM NaCl, pH 7.4) was added to dried radioactive $^{64}$CuCl$_2$. The radiolabeling of $^{64}$Cu-2HQ was also successful with higher 2HQ concentrations and in other buffers such as MES and acetate buffer.

Radiolabeling of $^{64}$Cu-oxine:

An example of the preparation of the $^{64}$Cu-oxine included in the method of preparing the liposome compositions of the present invention follows. A total of 10 µL of 0.314 mM oxine in a HEPES buffer (10 mM, 150 mM NaCl, pH 7.4) was added to dried radioactive $^{64}$CuCl$_2$. The radiolabeling of $^{64}$Cu-oxine was also successful with higher oxine concentrations and in other buffers such as MES and acetate buffer.

Preparation of Liposomes:

Small unilamellar vesicles (SUV) (size 100 nm) were prepared using the standard thin-film hydration and repeated extrusions. 1,2-distearoyl-sn-glycero-3-phosphocholine (DSPC), cholesterol and 1,2-distearoyl-sn-glycero-3-phosphoethanolamine-N-[methoxy (polyethylene glycol)-2000] (DSPE-PEG-2000) in the molar ratio 55:40:5 were dissolved and mixed in chloroform to a lipid-film under a gentle stream of argon. Organic solvent residues were removed under reduced pressure overnight. The lipid-film was dispersed by adding a suitable aqueous solution, for example, a HEPES buffer (10 mM, 150 mM NaCl, pH 7.4) and hydrated for 60 min at 65° C. The suspension was then extruded through polycarbonate membrane filters using a mini-extruder to obtain SUVs.

Preparation of Chelator-containing Liposomes:

Chelating agent (for example DOTA) was trapped within the liposomes consisting of DSPC, cholesterol and DSPE-PEG-2000 in the molar ratio 55:40:5 using the standard thin-film hydration and repeated extrusions. Briefly, the lipids were mixed in chloroform and dried to a lipid-film under a gentle stream of nitrogen. Organic solvent residues were removed under reduced pressure overnight. The lipid-film was dispersed by adding an aqueous solution, for example, a HEPES buffer (10 mM, 150 mM NaCl, pH 7.4) containing chelating agent (DOTA) in a concentration of 10 mM, and at a pH of 4.0. The solution was hydrated at 65° C. for 60 min.

The multi lamellar vesicles (MLVs) were downsized to small unilamellar vesicles (SUVs) by multiple extrusions through 100 nm polycarbonate filters using a mini-extruder. Un-entrapped chelating agent was removed by size exclusion chromatography (SEC) on a Sephadex G-50 packed 1×25 cm column eluted with HEPES buffer (10 mM, 150 mM NaCl, pH 7.4).

Figure 10A:
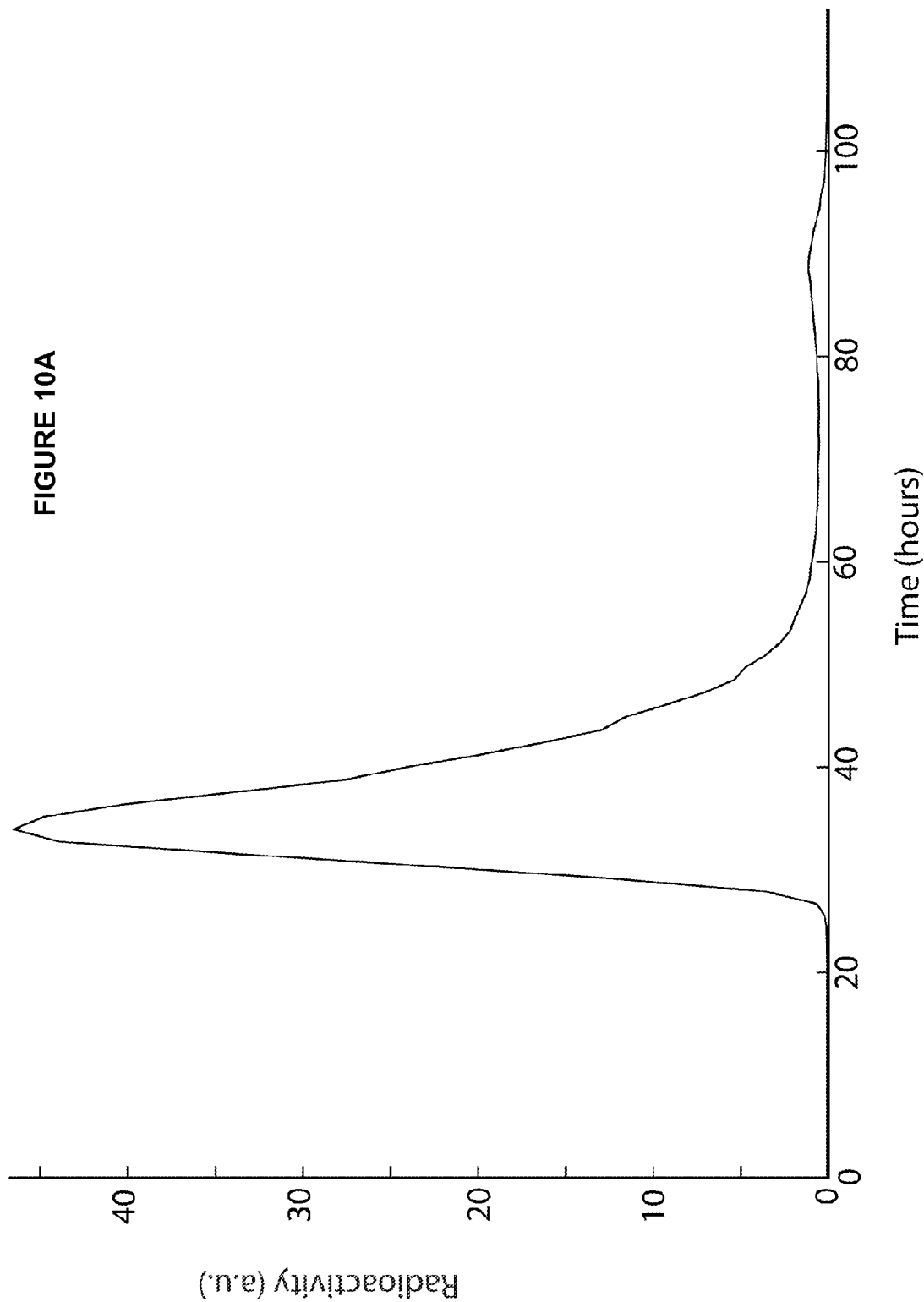

Liposome Loading with Radiolabeled $^{64}$Cu-2HQ:

Liposomes produced as described in above were loaded by incubating 100 MBq of 10 µL radiolabeled $^{64}$Cu-2HQ with 0.5 mL chelate-containing liposomes at 50° C. for 60 min. The loading was also possible with higher radioactivity (100-400 MBq), with different liposome concentrations (1-50 mM) and liposome volumes (0.5-2 mL). The loading was successfully employed at temperatures down to 20° C. and with an incubation time down to 30 min. The $^{64}$Cu loaded liposomes were assayed by separating the unentrapped radionuclide, $^{64}$Cu, from $^{64}$Cu-liposomes by size exclusion chromatography (SEC) on a Sephadex G-50 column. The elution profile was monitored on an in line radioactivity detector. $^{64}$Cu entrapment was greater than 90%. FIG. 10A illustrates that 2HQ efficiently loads $^{64}$Cu into the interior of liposomes encapsulated with DOTA. FIG. 10A further illustrates the high encapsulation efficiency when using carbostyril as ionophore.

Liposome Loading with Radiolabeled $^{64}$Cu-oxine:

Liposomes produced as described in above was loaded by incubating 100 MBq of 10 µL radiolabeled $^{64}$Cu-oxine with 0.5 mL chelate-containing liposomes at 50° C. for 60 min. The loading was also possible with higher radioactivity (100-400 MBq), with different liposome concentrations (1-50 mM) and liposome volumes (0.5-2 mL). The loaded $^{64}$Cu-liposomes were assayed by separating the unentrapped radionuclide, $^{64}$Cu, from $^{64}$Cu-liposomes by size exclusion chromatography (SEC) on a Sephadex G-50 column. The elution profile was monitored on an in line radioactivity detector. $^{64}$Cu entrapment was greater than 90%. FIG. 10B illustrates that oxine efficiently loads $^{64}$Cu into the interior of liposomes encapsulated with DOTA. FIG. 10B further illustrates the encapsulation efficiency when using oxine as ionophore.

Storage Stability at 37° C. for 24 h of $^{64}$Cu-Liposome Loaded with $^{64}$Cu Using 2HQ:

A purified 500 uL $^{64}$Cu-liposome solution loaded with 2HQ was incubated at 37° C. for 24 h, and the stability of the $^{64}$Cu-liposomes was assayed by separating unencapsulated $^{64}$Cu from $^{64}$Cu-liposome by size exclusion chromatography (SEC) on a Sephadex G-50 column. The elution profile was monitored on an in line radioactivity detector. FIG. 8A illustrates the results from the storage stability test where $^{64}$Cu-liposomes containing 10 mM DOTA at pH 4.0 retained more than 99% of the total radioactivity when the $^{64}$Cu was loaded by carbostyril. In the liposome, the radionuclide binds preferably to DOTA encapsulated in the interior of said liposome, allowing the release of free carbostyril, and the entrapment of the radionuclide. FIG. 8C shows the results from the stability test after 24 h, where $^{64}$Cu-liposomes were loaded using 2HQ containing 10 mM DOTA at pH 7.4. After 24 h, 51% leakage of the encapsulated $^{64}$Cu was observed.

Figure 8D:
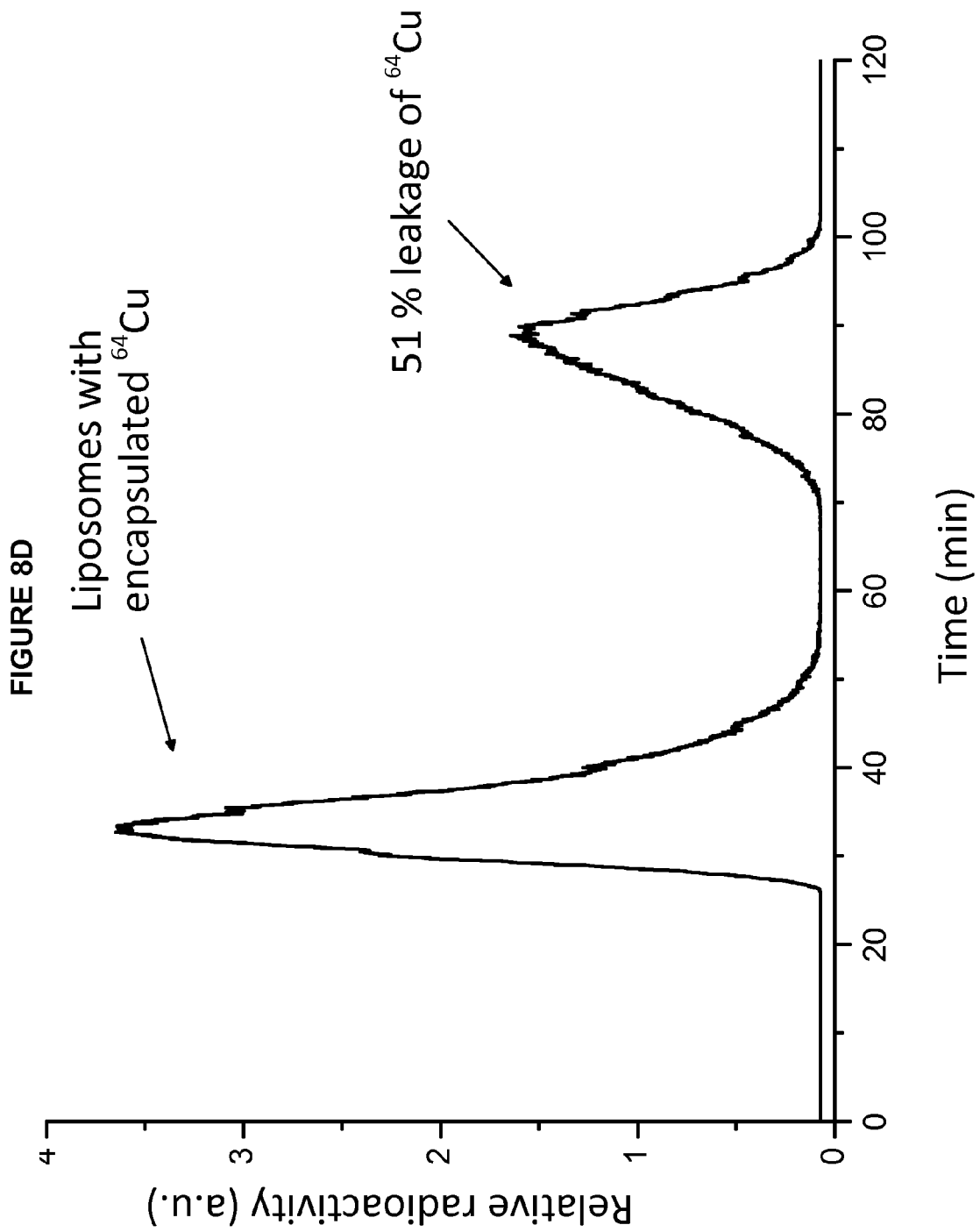

Storage stability at 37° C. for 24 h of $^{64}$Cu-liposome loaded with $^{64}$Cu using oxine: A purified 500 uL $^{64}$Cu-liposome solution loaded with oxine was incubated at 37° C. for 24 h, and the stability of the $^{64}$Cu-liposomes was assayed by separating unencapsulated $^{64}$Cu from $^{64}$Cu-liposomes by size exclusion chromatography (SEC) on a Sephadex G-50 column. The elution profile was monitored on an in line radioactivity detector. FIG. 8B shows the results from the storage stability test where $^{64}$Cu-liposomes loaded using oxine containing 10 mM DOTA at pH 4.0 only remained 79% (a leakage of 21% of the encapsulated $^{64}$Cu) of the total radioactivity encapsulated when the $^{64}$Cu was loaded by oxine. FIG. 8D shows the results from the storage stability test where $^{64}$Cu-liposomes were loaded using oxine, containing 10 mM DOTA at pH 7.4. After 24 h, 51% leakage of the encapsulated $^{64}$Cu was observed.

Serum Stability of $^{64}$Cu-liposomes Loaded with $^{64}$Cu Using 2HQ:

A purified 250 uL $^{64}$Cu-Liposome solution was incubated at 37° C. for 24 h in 250 uL human serum, and the stability of the $^{64}$Cu-Liposome were assayed by separating free $^{64}$Cu from $^{64}$Cu-liposomes by size exclusion chromatography (SEC) on a Sephadex G-50 column. Results from the serum stability test using $^{64}$Cu-liposomes containing 10 mM DOTA at pH 4.0, showed that more than 99% of the total $^{64}$Cu remained in the liposomes after 24 h when using 2HQ for loading.

The results described above demonstrate that the present invention provides a radionuclide encapsulated in a liposome—preferably in the form of a nanoparticle—consisting of a liposome composition having vesicle-forming components, an agent-entrapping component enclosed by the vesicle-forming component, and a radio-labeled agent entrapped within the liposome composition, wherein the radiolabeled agent comprises a copper isotope.

Furthermore, the results described above demonstrate that the present invention provides a new method for loading liposome compositions with copper isotopes or other radionuclides utilizing a novel ionophore, the chemical compound carbostyril or derivatives thereof, or oxine or derivatives thereof, as outlined in FIG. 1 or FIG. 3 or preferably FIG. 2 and FIG. 4.

The results described above also demonstrate liposome compositions according to embodiments of the present invention that can be used successfully for in vivo studies. Additionally, the results demonstrate preparation of liposome compositions which include a desired entity, for example a copper isotope selected from the group consisting of, but not limited to, $^{61}$Cu, $^{64}$Cu and $^{67}$Cu, with high loading efficiency (>90%) in a stable form with minimal release (i.e. leakage) of the encapsulated entity upon storage and in human serum incubation for 24 h at 37° C. In a preferred embodiment the copper isotope is selected from the group consisting of $^{61}$Cu, $^{64}$Cu, and $^{67}$Cu. In one embodiment as described herein above, when the ionophore is carbostyril or a derivative thereof, the radionuclide may include radionuclides different from copper. The liposome compositions prepared within this invention can thus be used in nuclear imaging, including PET imaging, for in vivo cancer diagnostic applications and for diagnosing other pathological conditions associated with leaky blood vessels in a subject. These novel radiolabeled liposome compositions are also useful in radio-therapeutic applications treating a cancer disease or another disease within a subject.

EXAMPLES III

The following additional examples further illustrate embodiments of the invention. The examples are in no way intended to limit the scope of the present invention and the radionuclide, $^{64}$Cu, remains the model nuclide representing the chemical properties of all copper isotopes including $^{61}$Cu and $^{67}$Cu for diagnostic and therapeutic applications.

Isothermal titration calorimetry (ITC) measurements were used to obtain the equilibrium constant (K, also referred to as the exchange constant) of the ligand exchange between the ionophore and the agent-entrapping compound, here a chelator. The ligand exchange of carbostyril (2-hydroxyquinoline, 2HQ) with a chelate when complexed to Cu(II) was investigated by titrating a buffered solution of Cu(2HQ)$_2$ with one of the following chelates: DOTA, TETA, cyclam, cyclen and DOTP. The ligand exchange was monitored by the heat of reaction from each injection in the ITC experiment as determined by peak integration. The ligand exchange constant (K) was determined by fitting the heat of reaction. The binding isotherm is defined by the equilibrium:

$$Cu(2HQ)_2 + chelate \Leftrightarrow Cu(chelate) + 2(2HQ) \quad (1)$$

The ligand exchange constant, K, is defined as:

$$K = \frac{Cu(chelate) \cdot (2HQ)^2}{Cu(2HQ)^2 \cdot chelate \cdot c_w}$$

wherein Cu(chelate), Cu(2HQ)$_2$, 2HQ and chelate are the concentrations of the Cu(chelate) complex and Cu(2HQ)$_2$ complex, and the free concentration of 2HQ and chelate respectively. $c_w$ is the molarity of pure water (55.5 M).

ITC sample preparation and experiments: Solutions of CuCl$_2$, 2HQ and the different chelates (DOTA, TETA, cyclam, cyclen and DOTP) for ITC experiments were made in MES buffer (pH 5.9) and in acetate buffer (pH 4.0). The ITC measurements were carried out at 25° C. and 50° C. using isothermal titration calorimetry (iTC200, Micro-Cal, GE). The instrument was electrically calibrated by means of a standard electric pulse as recommended by the manufacturer. A 40 µL syringe was used for the titration, mixing was effected by stirring the syringe at 1000 rpm during equilibration and experiments. Typically, 20 injections of 2 µL each were performed with a 150 s interval between injections in a single titration. The reference cell of the calorimeter filled with water acts as a thermal reference to the sample cell. To correct for CuCl$_2$, 2HQ and chelate heats of dilution, control experiments were performed using similar conditions with buffer solution only. All solutions were degassed before titrations to reduce noise.

TABLE 2

| Ligand exchange constant (K) and ligand exchange enthalpy (ΔH) determined for the exchange of Cu(II) between 2HQ by DOTA, TETA, cyclam, cyclen and DOTP (reaction scheme 1). | | | | | |
|---|---|---|---|---|---|
| | DOTA | TETA | Cyclam | Cyclen | DOTP |
| | | | K | | |
| pH 4.0 at 25° C. | $1.3 \times 10^{-2}$ | $1.2 \times 10^{-4}$ | * | * | $2.5 \times 10^{-3}$ |
| pH 4.0 at 50° C. | $8.7 \times 10^{-3}$ | ~ | * | * | $2.9 \times 10^{-3}$ |
| pH 5.9 at 25° C. | $6.1 \times 10^{-4}$ | $3.0 \times 10^{-3}$ | ^ | ^ | ~ |
| pH 5.9 at 50° C. | $1.0 \times 10^{-3}$ | $2.8 \times 10^{-2}$ | $1.2 \times 10^{-4}$ | $1.4 \times 10^{-3}$ | ~ |
| | | | ΔH [kcal/mol] | | |
| pH 4.0 at 25° C. | 3.8 | 0.5 | * | * | 2.4 |
| pH 4.0 at 50° C. | 4.0 | ~ | * | * | 3.4 |
| pH 5.9 at 25° C. | −8.0 | −4.9 | ^ | ^ | ~ |

TABLE 2-continued

Ligand exchange constant (K) and ligand exchange enthalpy (ΔH) determined for the exchange of Cu(II) between 2HQ by DOTA, TETA, cyclam, cyclen and DOTP (reaction scheme 1).

| | DOTA | TETA | Cyclam | Cyclen | DOTP |
|---|---|---|---|---|---|
| pH 5.9 at 50° C. | −6.3 | −4.7 | −10.1 | −5.5 | ~ |

\* No binding is observed as only heat of dilution is detected.
^ Binding is observed, but the calorimetric heat trace is too low in intensity to analyze.
~ Binding is observed, but the calorimetric heat trace is too complex to analyze.

ITC measurements of the extraction of Cu(II) from 2-hydroxyquinoline (2HQ) by DOTA, TETA, cyclam, cyclen and DOTP in MES buffer (pH 5.9) and in acetate buffer (pH 4.0) at 25° C. and 50° C. performed within the present invention is shown in Table 2. The ligand exchange constant (K) and the ligand exchange enthalpy (ΔH) are determined by as fitting parameters using a binding isotherm based on reaction scheme (1). Experimental conditions: 0.05 mM $Cu(2HQ)_2$ was titrated with 2-μL injections of 0.5 mM DOTA, TETA, cyclam, cyclen or DOTP.

Based on the ITC data (Tabel 2) all the chelates can be used as agent-entrapping components chelating Cu(II). Furthermore based on the exchange constants (K) measured, Cu(II) can be extracted from 2-hydroxyquinoline by all the chelates (DOTA, TETA, cyclam, cyclen and DOTP) under the different pH- and temperature conditions outlined in Table 2.

From Table 2 the exchange of Cu(II) from 2HQ to DOTA is more favourable at pH 4.0 than at pH 5.9, and more favourable at 50° C. than 25° C. Furthermore the exchange of Cu(II) from 2HQ to TETA is more favourable at pH 5.9 than pH 4.0, and also more favourable at 50° C. compared to 25° C.

Preparation of Chelator-containing Liposomes:

Chelating agent (DOTA) was trapped within the liposomes consisting of DSPC, cholesterol and DSPE-PEG-2000 in the molar ratio 55:40:5 using the standard thin-film hydration and repeated extrusions. Briefly, the lipids were mixed in chloroform and dried to a lipid-film under a gentle stream of nitrogen. Organic solvent residues were removed under reduced pressure overnight. The lipid-film was dispersed by adding an aqueous solution, for example, a HEPES buffer (10 mM, 150 mM NaCl, pH 7.4) containing the chelating agent (DOTA) in a concentration of 10 mM, and at a pH of 4.0. The solution was hydrated at 65° C. for 60 min. The multi lamellar vesicles (MLVs) were downsized to small unilamellar vesicles (SUVs) by multiple extrusions through 100 nm polycarbonate filters using a mini-extruder. Unentrapped chelating agent was removed by size exclusion chromatography (SEC) on a Sephadex G-50 packed 1×25 cm column eluted with HEPES buffer (10 mM, 150 mM NaCl, pH 7.4).

Liposomes produced as described above also consisted of different vesicle-forming components. In Table 3 the loading efficiencies of $^{64}Cu$ into these different liposome compositions using 2-hydroxyquinoline is outlined.

TABLE 3

$^{64}Cu$-loading into different liposome composition at different incubation conditions using 2-hydroxyquinoline

| Liposome composition (% molar ratio) | Temperature | Incubation time | Loading efficiency |
|---|---|---|---|
| DSPC/CHOL/DSPE-PEG-2000 (50:40:10) | 50° C. | 60 min | 98% |
| DSPC/CHOL/DSPE-PEG-2000/DSPE-PEG-2000-TATE (50:40:9:1) | 50° C. | 60 min | 98% |
| POPC (100) | 20° C. | 60 min | 90% |
| DSPC (100) | 37° C. | 60 min | 90% |
| DPPC (100) | 25° C. | 60 min | 82% |

DSPC: 1,2-distearoyl-sn-glycero-3-phosphocholine
CHOL: Cholesterol
DSPE-PEG-2000: 1,2-distearoyl-sn-glycero-3-phosphoethanolamine-N-[methoxy (polyethylene glycol)-2000]
POPC: 1-palmitoyl-2-oleoyl-sn-glycero-3-phosphocholine
DPPC: 1,2-dipalmitoyl-sn-glycero-3-phosphocholine
DSPE-PEG-2000-TATE: 1,2-distearoyl-sn-glycero-3-phosphoethanolamine-N-[methoxy (polyethylene glycol)-2000]-TATE
TATE: Somastotatin analog (octreotate)

Additionally, the size and zeta potential of $^{64}Cu$-liposomes before and after loading of $^{64}Cu$ using the ionophore, carbostyril, were measured. As shown in Table 4 immediately below, no significant differences in size before (97.9 nm) or after (96.07 nm) $^{64}Cu$-loading were observed, or in zeta potential before (−4.09 mV) or after (−3.78 mV) the $^{64}Cu$-loading, demonstrating high in vitro stability of the $^{64}Cu$-liposomes composition prepared in the present invention.

TABLE 4

Size (nm) and zeta potential (mV) of $^{64}Cu$-Liposome compositions loaded with $^{64}Cu$ using carbostyril before and after (one week) $^{64}Cu$ loading.

| | Size (nm) | | zeta potential (mV) | |
|---|---|---|---|---|
| Lipsosome composition | before loading | after loading | before loading | after loading |
| (DSPC/CHOL/DSPE-PEG-2000) in molar ratio 55:40:5 | 97.9 ± 0.5 (n = 3) | 96.07 ± 0.77 (n = 9) | −4.09 ± 0.54 (n = 10) | −3.78 ± 0.92 (n = 50) |

Animal Tumor Models in in vivo Studies:

Human colon adenocarcinoma (HT29) tumor cells ($2×10^6$ cells) were inoculated in the left and right flank of female NMRI (Naval Medical Research Institute) nude mice and allowed to grow 4 weeks in the mice to establish the malignant solid tumor. $^{64}Cu$-liposomes for in vivo studies were prepared as described above and consisted of DSPC/CHOL/DSPE-PEG-2000 in the molar ratio 55:40:5 and contained the chelating agent (DOTA) in a concentration of 10 mM, and at a pH of 4.0 in the interior of the liposomes.

Serum Stability of $^{64}Cu$-liposomes Loaded with $^{64}Cu$ Using 2HQ:

A purified 250 μL $^{64}Cu$-liposome solution was incubated at 37° C. for 24 h in 250 μL human serum, and the stability of the $^{64}Cu$-Liposome were assayed by separating free $^{64}Cu$ from $^{64}Cu$-liposome by size exclusion chromatography (SEC) on a Sephadex G-50 column. Results from the serum stability test where $^{64}Cu$-liposomes containing 10 mM DOTA showed that more than 99% of the total radioactivity remained in the liposomes when the $^{64}Cu$ was loaded using 2HQ.

Administration of $^{64}Cu$-liposomes and $^{64}Cu$-DOTA for in vivo Biodistribution Imaging and Quantification:

$^{64}Cu$-liposome and $^{64}Cu$-DOTA suspensions were administered intravenous (i.v.) in non-tumor-bearing NMRI nude mice ($^{64}$Cu-liposome, n=7; $^{64}$Cu-DOTA, n=5) and in tumor-bearing mice ($^{64}$Cu-liposome, n=5; $^{64}$Cu-DOTA, n=3). $^{64}$Cu-DOTA serves as a control tracer representing the interior of the liposomes. The volume of injection was 100 μL per mouse. All animals were anesthetized with sevofluran and catheterized to ensure proper tail vein injection. All nude mice were purchased from Taconic (Borup, Denmark). All animal experimental procedures were conducted with the guidelines set forth by the Danish Ministry of Justice.

Positron Emission Tomography (PET)/Computed Tomography (CT) Imaging and Quantification:

After i.v. administration of $^{64}$Cu-liposome or $^{64}$Cu-DOTA the animals were subject to micro-PET/CT imaging at different time points: 1, 4, 12 and 24 h. With PET imaging the amount of radioactivity specifically sequestered in a region of interest (ROI) on an image can be calculated allowing direct quantitative determinations based on differences in signal intensity. After PET- and CT images were reconstructed the images were fused with Inveon Software (Siemens), and PET data were analyzed by defining ROIs on selected tissues. PET values are expressed as mean Becquerel ml$^{-1}$ (Bq ml$^{-1}$), and ROIs were drawn manually over each organ of interest. Dynamic PET data were acquired over the first 80 min post-injection (22 frames, with the last frame of 20 min representing the 1 h scan) followed by static scans with 20 min (4 h and 12 h) and 40 min (24 h) acquisition times.

FIG. 11 is a time-activity curve (TAC) illustrating the blood concentration-time pro-file of $^{64}$Cu-liposome and $^{64}$Cu-DOTA. The blood concentrations of $^{64}$Cu-liposome and $^{64}$Cu-DOTA were measured from the radioactive concentration within the left ventricle in the heart of each animal by drawing ROIs. The estimated left ventricle ROI (expressed as % ID ml$^{-1}$) was converted to % ID organ$^{-1}$ by normalizing to the animal blood volume estimated as 7% of the total body weight. The TAC of the blood concentration was generated by plotting each left ventricle ROI expressed as % ID organ$^{-1}$ as function of time. The total injected activity dose was measured by drawing one ROI around the animal 4 min post-injection. To evaluate the quantification of blood TAC derived from ROIs placed on the left ventricle, arterial blood samples were taken 24 h post-injection. The blood samples showed a highly comparable level of $^{64}$Cu-liposomes in the blood-pool compared with the results from ROIs placed on the left ventricle. Thus the left ventricle serves as a more representative region within the heart to accurately quantify the liposomal blood concentration. Free $^{64}$Cu-DOTA was cleared rapidly after administration through renal filtration as expected.

FIG. 12 is a time-activity curve (TAC) of tissue biodistribution of $^{64}$Cu-liposomes in vivo in mice. The biodistribution of $^{64}$Cu-liposomes within the following organs: liver, heart, spleen, muscle and tumors, is expressed as percent injected dose per organ (% ID organ$^{-1}$) as function of time. The $^{64}$Cu-liposomes reached a maximum level in the liver and spleen after 4 h and remained at a constant level hereafter, reflecting the rapid initial clearance of liposomes from the blood circulation by liver Kupffer cells and splenic macrophages. Furthermore it is well established that tumor endothelium has increased vascular permeability and the long circulating pegylated $^{64}$Cu-liposomes accumulate in tumor tissue as a consequence of this permeability. An increasing activity within the tumor site was observed and the accumulation in the tumors increases continuously as long as liposomes are circulating in the blood-stream.

Positron emission tomography (PET)/computed tomography (CT) scans were per-formed at different time points after i.v. injection of $^{64}$Cu-liposomes from where quantitative measurements from the images of the biodistribution and blood-concentration time profile were possible. FIG. 13 are PET and PET/CT images of the distribution of $^{64}$Cu-liposomes in normal and tumor-bearing mice at different time points.

The results described above demonstrate liposome compositions according to embodiments of the present invention that can be used successfully for in vivo studies. Additionally, the results demonstrate preparation of liposome compositions which include a desired entity, for example a copper isotope selected from the group consisting of, but not limited to, $^{61}$Cu, $^{64}$Cu and $^{67}$Cu, with high loading efficiency (>90%) in a stable form with minimal release (i.e. leakage) of the encapsulated entity upon storage and in human serum incubation for 24 h at 37° C. In a preferred embodiment the copper isotope is selected from the group consisting of $^{61}$Cu, $^{64}$Cu, and $^{67}$Cu. In one embodiment as described herein above, when the ionophore is carbostyril or a derivative thereof, the radionuclide may include radionuclides different from copper. The liposome compositions prepared within this invention can thus be used in nuclear imaging, including PET imaging, for in vivo cancer diagnostic applications and for diagnosing other pathological conditions associated with leaky blood vessels in a subject. These novel radiolabeled liposome compositions within the present invention are also useful in radio-therapeutic applications treating a cancer disease or another disease within a subject.

Radiolabeling of $^{177}$Lu-2HQ:

A total of 10 μL of 0.314 mM 2HQ in HEPES buffer (10 mM, 150 mM NaCl, pH 7.4) was added to 10 μL radioactive $^{177}$LuCl$_3$ (in distilled water).

Liposomes Loading with Radiolabeled $^{177}$Lu-2HQ:

Chelate-containing liposomes produced as described in "Preparation of chelator-containing liposomes" were loaded by incubating 150 MBq of 20 μL radiolabeled $^{177}$Lu-2HQ with 0.5 mL chelate-containing liposomes at 50° C. for 60 min. In the liposome, the radionuclide binds preferably to DOTA encapsulated in the interior of the liposome, allowing the release of free ionophore, 2HQ, and the entrapment of the radionuclide, $^{177}$Lu. The $^{177}$Lu loaded liposomes were assayed by separating the unentrapped radionuclide, $^{177}$Lu, from $^{177}$Lu-liposomes by size exclusion chromatography (SEC) on a Sephadex G-50 column. The elution profile was monitored on an in line radioactivity detector. $^{177}$Lu entrapment efficiency was 96%. FIG. 14A illustrates that 2HQ efficiently loads $^{177}$Lu into the interior of liposomes pre-encapsulated with DOTA.

Figure 14B:
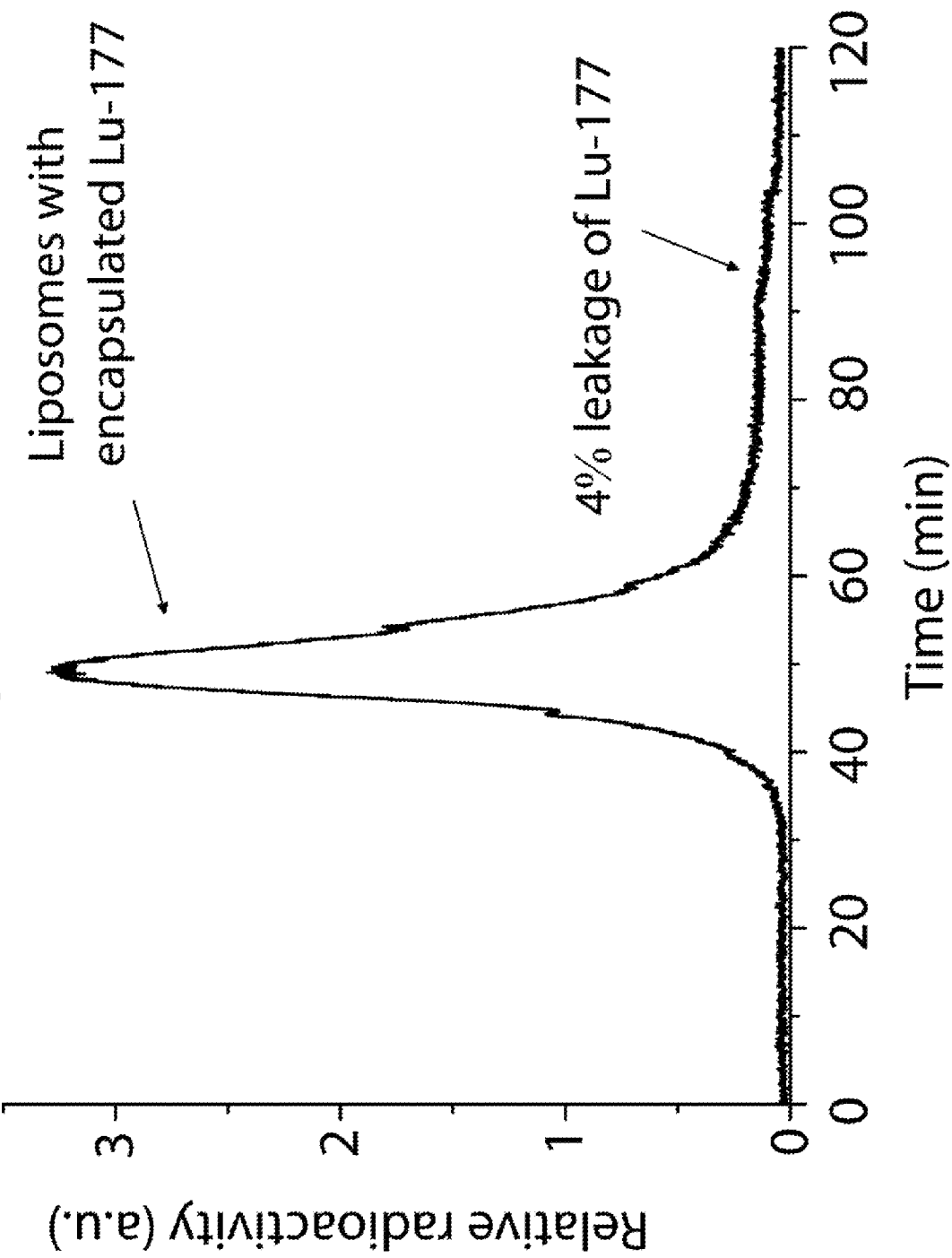

Storage Stability at 37° C. for 24 h of $^{177}$Lu-liposome Loaded with $^{177}$Lu Using 2HQ A purified 500 μL $^{177}$Lu-liposome solution loaded using 2HQ was incubated at 37° C. for 24 h, and the stability of the $^{177}$Lu-liposomes was assayed by separating unencapsulated $^{177}$Lu from $^{177}$Lu-liposome by size exclusion chromatography (SEC) on a Sephadex G-50 column. The elution profile was monitored on an in line radioactivity detector. FIG. 14B illustrates the results from the stability test (24 h, 37° C.) where $^{177}$Lu-liposomes containing 10 mM DOTA (pH 4.0) retained more than 95% of the total radioactivity when the $^{177}$Lu was loaded using carbostyril.

An example of preparing a double-radiolabeling ($^{177}$Lu and $^{64}$Cu) of 2HQ and the preparation of loading liposomes with $^{177}$Lu and $^{64}$Cu using radiolabeled $^{177}$Lu-2HQ and $^{64}$Cu-2HQ respectively for radio-therapeutic and radio-diagnostic applications included in the method of preparing the liposome compositions of the present invention follows. $^{64}$Cu represents the chemical properties of all copper isotopes.

Radiolabeling of $^{177}$Lu/$^{64}$Cu-2HQ:

A total of 10 μL of 0.314 mM 2HQ in HEPES buffer (10 mM, 150 mM NaCl, pH 7.4) was added to dried radioactive $^{64}$CuCl$_2$ together with 10 μL of radioactive $^{177}$LuCl$_3$ (in distilled water).

Loading Liposomes with $^{177}$Lu and $^{64}$Cu Using Radiolabeled $^{64}$Cu/$^{177}$Lu-2HQ:

Chelate-containing liposomes produced as described in "Preparation of chelator-containing liposomes:" were loaded by incubating 100 MBq $^{177}$Lu, 100 MBq $^{64}$Cu, 10 μL of 0.314 mM 2HQ with 0.5 mL chelate-containing liposomes at 50° C. for 60 min. The $^{64}$Cu/$^{177}$Lu loaded liposomes were assayed by separating the unentrapped radionuclides, $^{64}$Cu and $^{177}$Lu, from $^{64}$Cu/$^{177}$Lu-liposomes by size exclusion chromatography (SEC) on a Sephadex G-50 column. The elution profile was monitored on an in line radioactivity detector. FIG. 15 illustrates that 2HQ efficiently loads $^{64}$Cu and $^{177}$Lu into the interior of liposomes pre-encapsulated with DOTA. The encapsulation efficiency of $^{177}$Lu was 98% and 95% for $^{64}$Cu. A germanium detector was used to distinguish between the two gamma-ray sources ($^{64}$Cu and $^{177}$Lu) and thereby quantitatively identifying and measure the entrapment of each radionuclide in the liposomes.

The results described above demonstrate liposome compositions according to embodiments of the present invention that can be used successfully for in vivo studies. Additionally, the results demonstrate preparation of liposome compositions which include a desired entity, for example $^{177}$Lu and/or a copper isotope selected from the group consisting of, but not limited to, $^{61}$Cu, $^{64}$Cu and $^{67}$Cu, with high loading efficiency (>90%) in a stable form with minimal release (i.e. leakage) of the encapsulated entity upon storage and after incubation for 24 h at 37° C. In a preferred embodiment the copper isotope is selected from the group consisting of $^{61}$Cu, $^{64}$Cu, and $^{67}$Cu. In one embodiment as described herein above, when the ionophore is carbostyril or a derivative thereof, the radionuclide may include radionuclides different from copper for example $^{177}$Lu. The liposome compositions prepared within this invention can thus be used in nuclear imaging, including PET imaging, for in vivo cancer diagnostic applications and for diagnosing other pathological conditions associated with leaky blood vessels in a subject. Additional these novel radiolabeled liposome compositions within the present invention are also useful in radio-therapeutic applications treating a cancer disease or another disease within a subject.

The invention claimed is:

1. A method for preparing nanoparticle compositions loaded with radionuclides comprising:
   a. providing a nanoparticle composition comprising a vesicle forming component and an agent-entrapping component enclosed by said vesicle forming component;
   b. providing a component for transporting the radionuclides over the vesicle membranes, said component being an ionophore selected from the group consisting of quinoline derivatives of formula A, a stereoisomer thereof or a mixture of its stereoisomers, or a pharmaceutically acceptable salt thereof,

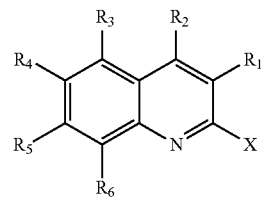

A wherein X represents hydroxy (OH), amino (NH$_2$) or sulphydryl (SH) and wherein R$_1$, R$_2$, R$_3$, R$_4$, R$_5$, and R$_6$ independently of each other, represent substituents selected from the group consisting of hydrogen (H), halo (Cl, Br, I), methyl (CH$_3$), ethyl (C$_2$H$_5$), propyl (C$_3$H$_8$), butyl (C$_4$H$_{11}$), amino (NH$_2$), dimethylamino (N(CH$_3$)$_2$), hydroxy (OH), cyano (CN), sulphydryl (SH), carboxy (COOH), β-D-galactopyranoside (C$_6$O$_6$H$_{11}$), glucoronide (C$_6$H$_9$O$_7$), sulphonyl (SO$_3$H), benzyl (C$_6$H$_4$COOH), and benzyl (C$_6$H$_5$(CH$_2$)), and wherein R$_1$ and R$_2$, R$_2$ and R$_3$, R$_3$ and R$_4$, R$_4$ and R$_5$, or R$_5$ and R$_6$—together with the aromatic ring to which they are attached—may form a benzo-fused carbocyclic aromatic ring or an aliphatic ring; and c. entrapping the radionuclides within the interior of the nanoparticle composition.

2. The method of claim 1 wherein said radionuclides comprise one or more radionuclides selected from the group consisting of Copper ($^{61}$Cu, $^{64}$Cu, and $^{67}$Cu), Indium ($^{111}$In), Technetium ($^{99m}$Tc), Rhenium ($^{186}$Re, $^{188}$Re), Gallium ($^{67}$Ga, $^{68}$Ga), Strontium ($^{89}$Sr), Samarium ($^{153}$Sm), Ytterbium ($^{169}$Yb), Thallium ($^{201}$Tl), Astatine ($^{211}$At), Lutetium ($^{177}$Lu), Actinium ($^{225}$Ac), Yttrium ($^{90}$Y), Antimony ($^{119}$Sb), Tin ($^{117}$Sn, $^{113}$Sn), Dysprosium ($^{159}$Dy), Cobalt ($^{56}$Co), Iron ($^{59}$Fe), Ruthenium ($^{97}$Ru, $^{103}$Ru), Palladium ($^{103}$Pd), Cadmium ($^{115}$Cd), Tellurium ($^{118}$Te, $^{123}$Te), Barium ($^{131}$Ba, $^{140}$Ba), Gadolinium ($^{149}$Gd, $^{151}$Gd), Terbium ($^{160}$Tb), Gold ($^{198}$Au, $^{199}$Au), Lanthanum ($^{140}$La), and Radium ($^{223}$Ra, $^{224}$Ra).

3. The method of claim 1, wherein said radionuclides are selected from the group consisting of $^{61}$Cu, $^{64}$Cu, $^{67}$Cu, $^{177}$Lu, $^{67}$Ga, $^{68}$Ga, $^{225}$Ac, $^{90}$Y, $^{186}$Re, $^{188}$Re, and $^{119}$Sb.

4. The method of claim 1, wherein said ionophore is selected from the group consisting of derivatives of A, wherein X represents hydroxy (OH).

5. The method of claim 1, wherein said ionophore is selected from the group consisting of 2-hydroxyquinoline, 2-hydroxyquinoline-4-carboxylic acid, 6-chloro-2-hydroxyquinoline, 8-chloro-2-hydroxyquinoline, 7-amino-4-methyl-2-hydroxyquinoline (carbostyril 124), 7-dimethylamino-4-methyl-2-hydroxyquinoline (carbostyril 165), 4,6-dimethyl-2-hydroxyquinoline, 4,8-dimethyl-2-hydroxyquinoline, or other 2-quinolinols compounds or stereoisomer thereof or a mixture of its stereoisomers, or a pharmaceutically acceptable salt thereof.

6. The method of claim 1 wherein said ionophore is 2-hydroxyquinoline (carbostyril).

7. The method of claim 1, wherein said vesicle-forming component comprises one or more of the compounds selected from the group consisting of phospholipids, pegylated phospholipids and cholesterol.

8. The method of claim 1, wherein the vesicle forming component comprises one or more amphiphatic compounds selected from the group of DSPC, DPPC, POPC CHOL, DSPE-PEG-2000 and DSPE-PEG-2000-TATE.

9. The method of claim 1, wherein said agent-entrapping component is selected from the group consisting of chelators, reducing agents and agents that form low solubility salts with said radionuclides.

10. The method of claim 1, wherein said agent-entrapping component is a chelator selected from the group consisting of 1,4,7,10-tetraazacyclododecane ([12]aneN$_4$); 1,4,7,10-tetraazacyclotridecane ([13]aneN$_4$); 1,4,8,11-tetraazacyclotetradecane ([14]aneN$_4$); 1,4,8,12-tetraazacyclopentadecane ([15]aneN$_4$); 1,5,9,13-tetraazacyclohexadecane ([16]aneN$_4$); ethylene-diamine-tetraacetic-acid (EDTA); and diethylene-triamine-penta-acetic acid (DTPA).

11. The method of claim 1, wherein said agent-entrapping component is a chelator selected from the group consisting of 1,4-ethano-1,4,8,11-tetraazacyclotetradecane (et-cyclam); 1,4,7,11-tetraazacyclotetradecane (iso-cyclam); 1,4,7,10-tetraazacyclododecane-1,4,7,10-tetraacetic acid (DOTA); 2-(1,4,7,10-tetraazacyclododecan-1-yl)acetate (DO1A); 2,2'-(1,4,7,10-tetraazacyclododecane-1,7-diyl) diacetic acid (DO2A); 2,2',2''-(1,4,7,10-tetraazacyclododecane-1,4,7-triyl) triacetic acid (DO3A); 1,4,7,10-tetraazacyclododecane-1,4,7,10-tetra(methanephosphonic acid) (DOTP); 1,4,7,10-tetraazacyclododecane-1,7-di(methanephosphonic acid) (DO2P); 1,4,7,10-tetraazacyclododecane-1,4,7-tri(methanephosphonic acid) (DO3P); 1,4,8,11-15 tetraazacyclotetradecane-1,4,8,11-tetraacetic acid (TETA); 2-(1,4,8,11-tetraazacyclotetradecane-1-yl)acetic acid (TE1A); 2,2'-(1,4,8,11-tetraazacyclotetradecane-1,8-diyl) diacetic acid (TE2A); ethylene-diamine-tetraacetic-acid (EDTA), and diethylene-triamine-penta-acetic acid (DTPA).

12. The method of any of the preceding claims, claim 1, wherein said agent-entrapping component is a chelator selected from the group consisting of 1,4,7,10-tetraazacyclododecane-1,4,7,10-tetraacetic acid (DOTA), 1,4,8,11-15 tetraazacyclotetradecane-1,4,8,11-tetraacetic acid (TETA), 1,4,7,10-tetraazacyclododecane-1,4,7,10-tetra(methanephosphonic acid) (DOTP), cyclam and cyclen.

13. The method of claim 1, wherein the interior pH of the nanoparticle is within the range of 3 to 8, such as 3.0 to 3.5, for example 3.5 to 4.0, such as 4.0 to 4.5, for example 4.5 to 5.0, such as 5.0 to 5.5 for example 5.5 to 6.0, such as 6.0 to 6.5, for example 6.5 to 7.0, such as 7.0 to 7.5, for example 7.5 to 8.

14. A kit of parts for preparing a nanoparticle composition by use of a method as described in claim 1, said kit comprising
a. a nanoparticle composition comprising
i. a vesicle forming component, and
ii. an agent-entrapping component enclosed by the vesicle forming component; and
b. a composition containing an ionophore selected from the group consisting of quinoline derivatives of formula A, a stereoisomer thereof or a mixture of its stereoisomers, or a pharmaceutically acceptable salt thereof,

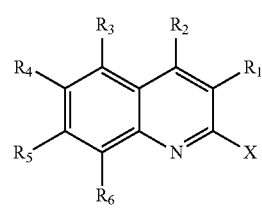

wherein X represents hydroxy (OH), amino (NH$_2$) or sulphydryl (SH) and wherein $R_1$, $R_2$, $R_3$, $R_4$, $R_5$, and $R_6$ independently of each other, represent substituents selected from the group consisting of hydrogen (H), halo (Cl, Br, I), methyl (CH$_3$), ethyl (C$_2$H$_5$), propyl (C$_3$H$_8$), butyl (C$_4$H$_{11}$), amino (NH$_2$), dimethylamino (N(CH$_3$)$_2$), hydroxy (OH), cyano (CN), sulphydryl (SH), carboxy (COON), β-D-galactopyranoside (C$_6$O$_6$H$_{11}$), glucoronide (C$_6$H$_9$O$_7$), sulphonyl (SO$_3$H), benzoyl (C$_6$H$_4$COOH), and benzyl (C$_6$H$_5$(CH$_2$)), and wherein $R_1$ and $R_2$, $R_2$ and $R_3$, $R_3$ and $R_4$, $R_4$ and $R_5$, or $R_5$ and $R_6$—together with the aromatic ring to which they are attached—may form a benzo-fused carbocyclic aromatic ring or an aliphatic ring.

* * * * *